United States Patent
Brandes et al.

(10) Patent No.: US 6,586,613 B1
(45) Date of Patent: Jul. 1, 2003

(54) SUBSTITUTED TETRAHYDRONAPHTALINE AND ANALOGOUS COMPOUNDS

(75) Inventors: Arndt Brandes, Wuppertal (DE); Michael Lögers, Wuppertal (DE); Jürgen Stoltefuss, Haan (DE); Gunter Schmidt, Wuppertal (DE); Klaus-Dieter Bremm, Recklinghausen (DE); Hilmar Bischoff, Wuppertal (DE); Delf Schmidt, Wuppertal (DE); Stefan Antons, Leverkusen (DE); Holger Paulsen, Wuppertal (DE); Stephan Nicholas Müller, Wuppertal (DE); Paul Naab, Wuppertal (DE); Carsten Schmeck, Wuppertal (DE)

(73) Assignee: Bayer Aktiengellschaft, Leverkusen (DE)

( * ) Notice: Subject to any disclaimer, the term of this patent is extended or adjusted under 35 U.S.C. 154(b) by 0 days.

(21) Appl. No.: 09/508,958

(22) PCT Filed: Sep. 16, 1998

(86) PCT No.: PCT/EP98/05874

§ 371 (c)(1),
(2), (4) Date: Mar. 17, 2000

(87) PCT Pub. No.: WO99/14174

PCT Pub. Date: Mar. 25, 1999

(30) Foreign Application Priority Data

Sep. 18, 1997 (DE) .......................... 197 41 050
Jul. 17, 1998 (DE) .......................... 198 32 159

(51) Int. Cl.$^7$ ............................ C07F 7/08
(52) U.S. Cl. .................. 556/449; 514/63; 546/14; 546/15; 549/214; 549/215; 568/808

(58) Field of Search .............. 556/449; 546/14, 546/15; 549/214, 215; 568/808; 514/63

(56) References Cited

U.S. PATENT DOCUMENTS

| | | | |
|---|---|---|---|
| 5,169,857 A | 12/1992 | Angerbauer et al. | 514/344 |
| 5,401,746 A | 3/1995 | Angerbauer et al. | 514/277 |
| 5,446,207 A | 8/1995 | Pomponi et al. | 568/633 |

FOREIGN PATENT DOCUMENTS

| | | | | |
|---|---|---|---|---|
| CA | 2209640 | 8/1998 | ......... | C07D/215/20 |
| EP | 0818448 | 1/1998 | ......... | C07D/215/20 |

OTHER PUBLICATIONS

Dinchuk, J., Hart, J., Gonzalez, G., Karmann, G., Schmidt, D., and Wirak, D. O., "Remodelling of lipoprotein in transgenic mice expressing human cholesteryl ester transfer protein", Biochimica et Biophysica Acta, 1255: 301–310 (1995).

Patton, A., Dirks, J. W., and Gust, D., "Conformational Dynamics of Polyarylbenzenes. Buttressing Effects", J. Org. Chem., 44(16): 4749–4752 (1979).

Primary Examiner—Paul F. Shaver
(74) Attorney, Agent, or Firm—Jerrie L. Chiu

(57) ABSTRACT

Substituted tetrahydro-naphthalenes and analogous compounds are prepared by reducing or condensing appropriate functional substituents in substituted tetrahydro-naphthalenes and analogous compounds by customary methods and converting functional groups in this manner into the desired groups. The compounds according to the invention are suitable for use as active compounds in pharmaceuticals, in particular in pharmaceuticals for treating arteriosclerosis and also dyslipidaemias.

12 Claims, No Drawings

SUBSTITUTED TETRAHYDRONAPHTHALINE AND ANALOGOUS COMPOUNDS

The present invention relates to substituted tetrahydronaphthalenes and analogous compounds, to processes for their preparation and to their use in pharmaceuticals.

7-(polysubstituted pyridyl)-6-heptenoates for the treatment of arteriosclerosis, lipoproteinaemia and hyperproteinaemia are known from the publication U.S. Pat. No. 5,169,857-A2. In addition, the preparation of 7-(4-aryl-3-pyridyl)-3,5-dihydroxy-6-heptenoates is described in the publication EP-325 130-A2.

The present invention relates to substituted tetrahydronaphthalenes and analogous compounds of the general formula (I),

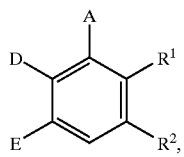

(I)

in which

A represents cycloalkyl having 3 to 8 carbon atoms, or represents aryl having 6 to 10 carbon atoms, or represents a 5- to 7-membered saturated, partially unsaturated or unsaturated, optionally benzo-fused heterocycle having up to 4 heteroatoms selected from the group consisting of S, N and/or O,
where aryl and the abovementioned heterocyclic ring systems may optionally be substituted up to 5 times by identical or different substituents selected from the group consisting of cyano, halogen, nitro, carboxyl, hydroxyl, trifluoromethyl, trifluoromethoxy, or by straight-chain or branched alkyl, acyl, hydroxyalkyl, alkylthio, alkoxycarbonyl, oxyalkoxycarbonyl or alkoxy having in each case up to 7 carbon atoms, or by a group of the formula —$NR^3R^4$
in which
$R^3$ and $R^4$ are identical or different and each represents hydrogen, phenyl or straight-chain or branched alkyl having up to 6 carbon atoms, D represents a radical of the formula

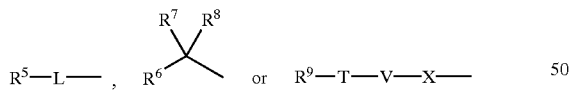

in which
$R^5$, $R^6$ and $R^9$ independently of one another each represent cycloalkyl having 3 to 6 carbon atoms, or aryl having 6 to 10 carbon atoms or a 5- to 7-membered, optionally benzo-fused, saturated or unsaturated, mono-, bi- or tricyclic heterocycle having up to 4 heteroatoms selected from the group consisting of S, N and/or O,
where the cycles are optionally, in the case of the nitrogen-containing rings also via the N-function, substituted up to 5 times by identical or different constituents selected from the group consisting of halogen, trifluoromethyl, nitro, hydroxyl, cyano, carboxyl, trifluoromethoxy, straight-chain or branched acyl, alkyl, alkylthio, alkylalkoxy, alkoxy or alkoxycarbonyl having in each case up to 6 carbon atoms, by aryl or trifluoromethyl-substituted aryl having in each case 6 to 10 carbon atoms or by an optionally benzo-fused aromatic 5- to 7-membered heterocycle having up to 3 heteroatoms selected from the group consisting of S, N and/or O,
and/or by a group of the formula —$OR^{10}$, —$SR^{11}$, —$SO_2R^{12}$ or —$NR^{13}R^{14}$,
in which
$R^{10}$, $R^{11}$ and $R^{12}$ independently of one another each represent aryl having 6 to 10 carbon atoms which for its part is substituted up to 2 times by identical or different substituents selected from the group consisting of phenyl, halogen or by straight-chain or branched alkyl having up to 6 carbon atoms,
$R^{13}$ and $R^{14}$ are identical or different and are as defined above for $R^3$ and $R^4$,
or
$R^5$ and/or $R^6$ represents/represent a radical of the formula

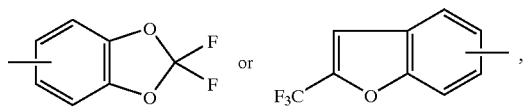

$R^7$ represents hydrogen, halogen or methyl,
and
$R^8$ represents hydrogen, halogen, azido, trifluoromethyl, hydroxyl, trifluoromethoxy, straight-chain or branched alkoxy or alkyl having in each case up to 6 carbon atoms or a radical of the formula —$NR^{15}R^{16}$,
in which
$R^{15}$ and $R^{16}$ are identical or different and are as defined above for $R^3$ and $R^4$,
or
$R^7$ and $R^8$ together form a radical of the formula =O or =$NR^{17}$,
in which
$R^{17}$ represents hydrogen or straight-chain or branched alkyl, alkoxy or acyl having in each case up to 6 carbon atoms,
L represents a straight-chain or branched alkylene or alkenylene chain, having in each case up to 8 carbon atoms, which is optionally substituted up to 2 times by hydroxyl,
T and X are identical or different and each represents a straight-chain or branched alkylene chain having up to 8 carbon atoms,
or
T or X represents a bond,
V represents an oxygen or sulphur atom or represents a —$NR^{18}$ group,
in which
$R^{18}$ represents hydrogen or straight-chain or branched alkyl having up to 6 carbon atoms or phenyl,
E represents cycloalkyl having 3 to 8 carbon atoms, or represents straight-chain or branched alkyl having up to 8 carbon atoms which is optionally substituted by cycloalkyl having 3 to 8 carbon atoms or hydroxyl, or represents phenyl, which is optionally substituted by halogen or trifluoromethyl, $R^1$ and $R^2$ together form a straight-chain or branched alkylene chain, having up to 7 carbon atoms, which has to be substituted by a carbonyl group and/or by a radical of the formula

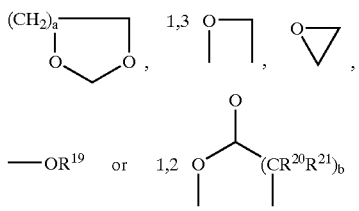

in which
a and b are identical or different and each represents a number 1, 2 or 3,
$R^{19}$ represents hydrogen, cycloalkyl having 3 to 7 carbon atoms, straight-chain or branched silylalkyl having up to 8 carbon atoms or straight-chain or branched alkyl having up to 8 carbon atoms which is optionally substituted by hydroxyl, straight-chain or branched alkoxy having up to 6 carbon atoms or by phenyl which for its part may be substituted by halogen, nitro, trifluoromethyl, trifluoromethoxy or by phenyl or tetrazole-substituted phenyl, and alkyl is optionally substituted by a group of the formula —$OR^{22}$,
in which
$R^{22}$ represents straight-chain or branched acyl having up to 4 carbon atoms or benzyl,
or
$R^{19}$ represents straight-chain or branched acyl having up to 20 carbon atoms or benzoyl which is optionally substituted by halogen, trifluoromethyl, nitro or trifluoromethoxy, or straight-chain or branched fluoracyl having up to 8 carbon atoms and 9 fluorine atoms,
$R^{20}$ and $R^{21}$ are identical or different and each represents hydrogen, phenyl or straight-chain or branched alkyl having up to 6 carbon atoms,
or
$R^{20}$ and $R^{21}$ together form a 3- to 6-membered carbocycle,
and the alkylene chain which is formed by $R^1$ and $R^2$ is optionally substituted up to 6 times, optionally also geminally, by identical or different substituents selected from the group consisting of trifluoromethyl, hydroxyl, nitrile, halogen, carboxyl, nitro, azido, cyano, cycloalkyl or cycloalkyloxy having in each case 3 to 7 carbon atoms, by straight-chain or branched alkoxycarbonyl, alkoxy or alkylthio having in each case up to 6 carbon atoms or by straight-chain or branched alkyl having up to 6 carbon atoms which for its part is substituted up to 2 times by identical or different substituents selected from the group consisting of hydroxyl, benzyloxy, trifluoromethyl, benzoyl, straight-chain or branched alkoxy, oxyacyl and carboxyl having in each case up to 4 carbon atoms and phenyl which for its part may be substituted by halogen, trifluoromethyl or trifluoromethoxy,
and/or the alkylene chain which is formed by $R^1$ and $R^2$ is optionally substituted, also geminally, up to 5 times by identical or different substituents selected from the group consisting of phenyl, benzoyl, thiophenyl and sulphonylbenzyl, which for their part are optionally substituted by halogen, trifluoromethyl, trifluoromethoxy or nitro,
and/or the alkylene chain formed by $R^1$ and $R^2$ is optionally substituted by a radical of the formula

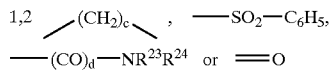

in which
c represents a number 1, 2, 3 or 4,
d represents a number 0 or 1,
$R^{23}$ and $R^{24}$ are identical or different and each represents hydrogen, cycloalkyl having 3 to 6 carbon atoms, straight-chain or branched alkyl having up to 6 carbon atoms, benzyl or phenyl, which is optionally substituted up to 2 times by identical or different substituents selected from the group consisting of halogen, trifluoromethyl, cyano, phenyl and nitro,
and/or the alkylene chain formed by $R^1$ and $R^2$ is optionally substituted by a spiro-linked radical of the formula

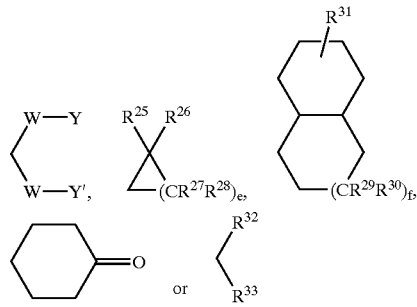

in which
W represents either an oxygen or a sulphur atom,
Y and Y' together form a 2- to 6-membered straight-chain or branched alkylene chain,
e represents a number 1, 2, 3, 4, 5, 6 or 7,
f represents a number 1 or 2,
$R^{25}$, $R^{26}$, $R^{27}$, $R^{28}$, $R^{29}$, $R^{30}$ and $R^{31}$ are identical or different and each represents hydrogen, trifluoromethyl, phenyl, halogen or straight-chain or branched alkyl or alkoxy having in each case up to 6 carbon atoms,
or
$R^{25}$ and $R^{26}$ or $R^{27}$ and $R^{28}$, in each case together, form a straight-chain or branched alkyl chain having up to 6 carbon atoms,
or
$R^{25}$ and $R^{26}$ or $R^{27}$ and $R^{28}$, in each case together, form a radical of the formula

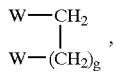

in which
W is as defined above,
g represents a number 1, 2, 3, 4, 5, 6 or 7,
$R^{32}$ and $R^{33}$ together form a 3- to 7-membered heterocycle which contains an oxygen or sulphur atom or a group of the formula SO, $SO_2$ or —$NR^{34}$,
in which
$R^{34}$ represents hydrogen, phenyl, benzyl or straight-chain or branched alkyl having up to 4 carbon atoms,
and stereoisomers, stereoisomer mixtures and salts thereof.

The compounds according to the invention may also be present in the form of their salts. In general, salts with organic or inorganic bases or acids may be mentioned here.

In the context of the present invention, preference is given to physiologically acceptable salts. Physiologically acceptable salts of the compounds according to the invention may be salts of the substances according to the invention with mineral acids, carboxylic acids or sulphonic acids. Particular preference is given, for example, to salts with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, titaric acid, citric acid, fumaric acid, maleic acid or benzoic acid.

Physiologically acceptable salts may likewise be metal or ammonium salts of the compounds according to the invention which have a free carboxyl group. Particular preference is given, for example, to sodium, potassium, magnesium or calcium salts, and also to ammonium salts which are derived from ammonia or organic amines, such as, for example, ethylamine, di- or triethylamine, di- or triethanolamine, dicyclohexylamine, dimethylaminoethanol, arginine, lysine, ethylenediamine or 2-phenylethylamine.

The compounds according to the invention may exist in stereoisomeric forms which are either like image or mirror image (enantiomers), or which are not like image and mirror image (diastereomers). The invention relates both to the enantiomers or diastereomers and to their respective mixtures. These mixtures of the enantiomers and diastereomers can be separated into the stereomerically uniform components in a known manner.

In the context of the invention, heterocycle, optionally benzo-fused, generally represents a saturated, partially saturated or unsaturated 5- to 7-membered, preferably 5- to 6-membered, heterocycle which may contain up to 4 heteroatoms selected from the group consisting of S, N and/or O. Examples include: indolyl, isoquinolyl, quinolyl, benzo[b]thiophene, benzo[b]furanyl, pyridyl, thienyl, furyl, pyrrolyl, thiazolyl, oxazolyl, imidazolyl, morpholinyl or piperidyl. Preference is given to quinolyl, furyl, pyridyl and thienyl.

Preference is given to the compounds according to the invention of the general formula (I), in which A represents cyclopentyl or represents cyclohexyl, or represents naphthyl, phenyl, pyridyl, thienyl, imidazolyl, pyrryl or morpholinyl, each of which is optionally substituted up to 2 times by identical or different substituents selected from the group consisting of fluorine, chlorine, bromine, amino, hydroxyl, trifluoromethyl, trifluoromethoxy or by straight-chain or branched alkyl, or alkoxy having in each case up to 6 carbon atoms, D represents a radical of the formula

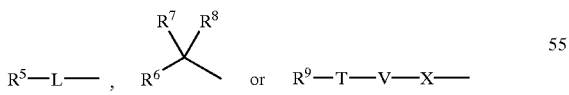

in which
R$^5$, R$^6$ and R$^9$ independently of one another each represent cyclopropyl, cyclopentyl or cyclohexyl, or phenyl, naphthyl, pyridyl, tetrazolyl, pyrimidyl, pyrazinyl, pyrrolidinyl, indolyl, morpholinyl, imidazolyl, benzothiazolyl, phenoxathiin-2-yl, benzoxazolyl, furyl, quinolyl or purin-8-yl,
where the cycles are optionally substituted up to 3 times, in the case of the nitrogen-containing rings also via the N-function, by identical or different substituents selected from the group consisting of fluorine, chlorine, bromine, trifluoromethyl, hydroxyl, cyano, carboxyl, trifluoromethoxy, straight-chain or branched acyl, alkyl, alkylthio, alkylalkoxy, alkoxy or alkoxycarbonyl having in each case up to 4 carbon atoms, triazolyl, tetrazolyl, benzoxathiazolyl, trifluoromethyl-substituted phenyl and phenyl,
and/or are substituted by a group of the formula —OR$^{10}$, —SR$^{11}$ or —SO$_2$R$^{12}$,
in which
R$^{10}$, R$^{11}$ and R$^{12}$ are identical or different and are each phenyl which for its part is substituted up to 2 times by identical or different substituents selected from the group consisting of phenyl, fluorine, chlorine or by straight-chain or branched alkyl having up to 4 carbon atoms,
or
R$^5$ and/or R$^6$ represents/represent a radical of the formula

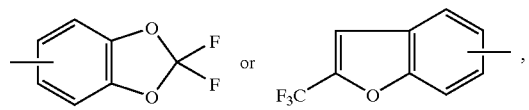

R$^7$ represents hydrogen, fluorine, chlorine or bromine, and
R$^8$ represents hydrogen, fluorine, chlorine, bromine, azido, trifluoromethyl, hydroxyl, trifluoromethoxy, straight-chain or branched alkoxy or alkyl having in each case up to 5 carbon atoms or a radical of the formula —NR$^{15}$R$^{16}$,
in which
R$^{15}$ and R$^{16}$ are identical or different and each represents hydrogen, phenyl or straight-chain or branched alkyl having up to 4 carbon atoms,
or
R$^7$ and R$^8$ together form a radical of the formula =O or =NR$^{17}$,
in which
R$^{17}$ represents hydrogen or straight-chain or branched alkyl, alkoxy or acyl having in each case up to 4 carbon atoms,
L represents a straight-chain or branched alkylene or alkenylene chain, having in each case up to 6 carbon atoms, which is optionally substituted up to 2 times by hydroxyl,
T and X are identical or different and each represents a straight-chain or branched alkylene chain having up to 6 carbon atoms,
or
T or X represents a bond,
V represents an oxygen or sulphur atom or represents a group of the formula —NR$^{18}$—,
in which
R$^{18}$ represents hydrogen or straight-chain or branched alkyl having up to 4 carbon atoms or phenyl,
E represents cyclopropyl, -butyl, -pentyl, -hexyl or -heptyl, or straight-chain or branched alkyl, having up to 6 carbon atoms, which is optionally substituted by cyclopropyl, -butyl, -hexyl, -pentyl, -heptyl or by hydroxyl, or represents phenyl which is optionally substituted by fluorine, chlorine or trifluoromethyl,
R$^1$ and R$^2$ together form a straight-chain or branched alkylene chain, having up to 6 carbon atoms, which has to be substituted by a carboxyl group and/or by a radical of the formula

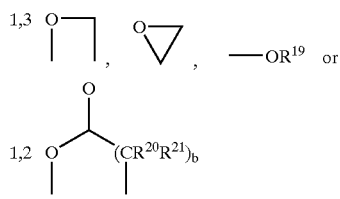, —OR$^{19}$ or

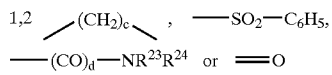

in which
b represents a number 1, 2 or 3,
R$^{19}$ represents hydrogen, cyclopropyl, cyclopentyl, cyclohexyl, straight-chain or branched silylalkyl having up to 7 carbon atoms or straight-chain or branched alkyl having up to 6 carbon atoms which is optionally substituted by hydroxyl, straight-chain or branched alkoxy having up to 4 carbon atoms or by phenyl, which for its part may be substituted by fluorine, chlorine, bromine, nitro, trifluoromethyl, trifluoromethoxy or by phenyl or tetrazole-substituted phenyl,
and alkyl is optionally substituted by a group of the formula —OR$^{22}$,
in which
R$^{22}$ represents straight-chain or branched acyl having up to 3 carbon atoms or benzyl,
or
R$^{19}$ represents straight-chain or branched acyl having up to 18 carbon atoms or benzoyl which is optionally substituted by fluorine, chlorine, bromine, trifluoromethyl, nitro or trifluoromethoxy, or straight-chain or branched fluoracyl having up to 6 carbon atoms,
R$^{20}$ and R$^{21}$ are identical or different and are each hydrogen, phenyl or straight-chain or branched alkyl having up to 4 carbon atoms,
or
R$^{20}$ and R$^{21}$ together form a cyclopropyl, cyclobutyl, cyclopentyl, cyclohexyl or cycloheptyl ring,
and the alkylene chain which is formed by R$^1$ and R$^2$ is optionally substituted up to 5 times, optionally also geminally, by identical or different substituents selected from the group consisting of trifluoromethyl, hydroxyl, carboxyl, azido, fluorine, chlorine, bromine, nitro, cyano, cyclopropyl, cyclobutyl, cyclopentyl, cyclohexyl, cyclopropyloxy, cyclopentyloxy, cyclohexyloxy, by straight-chain or branched alkoxycarbonyl, alkoxy or alkylthio having in each case up to about 5 carbon atoms or straight-chain or branched alkyl having up to 5 carbon atoms which for its part is substituted up to 2 times by identical or different substituents selected from the group consisting of hydroxyl, benzyloxy, benzoyl, straight-chain or branched alkoxy or oxyacyl having in each case up to 3 carbon atoms, trifluoromethyl and/or phenyl which for its part may be substituted by fluorine, chlorine, bromine, trifluoromethyl or trifluoromethoxy,
and/or the alkylene chain formed by R$^1$ and R$^2$ is optionally, also geminally, substituted up to 4 times by identical or different substituents selected from the group consisting of phenyl, benzoyl, thiophenyl and sulphonylbenzyl, which for their part are optionally substituted by fluorine, chlorine, bromine, trifluoromethyl, trifluoromethoxy or nitro, and/or is optionally substituted by a radical of the formula

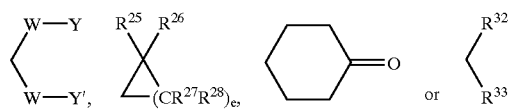

in which
c represents a number 1, 2, 3 or 4,
d represents a number 0 or 1,
R$^{23}$ and R$^{24}$ are identical or different and each represents hydrogen, cyclopropyl, cyclobutyl, cyclopentyl, cyclohexyl, straight-chain or branched alkyl, having up to 5 carbon atoms, phenyl or benzyl, which is optionally substituted by fluorine, chlorine, bromine, phenyl or trifluoromethyl,
and/or the alkylene chain formed by R$^1$ and R$^2$ is optionally substituted by a spiro-linked radical of the formula

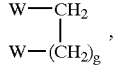

in which
W is either an oxygen or a sulphur atom,
Y and Y' together form a 2- to 5-membered straight-chain or branched alkyl chain,
e represents a number 1, 2, 3, 4, 5 or 6,
R$^{25}$, R$^{26}$, R$^{27}$ and R$^{28}$ are identical or different and each represents hydrogen, trifluoromethyl, phenyl, fluorine, chlorine, bromine or straight-chain or branched alkyl or alkoxy having in each case up to 5 carbon atoms,
or
R$^{25}$ and R$^{26}$ or R$^{27}$ and R$^{28}$, in each case together, form a straight-chain or branched alkyl chain having up to 5 carbon atoms or
R$^{25}$ and R$^{26}$ or R$^{27}$ and R$^{28}$, in each case together, form a radical of the formula W—CH$_2$
|
W—(CH$_2$)$_g$, in which
W is as defined above,
g represents a number 1, 2, 3, 4, 5 or 6,
R$^{32}$ and R$^{33}$ together form a 5- to 6-membered heterocycle which contains an oxygen or sulphur atom or a group of the formula NH or NCH$_3$, and stereoisomers, stereoisomer mixtures and salts thereof.
Particular preference is given to compounds of the general formula (I) according to the invention in which
A represents phenyl, pyridyl or thienyl, which are optionally substituted up to 2 times by identical or different substituents selected from the group consisting of fluorine, chlorine, bromine, hydroxyl, trifluoromethyl, trifluoromethoxy or by straight-chain or branched alkyl or alkoxy having in each case up to 5 carbon atoms, D represents a radical of the formula

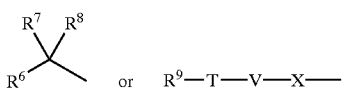 or $R^9$—T—V—X— in which
R$^6$ and R$^9$ independently of one another each represent cyclopropyl, cyclopentyl or cyclohexyl, or
phenyl, naphthyl, pyridyl, tetrazolyl, pyrimidyl, pyrazinyl, phenoxathiin-2-yl, indolyl, imidazolyl, pyrrolidinyl, morpholinyl, benzothiazolyl, benzoxazolyl, furyl, quinolyl or purin-8-yl,
where the cycles are optionally substituted up to 3 times, in the case of the nitrogen-containing rings also via the N-function, by identical or different substituents selected from the group consisting of fluorine, chlorine, trifluoromethyl, hydroxyl, cyano, carboxyl, trifluoromethoxy, straight-chain or branched alkyl, alkylthio, alkylalkoxy, alkoxy or alkoxycarbonyl having in each case up to 4 carbon atoms, triazolyl, tetrazolyl, benzothiazolyl, trifluoromethyl-substituted phenyl or phenyl and/or substituted by a group of the formula —OR$^{10}$, —SR$^{11}$ or —SO$_2$R$^{12}$,
in which
R$^{10}$, R$^{11}$ and R$^{12}$ are identical or different and each represents phenyl which for its part is substituted up to 2 times by identical or different substituents selected from the group consisting of phenyl, fluorine, chlorine or by straight-chain or branched alkyl having up to 3 carbon atoms,
or
R$^6$ represents a radical of the formula

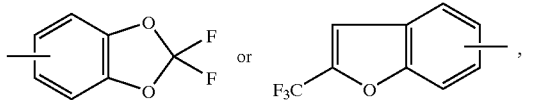

R$^7$ represents hydrogen or fluorine,
and
R$^8$ represents hydrogen, fluorine, chlorine, azido, trifluoromethyl, hydroxyl, trifluoromethoxy, or straight-chain or branched alkoxy or alkyl having in each case up to 4 carbon atoms or a radical of the formula —NR$^{15}$R$^{16}$,
in which
R$^{15}$ and R$^{16}$ are identical or different and each represents hydrogen or straight-chain or branched alkyl having up to 3 carbon atoms,
or
R$^7$ and R$^8$ together form a radical of the formula =O or =NR$^{17}$,
in which
R$^{17}$ represents hydrogen or straight-chain or branched alkyl, alkoxy or acyl having in each case up to 4 carbon atoms,
L represents a straight-chain or branched alkylene or alkenylene chain, having in each case up to 5 carbon atoms, which is optionally substituted up to 2 times by hydroxyl,
T and X are identical or different and each represents a straight-chain or branched alkylene chain having up to 3 carbon atoms,
or
T or X represents a bond,
V represents an oxygen or sulphur atom or represents a group of the formula —NR$^{18}$,
in which
R$^{18}$ represents hydrogen or straight-chain or branched alkyl having up to 3 carbon atoms,
E represents cyclopropyl, cyclobutyl, cyclopentyl or cyclohexyl or phenyl which is optionally substituted by fluorine or trifluoromethyl, or
represents straight-chain or branched alkyl, having up to 4 carbon atoms, which is optionally substituted by hydroxyl,
R$^1$ and R$^2$ together form a straight-chain or branched alkylene chain, having up to 5 carbon atoms, which has to be substituted by a carbonyl group and/or a radical of the formula

 or —OR$^{19}$ in which
R$^{19}$ represents hydrogen, cyclopropyl, cyclopentyl, cyclohexyl, straight-chain or branched silylalkyl having up to 6 carbon atoms or straight-chain or branched alkyl, having up to 4 carbon atoms, which is optionally substituted by hydroxyl, straight-chain or branched alkoxy having up to 3 carbon atoms or by phenyl, which for its part may be substituted by fluorine, chlorine, bromine, nitro, trifluoromethyl, trifluoromethoxy or by phenyl or tetrazole-substituted phenyl,
and alkyl is optionally substituted by a group of the formula —OR$^{22}$,
in which
R$^{22}$ is straight-chain or branched acyl having up to 3 carbon atoms or benzyl,
or
R$^{19}$ is straight-chain or branched acyl having up to 15 carbon atoms or benzoyl which is optionally substituted by fluorine, chlorine, bromine, trifluoromethyl, nitro or trifluoromethoxy, or straight-chain or branched fluoracyl having up to 4 carbon atoms,
and the alkylene chain formed by R$^1$ and R$^2$ is optionally substituted up to 4 times, optionally also geminally, by identical or different substituents selected from the group consisting of fluorine, hydroxyl, trifluoromethyl, carboxyl, azido, chlorine, bromine, nitro, cyano, cyclopropyl, cyclobutyl, cyclopentyl, cyclohexyl, cyclopropyloxy, cyclopentyloxy, cyclohexyloxy, by straight-chain or branched alkoxycarbonyl, alkoxy or alkylthio having in each case up to 4 carbon atoms or by straight-chain or branched alkyl, having up to 4 carbon atoms, which for its part is substituted up to 2 times by identical or different constituents selected from the group consisting of hydroxyl, benzyloxy, trifluoromethyl, benzoyl, methoxy, oxyacetyl and/or phenyl which for its part may be substituted by fluorine, chlorine, bromine, trifluoromethyl or trifluoromethoxy,
and/or the alkylene chain which is formed by R$^1$ and R$^2$ is optionally substituted, also geminally, up to 4 times by identical or different substituents selected from the group consisting of phenyl, benzoyl, thiophenyl and sulphonylbenzyl which for their part are optionally substituted by fluorine, trifluoromethyl, trifluoromethoxy or nitro, and/or is optionally substituted by a radical of the formula

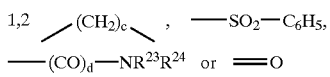

in which
c represents a number 1, 2, 3 or 4,
d represents a number 0 or 1,
$R^{23}$ and $R^{24}$ are identical or different and each represents hydrogen, cyclopropyl, cyclopentyl, benzyl, straight-chain or branched alkyl having up to 4 carbon atoms or phenyl which is optionally substituted by fluorine, chlorine or bromine,
and/or the alkylene chain formed by $R^1$ and $R^2$ is optionally substituted by a spiro-linked radical of the formula

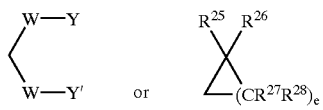

in which
W represents either an oxygen or a sulphur atom,
Y and Y' together form a 2- to 6-membered straight-chain or branched alkylene chain,
e represents a number 1, 2, 3, 4 or 5,
$R^{25}$, $R^{26}$, $R^{27}$ and $R^{28}$ are identical or different and each represents hydrogen, trifluoromethyl, phenyl, fluorine, chlorine, bromine or straight-chain or branched alkyl or alkoxy having in each case up to 4 carbon atoms,
or
$R^{25}$ and $R^{26}$ or $R^{27}$ and $R^{28}$, in each case together, form a straight-chain or branched alkyl chain having up to 4 carbon atoms,
or
$R^{25}$ and $R^{26}$ or $R^{27}$ and $R^{28}$, in each case together, form a radical of the formula

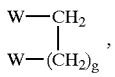

in which
W is as defined above,
g represents a number 1, 2, 3, 4, 5, 6 or 7,
and stereoisomers, stereoisomer mixtures and salts thereof.
Very particular preference is given to the compounds of the general formula (I) according to the invention in which
A represents optionally fluorine-substituted phenyl, in particular 4-fluorophenyl,
and
D represents a radical of the formula

in which
$R^6$ represents phenyl or trifluoromethyl-substituted phenyl, preference being given to trifluoromethyl-substituted phenyl,
$R^7$ represents hydrogen, $R^8$ represents hydrogen, fluorine, methoxy or hydroxyl, preference being given to fluorine,
or
$R^7$ and $R^8$ together form a carbonyl group,
E represents cyclopropyl, cyclopentyl or cyclohexyl, or represents straight-chain or branched alkyl, having up to 4 carbon atoms, which is optionally substituted by hydroxyl,
and
$R^1$ and $R^2$ together represent a radical of the formula

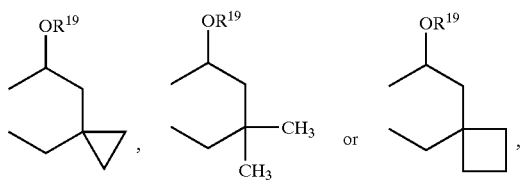

in which
$R^{19}$ represents hydrogen,
and stereoisomers, stereoisomer mixtures and salts thereof.

The compounds of the general formula (I) can be prepared when

[A] compounds of the general formula (II)

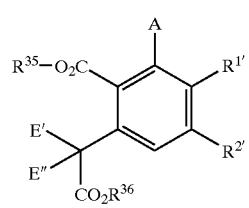

(II)

in which
A is as defined above,
$R^{35}$ and $R^{36}$ are identical or different and each represents straight-chain or branched alkyl having up to 4 carbon atoms,
$R^{1'}$ and $R^{2'}$ together represent the straight-chain or branched alkylene chain, having up to 7 carbon atoms, mentioned above under $R^1$ and $R^2$, which is substituted by tert-butyl-dimethyl-silanyloxy (OTBS),
and
E' and E" together with the carbon atom to which they are attached have the range of meanings of E given above,
are initially converted by selective reduction of the aliphatic ester and subsequent reaction with compounds of general formula (III)

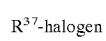

$R^{37}$-halogen  (III)

in which
$R^{37}$ represents mesyl, tosyl or sulphonyl,
and
Halogen represents chlorine, bromine or iodine, preferably chlorine,
in inert solvents, in the presence of a base, into the compounds of the general formula (IV)

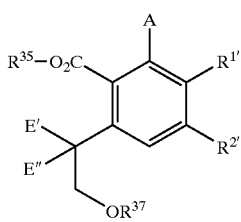
(IV)

in which
A, E', E", R$^{1'}$, R$^{2'}$, R$^{35}$ and R$^{37}$ are each as defined above,
these are converted in a further step, depending on the definitions of E'/E" given above, either by a two-fold reduction or by hydrolysis, Barton reaction and a reduction, into the compounds of the general formula (V)

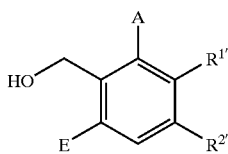
(V)

in which
A, E, R$^{1'}$ and R$^{2'}$ are each as defined above,
the aldehydes of the general formula (VI)

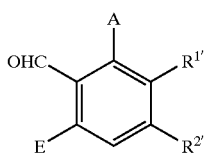
(VI)

in which
A, E, R$^{1'}$ and R$^{2'}$ are each as defined above,
are subsequently prepared by oxidation
and finally, for example by a Grignard reaction, the formyl group is converted into the radical D and the TBS group is cleaved off by customary methods,
or

[B] compounds of the general formula (VI)

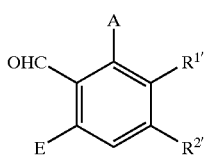
(VI)

in which
A, E, R$^{1'}$ and R$^{2'}$ are each as defined above,
are initially, as described in [A], converted in a Grignard reaction with compounds of the general formula (VII)

R$^{38}$—MgBr (VII)

in which
R$^{38}$ has the meaning of R$^5$ and R$^6$ given above,
in inert solvents and under an atmosphere of protective gas, into the compounds of the general formula (VIII)

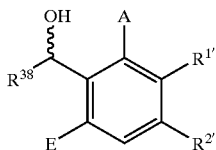
(VIII)

in which
A, D, E, R$^{38}$, R$^{1'}$ and R$^{2'}$ are each as defined above,
if appropriate on this stage starting from the hydroxyl function the substituents R$^7$/R$^8$ given under D are introduced by customary methods,
and the TBS group is subsequently cleaved off using tetrabutylammoniumfluoride in inert solvents,
or

[C] compounds of the general formula (IX)

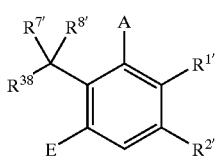
(IX)

in which
A, E, R$^{1'}$, R$^{2'}$ and R$^{38}$ are each as defined above
and
R$^{7'}$ and R$^{8'}$ together represent the carbonyl group,
are initially reduced to the compounds of the general formula (VIII) and subsequently reacted as described under [A],
or

[D] compounds of the general formula (X)

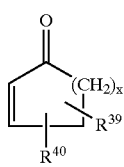
(X)

in which
x represents a number 1, 2 or 3,
and
R$^{39}$ and R$^{40}$ are identical or different and each represents hydrogen or represents straight-chain or branched alkyl having up to 6 carbon atoms,
it also being possible for R$^{39}$ and R$^{40}$ to be positioned geminally,
or
R$^{39}$ and R$^{40}$ together form a spiro-linked carbocycle having 3 to 7 carbon atoms,
are converted with compounds of the general formula (XI)

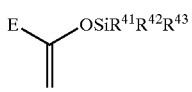
(XI)

where
E is as defined above,
and
$R^{41}$, $R^{42}$ and $R^{43}$ are identical or different and each represents straight-chain or branched alkyl having up to 10 carbon atoms, in the presence of a metal or semi-metal reagent, initially via the intermediate stage of the general formula (XII)

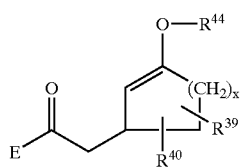
(XII)

in which
x, E, $R^{39}$ and $R^{40}$ are each as defined above,
and
$R^{44}$ represents metal or semi-metal derivatives, preferably those of titanium, and by addition of the compounds of the general formula (XIII)

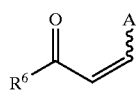
(XIII)

in which
$R^6$ and A are each as defined above, via intermediates of the general formula (XIV)

(XIV)

in which
A, E, $R^6$, $R^{39}$, $R^{40}$, $R^{44}$ and x are each as defined above,
into the compounds of the general formula (XV)

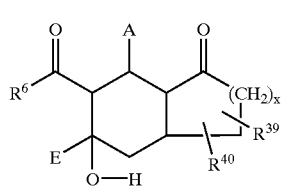
(XV)

in which
A, E, $R^6$, $R^{39}$, $R^{40}$ and x are each as defined above,
the compounds of the general formula (XVI)

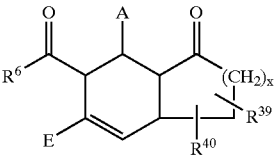
(XVI)

in which
A, E, $R^6$, $R^{39}$, $R^{40}$ and x are each as defined above,
are subsequently prepared by an elimination, halogen compounds, for example the compounds of the general formula (XVII) and/or (XVIIa)

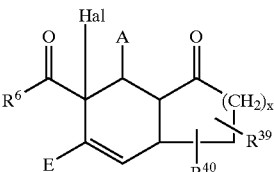
(XVII)

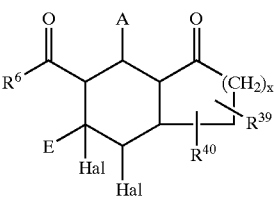
(XVIIa)

in which
$R^6$, $R^{39}$, $R^{40}$, x, A and E are as defined above,
and
Hal represents halogen, preferably chlorine or bromine,
are prepared in a further step by a halogenation via the cyclohexadienes of the general formula (XVIII), which are formed in situ, or isomers thereof

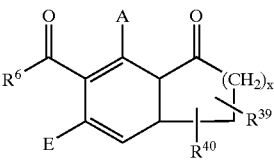
(XVIII)

in which
A, E, x, $R^6$, $R^{39}$ and $R^{40}$ are each as defined above,
compounds of the general formula (XIX)

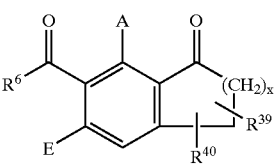
(XIX)

in which
A, E, x, $R^6$, $R^{39}$ and $R^{40}$ are each as defined above
are prepared after oxidation,
furthermore, the compounds of the general formula (XX)

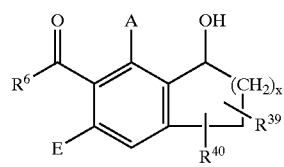
(XX)

in which
A, E, x, $R^6$, $R^{39}$ and $R^{40}$ are each as defined above,
are prepared by the reduction of the ketofunction, it also being possible to carry out the reduction stereoselectively,
the compounds of the general formula (XXI)

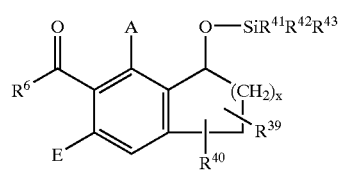
(XXI)

in which
x, A, E, $R^6$, $R^{39}$, $R^{40}$, $R^{41}$, $R^{42}$ and $R^{43}$ are each as defined above,
are subsequently prepared by silylation, for example by reaction with chlorinated or trifluoromethanesulfonyl-substituted silyl compounds (—$SiR^{41}R^{42}R^{43}$)
furthermore, the compounds of the general formula (XXII)

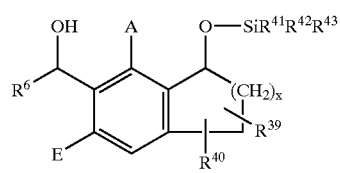
(XXII)

in which
x, A, E, $R^6$, $R^{39}$, $R^{40}$, $R^{41}$, $R^{42}$ and $R^{43}$ are each as defined above,
are obtained initially by reduction of the second ketone function, as a mixture of diastereomers from which subsequently, by separation, the isomer of the general formula (XXIII)

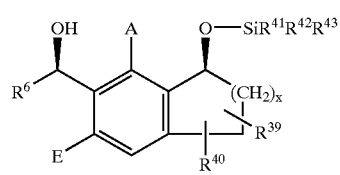
(XXIII)

in which
x, A, E, $R^6$, $R^{39}$, $R^{40}$, $R^{41}$, $R^{42}$ and $R^{43}$ are each as defined above are obtained,
and, if appropriate, the hydroxyl function is replaced enantioselectively by nucleophilic substitution by one of the substituents listed above under $R^8$, thus giving compounds of the general formula (XXIV)

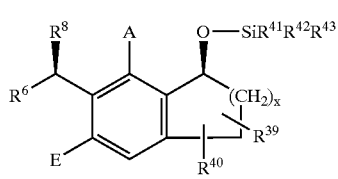
(XXIV)

in which
x, A, E, $R^6$, $R^8$, $R^{39}$, $R^{40}$, $R^{41}$, $R^{42}$ and $R^{43}$ are each as defined above
and, in a last step, the hydroxyl function is liberated according to customary methods by cleaving off the silyl protective group,
and, in the case of enantiomers/racemates, is separated by customary methods, where the structures of the general formulae (XV), (XVI), (XVII), (XVIIa) and (XVIII) may occur in isomeric forms (i.e. enantiomers, diastereomers, regioisomers).

The processes according to the invention can be illustrated by way of example by the following schemes:

[A]

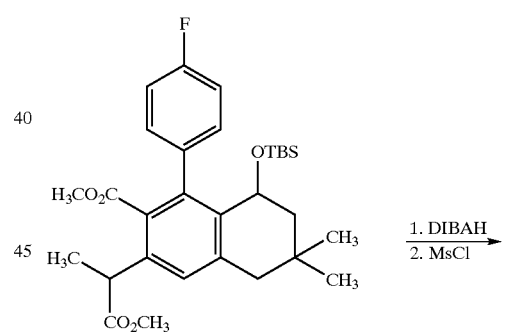

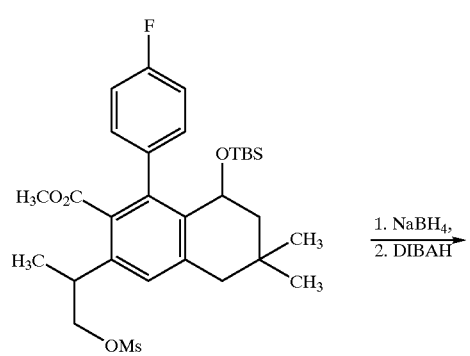

19
-continued
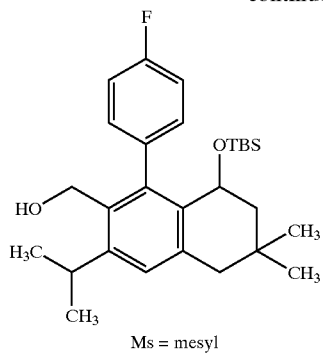
1. SO₃xPy, DMSO
2. F₃CC₆H₄MgBr, THF
3. DAST, toluene
4. TBAF, THF
5. enantiomer selection
Ms = mesyl
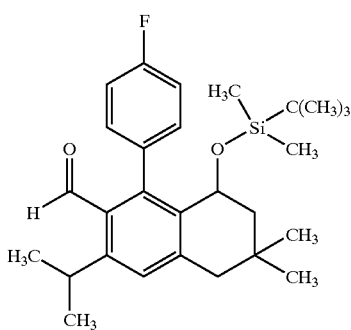
[B]
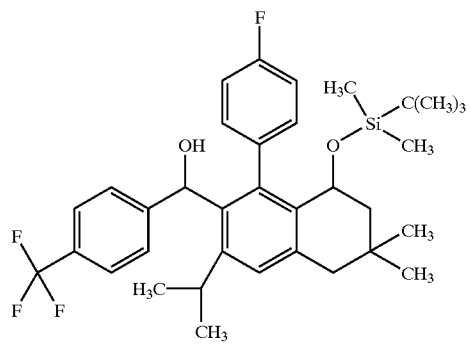
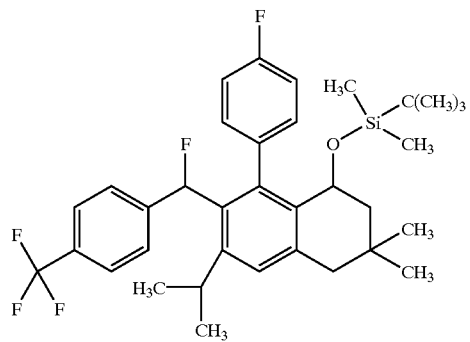
20
-continued
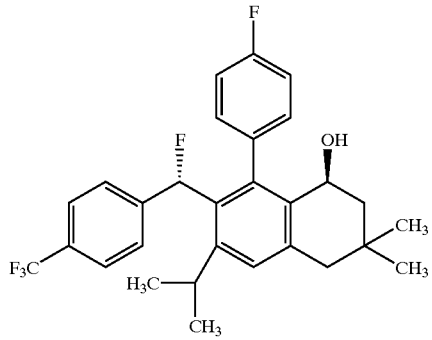
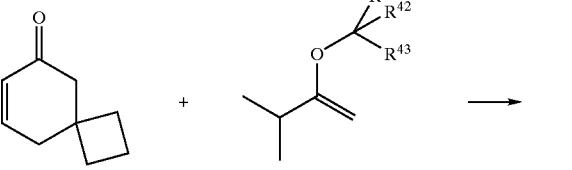  [D]
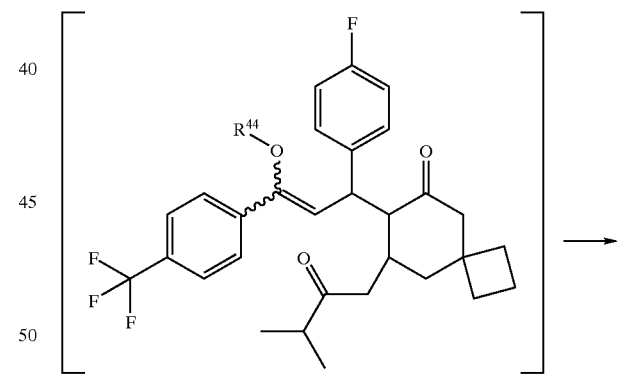
Intermediate reacted
further in situ; intermediate
and diketone
(= hydrolysis product)
can be isolated
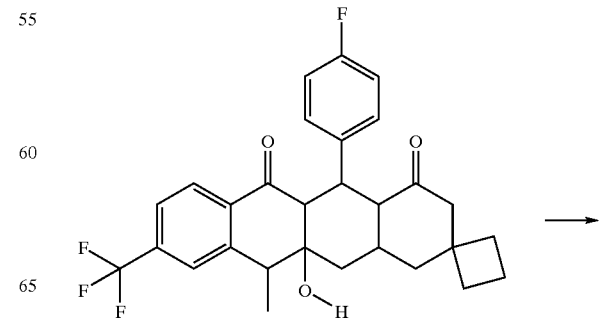
Intermediate reacts further in situ;
triketone (= hydrolysis product) can be prepared
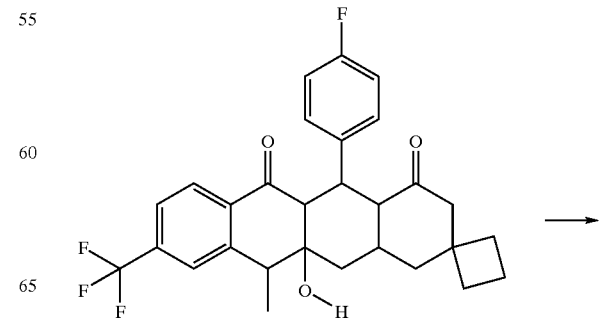

21
-continued
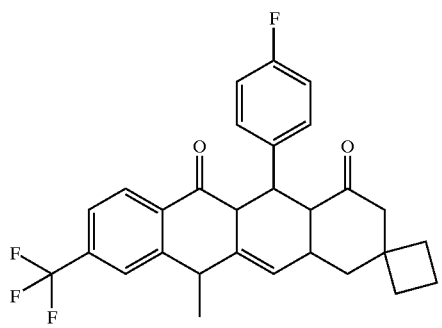
Mixture of double-bond isomeric
cyclohexenes (central ring)
* $R^{41}$, $R^{42}$, $R^{43}$, $R^{44}$ and Hal are as defined above.
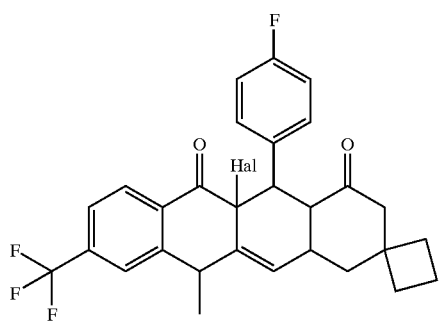
Mixture of isomeric halogen
cyclohexenes (central ring)
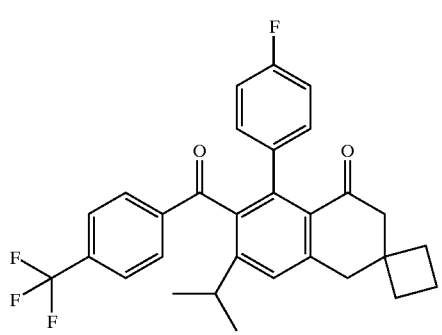
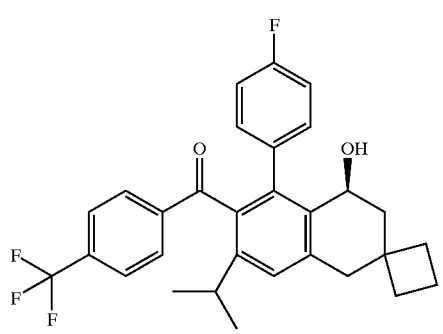
22
-continued
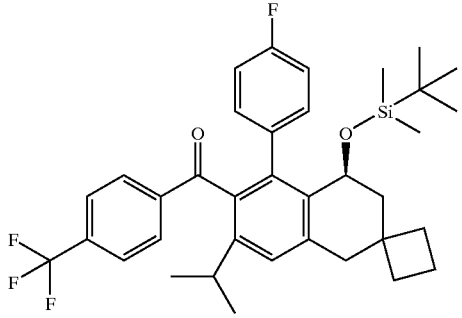 →
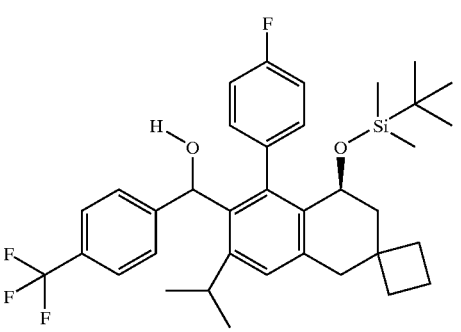
syn/anti-diastereomer mixture,
can be separated, main component: syn
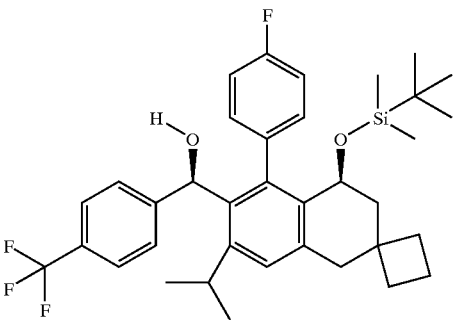
syn-diastereomer
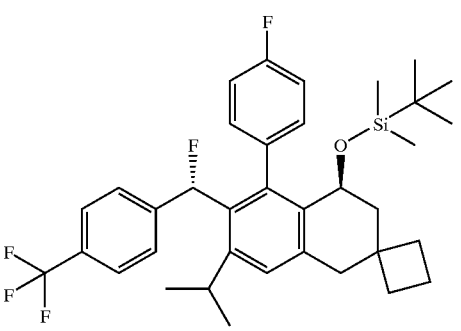 →

-continued

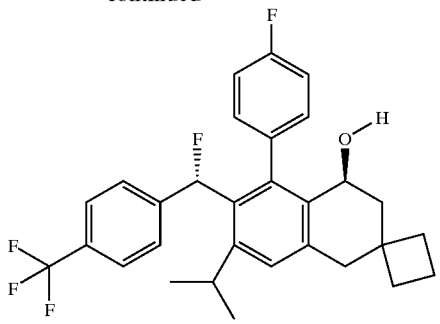

Suitable solvents for all processes are ethers, such as diethyl ether, dioxane, tetrahydrofuran, glycol dimethyl ether, or hydrocarbons, such as benzene, toluene, xylene, hexane, cyclohexane or petroleum fractions, or halogenated hydrocarbons, such as dichloromethane, trichloromethane, carbon tetrachloride, dichloroethylene, trichloroethylene or chlorobenzene, or ethyl acetate, or triethylamine, pyridine, dimethyl sulphoxide, dimethylformamide, hexamethylphosphoric triamide, acetonitrile, acetone or nitromethane. Likewise, it is possible to employ mixtures of the abovementioned solvents. Preference is given to toluene and dichloromethane.

Suitable bases for the individual steps are the customary strongly basic compounds. These preferably include organolithium compounds, such as, for example, n-butyllithium, sec-butyllithium, tert-butyllithium or phenyllithium, or amides, such as, for example, lithium diisopropylamide, sodium amide, DBU or potassium amide, or lithium hexamethylsilylamide, or alkali metal hydrides, such as sodium hydride or potassium hydride. Particular preference is given to using n-butyllithium, DBU, sodium hydride or lithium diisopropylamide.

Additionally suitable for the processes are the customary inorganic bases. These preferably include alkali metal hydroxides or alkaline earth metal hydroxides, such as, for example, sodium hydroxide, potassium hydroxide or barium hydroxide, or alkali metal carbonates, such as sodium carbonate or potassium carbonate or sodium bicarbonate. Particular preference is given to sodium hydride or potassium hydroxide.

Suitable organometallic reagents are, for example, systems such as Mg/bromobenzo-trifluoride and p-trifluoromethylphenyllithium.

The reductions of the compounds of the general formulae (II) and (IV) generally proceed under the following reaction conditions:

The reductions are generally carried out using reducing agents, preferably those which are suitable for reducing ketones to hydroxyl compounds. Particularly suitable for this purpose is the reduction using metal hydrides or complex metal hydrides in inert solvents, if appropriate in the presence of a trialkylborane. The reduction is preferably carried out using complex metal hydrides, such as, for example, lithium borohydride, sodium borohydride, potassium borohydride, zinc borohydride, lithium trialkyl borohydride, diisobutylaluminium hydride or lithium aluminium hydride. The reduction is very particularly preferably carried out using diisobutylaluminium hydride and sodium borohydride.

The reducing agent is generally employed in an amount of from 1 to 6 mol, preferably of from 1 to 4 mol, based on 1 mol of the compounds to be reduced.

The reduction generally proceeds in a temperature range of from −78° C. to +50° C., preferably of from −78° C. to 0° C. in the case of DIBAH, of from 0° C. to room temperature in the case of $NaBH_4$, particularly preferably at −78° C., in each case depending on the choice of the reducing agent and the solvent.

The reduction generally proceeds at atmospheric pressure, but it is also possible to carry out the reaction at elevated or reduced pressure.

The reactions with the compounds of the general formula (III) proceed in one of the abovementioned solvents, preferably with diethyl ether.

Bases which are suitable for this purpose are generally the customary strongly basic compounds. These preferably include di- and trialkylamines, such as, for example, triethylamine, or organolithium compounds, such as, for example, n-butyllithium, sec-butyllithium, tert-butyllithium or phenyllithium, or amides, such as, for example, lithium diisopropylamide, sodium amide or potassium amide, or lithium hexamethylsilylamide, or alkali metal hydrides, such as sodium hydride or potassium hydride. Triethylamine is particularly preferably used.

Suitable bases are furthermore the customary inorganic bases. These preferably include alkali metal hydroxides or alkaline earth metal hydroxides, such as, for example, sodium hydroxide, potassium hydroxide or barium hydroxide, or alkali metal carbonates, such as sodium carbonate or potassium carbonate or sodium bicarbonate. Particular preference is given to using potassium hydroxide.

The bases are generally employed in an amount of from 1 mol to 4 mol, preferably of from 1 mol to 2 mol, based on 1 mol of the compounds of the general formula (III).

The reaction generally proceeds at a temperature of from −30° C. to room temperature, preferably of from −20° C. to 0° C.

The reaction generally proceeds at atmospheric pressure, but it is also possible to carry out the reaction at elevated or reduced pressure.

The reaction of the compounds of the general formula (V) is generally carried out under the following reaction conditions:

Solvents which are suitable for all processes are ethers, such as diethyl ether, dioxane, tetrahydrofuran, glycol dimethyl ether, or hydrocarbons, such as benzene, toluene, xylene, hexane, cyclohexane or petroleum fractions, or halogenated hydrocarbons, such as dichloromethane, trichloromethane, carbon tetrachloride, dichloroethylene, trichloroethylene or chlorobenzene, or ethyl acetate, or triethylamine, pyridine, dimethylsulphoxide, dimethylformamide, hexamethylphosphoric triamide, acetonitrile, acetone or nitromethane. Likewise, it is possible to use mixtures of the abovementioned solvents. Preference is given to dichloromethane.

Suitable bases for the individual steps are the customary strongly basic compounds. These preferably include pyridine or organolithium compounds, such as, for example, n-butyllithium, sec-butyllithium, tert-butyllithium or phenyllithium, or amides, such as, for example lithium diisopropylamide, sodium amide or potassium amide, or lithium hexamethylsilylamide, or alkali metal hydride, such as sodium hydride or potassium hydride. Particular preference is given to using pyridine.

Suitable for the processes [B] and [C] are furthermore the customary inorganic bases. These preferably include alkali metal hydroxides or alkaline earth metal hydroxides, such as, for example sodium hydroxide, potassium hydroxide or barium hydroxide, or alkali metal carbonates, such as sodium carbonate or potassium carbonate or sodium bicarbonate. Particular preference is given to using sodium hydride or potassium hydroxide.

Suitable organometallic reagents are, for example, systems such as Mg/bromobenzotrifluoride and p-trifluoromethylphenyllithium.

The base is employed in an amount of from 0.1 mol to 5 mol, preferably of from 0.5 mol to 2 mol, in each case based on 1 mol of the starting material.

The reaction with Grignard reagents is generally carried out in a temperature range of from 0° C. to 150° C., preferably at from 25° C. to 40° C.

The Grignard reactions are generally carried out under atmospheric pressure. However, it is also possible to carry out the process at reduced pressure or at elevated pressure (for example in a range of from 0.5 to 5 bar).

The halogenations are generally carried out in one of the abovementioned chlorinated hydrocarbons and hydrocarbons, and preference is given to methylene chloride and toluene.

Suitable halogenating agents are, for example, diethylamino-sulphur trifluoride (DAST), morpholino-sulphur trifluoride or $SOCl_2$.

The halogenation generally proceeds in a temperature range of from –78° C. to +50° C., preferably of from –78° C. to 0° C., in each case depending on the choice of the halogenating agent and the solvent.

The halogenation generally proceeds at atmospheric pressure, but it is also possible to carry out the reaction at elevated or reduced pressure.

The protective group is generally cleaved off in one of the abovementioned alcohols and THF, preferably methanol/THF in the presence of hydrochloric acid in a temperature range of from 0° C. to 50° C., preferably at room temperature, and at atmospheric pressure. In particular cases, preference is given to cleaving off the protective group using tetrabutylammonium fluoride (TBAF) in THF at room temperature.

The reaction of the compounds of the general formula (VI) with the compounds of the general formula (VII) is carried out in one of the abovementioned ethers, preferably in tetrahydrofuran, under an atmosphere of protective gas in a temperature range of from –78° C. to –10° C., preferably at –25° C.

The derivatization of the hydroxyl function into the compounds of the general formula (VIII) is carried out, for example, by oxidations, sulphonations, alkylations, hydrogenations, halogenation, Wittig/Grignard reactions and sulphur amidations.

Suitable bases for the individual steps are the customary strongly basis compounds. These preferably include organolithium compounds, such as, for example, n-butyllithium, sec-butyllithium, tert-butyllithium or phenyllithium, or amides, such as, for example, lithium diisopropylamide, sodium amide or potassium amide, or lithium hexamethylsilylamide, or alkali metal hydrides, such as sodium hydride or potassium hydride. Particular preference is given to using n-butyllithium, sodium hydride or lithium diisopropylamide.

Suitable bases are furthermore the customary inorganic bases. These preferably include alkali metal hydroxides or alkaline earth metal hydroxides, such as, for example, sodium hydroxide, potassium hydroxide or barium hydroxide, or alkali metal carbonates, such as sodium carbonate or potassium carbonate or sodium bicarbonate. Particular preference is given to using sodium hydroxide or potassium hydroxide.

If appropriate, it is required to carry out some reaction steps under an atmosphere of protective gas.

The reduction of the carbonyl group in the compounds of the general formula (IX) is generally carried out under the abovementioned reaction conditions, preferably using sodium bis-(2-methoxyethoxy)-dihydroaluminate in toluene, in a temperature range of from –20° C. to 140° C., preferably of from 0° C. to 110° C., and at atmospheric pressure.

The reaction of the compounds of the general formulae (X) and (XI) is generally carried out under the following conditions:

Solvents which are suitable for all processes are ethers, such as diethyl ether, dioxane, tetrahydrofuran, glycol dimethylether, or hydrocarbons, such as benzene, toluene, xylene, hexane, cyclohexane or petroleum fractions, or halogenated hydrocarbons, such as dichloromethane, trichloromethane, carbon tetrachloride, dichloroethylene, trichloroethylene or chlorobenzene, or ethyl acetate, or triethylamine, pyridine, dimethylsulphoxide, dimethylformamide, hexamethylphosphoric triamide, acetonitrile, acetone or nitromethane. It is also possible to employ mixtures of the abovementioned solvents. Preference is given to dichloromethane.

Suitable bases for the individual steps are the customary strongly basic compounds. These preferably include organolithium compounds, such as, for example, n-butyllithium, sec-butyllithium, tert-butyllithium or phenyllithium, or amides, such as, for example, lithium diisopropylamide, sodium amide or potassium amide, or lithium hexamethylsilylamide, or alkali metal hydrides, such as sodium hydride or potassium hydride. Particular preference is given to using n-butyllithium, sodium hydride or lithium diisopropylamide.

The base is employed in an amount of from 0.1 mol to 10 mol, preferably of from 1 mol to 5 mol, in each case based on 1 mol of the starting material.

The reaction is generally carried out in a temperature range of from –10° C. to +10° C., preferably of from 5° C. to 10° C. and at atmospheric pressure.

The following conditions are suitable for carrying out the process of [D]:

The reaction of the compounds of the formulae (X), (XI) and (XIII) to give compounds of the formula (XV) can be carried out without isolation of the intermediates (XII) and (XIV). Suitable reaction temperatures are between room temperature and –20° C. Preferred metal or semi-metal reagents are titanium reagents, for example mixtures of titanium tetrachloride and titanium tetra-iso-propoxide, in particular in the molar ratio 3:1. Suitable solvents are the customary inert solvents, in particular dichloromethane.

The elimination to give the compounds of the formula (XVI) usually leads to a mixture of the different possible double-bond isomers. The elimination proceeds under the customary conditions, and is preferably carried out using thionyl chloride in pyridine at temperatures in the range of from –25 to +25° C., preferably of from –10 to +10° C.

Starting from the mixture of double-bond isomers obtained in the previous step, the halogenation to give compounds of the formula (XVII) again leads to a mixture of isomers with respect to the position of the halogen substituents and the double or single bond. Customary reagents are employed for the halogenation, preferably for allylic halogenation, and a radical initiator is employed, if appropriate. Preferred for this purpose are, for example, N-chlorosuccinimide, bromo- or N-bromosuccinimide and N-bromoacetamide. Suitable solvents are the customary inert solvents, in particular dichloromethane.

The subsequent elimination and oxidation to give the aromatic can be carried out without isolation of the intermediates, in one of the abovementioned ethers, preferably dioxane, at temperatures of from 0° C. to 150° C., preferably of from room temperature to 120° C.

For the aromatization, if appropriate, mild oxidizing agents, such as elemental sulphur of preferably chalcones, are employed. Chalcones are α,β-unsaturated ketones of the type $C_6H_5$—CO—CH=CH—$C_6H_5$. The terminal phenyl radicals may in each case carry one or more substituents, selected from the group consisting of halogen, trifluoromethyl, straight-chain or branched alkyl having up to 4 carbon atoms. Preference is given, for example, to using the chalcone 4—$CF_3$-$C_6H_4$-CO—CH=CH—$C_6H_4$—4—F.

The subsequent reduction of the keto group is carried out regio- and enantio-selectively, for example using a borane/diethylaniline complex with addition of a chiral aminoalcohol, such as 1-aminoindan-2-ol, in anhydrous ethers, in particular THF, under protective gas at temperatures of from −70° C. to 50° C.

The hydroxyl group that is formed is protected by a trialkylsilyl group, for example by the tert-butyldimethylsilyl group. The introduction is carried out via the customary active silyl derivates, for example the chlorides or the trifluoromethanesulphonate (triflates), in the presence of sterically hindered bases, such as, for example, lutidine, at temperatures of from −20° C. to 0° C. in inert solvents, such as toluene, under an atmosphere of protective gas.

The second keto function can be reduced by customary methods, for example using lithium aluminium hydride in ethers, in particular in THF, at temperatures of from 0° C. to 50° C. The desired diastereomer can be isolated from the resulting mixture of diastereomers, for example, by chromatography.

Details of the other possible reactions of the compounds of the formula (XXIII), such as, for example, removal of the silyl protective groups or introduction of a fluoro substituent into the substituent D, are given elsewhere.

The compounds of the general formula (II) are novel and can be prepared, for example, by converting compounds of the general formula (XXV)

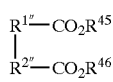
(XXV)

in which
    $R^{1''}$ and $R^{2''}$ each represent a straight-chain or branched alkylene chain having up to 7 carbon atoms,
    and
    $R^{45}$ and $R^{46}$ are identical or different and each represents straight-chain or branched alkyl having up to 4 carbon atoms,
    by 2-fold reaction according to the literature [M. Yamagushi et al., J. Org. Chem. 55, p. 1611–1623, 1990; cf. also, for example, M. Yamagushi, Tetrahedron Lett. 27, 21, 1986, 2401–2404] with compounds of the general formula (XXVI)

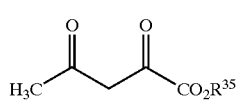
(XXVI)

in which
    $R^{35}$ is as defined above,
into the compounds of the general formula (XXVII)

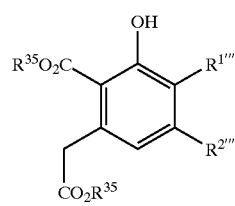
(XXVII)

in which
    $R^{35}$ is as defined above
    and
    $R^{1'''}$ and $R^{2'''}$ have the meanings of $R^{1''}$ and $R^{2''}$ given above, where the alkylene chain is substituted by a carbonyl group,
and subsequently converting these by action of $Tf_2O$/pyridine and reaction in a further step with compounds of the general formula (XXVIII)

(XXVIII)

in which
    A is as defined above,
in inert solvents and in the presence of a palladium complex into the compounds of the general formula (XXIX)

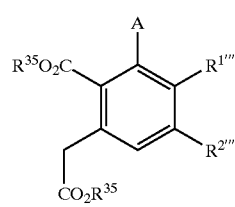
(XXIX)

in which
    $R^{35}$, $R^{1'''}$ and $R^{2'''}$ are each as defined above,
reducing the carbonyl function to give the hydroxyl function, blocking this by reaction with TBSOTf and subsequently carrying out an alkylation with compounds of the general formula (XXX)

(XXX)

in which
    E''' has the scope of meanings of E' and E'' given above.
The introduction of substituent A is generally carried out in 2 steps, initially reacting with $Tf_2O$ in pyridine. The reaction with the compounds of the general formula (XXVIII) is carried out in a further step.

Solvents which are suitable for all processes are ethers, such as diethyl ether, dioxane, tetrahydrofuran, glycol dimethyl ether, or hydrocarbons such as benzene, toluene, xylene, hexane, cyclohexane or petroleum fractions, or halogenated hydrocarbons, such as dichloromethane, trichloromethane, carbon tetrachloride, dichloroethylene, trichloroethylene or chlorobenzene, or ethyl acetate, or triethylamine, pyridine, dimethyl sulphoxide, dimethylformamide, hexamethylphosphoric triamide, acetonitrile, acetone or nitromethane. It is also possible to employ mixtures of the abovementioned solvents. Preference is given to dioxane.

Suitable palladium compounds in the context of the present invention are generally PdCl$_2$((C$_6$H$_5$)$_3$)$_2$, palladium-bis-dibenzylideneacetone (Pd(dba)$_2$), [1,1'-bis-(diphenylphosphino)ferrocene]-palladium(II) chloride (Pd(dppf)Cl$_2$) or Pd(P(C$_6$H$_5$)$_3$)$_4$. Preference is given to Pd(P(C$_6$H$_5$)$_3$)$_4$.

The reaction is generally carried out in a temperature range of from room temperature to +150° C., preferably of from +40° C. to +110° C.

The reaction is generally carried out at atmospheric pressure. However, it is also possible to carry out the process at reduced pressure or at elevated pressure (for example in the range of from 0.5 to 5 bar).

The reduction of the compounds of the general formula (XIV) is generally carried out in one of the abovementioned solvents, preferably using DIBAH.

The reductions are generally carried out using reducing agents, preferably those which are suitable for the reduction of ketones to give hydroxyl compounds. Particularly suitable in this context is the reduction using metal hydrides or complex metal hydrides in inert solvents, if appropriate in the presence of a trialkylborohydride. The reduction is preferably carried out using complex metal hydrides, such as, for example, lithium borohydride, sodium borohydride, potassium borohydride, zinc borohydride, lithium-trialkylborohydride, diisobutylaluminium hydride or lithium aluminium hydride. Very particularly preferably, the reduction is carried out using diisobutylaluminium hydride and sodium borohydride.

The reducing agent is generally employed in an amount of from 1 mol to 6 mol, preferably of from 1 mol to 4 mol, based on 1 mol of the compounds to be reduced.

The reduction generally proceeds in a temperature range of from −78° C. to +50° C., preferably of from −78° C. to 0° C. in the case of DIBAH, of from 0° C. to room temperature in the case of NaBH$_4$, particularly preferably at −78° C., in each case depending on the choice of the reducing agent and the solvent.

The reduction generally proceeds at atmospheric pressure, but is also possible to carry out the reduction at elevated or reduced pressure.

The subsequent introduction of the TBS group is carried out in one of the abovementioned solvents, preferably using toluene, in a temperature range of from −30° C. to room temperature, preferably of from −20° C. to 0° C., and at atmospheric pressure.

The alkylation with alkyl halides is generally carried out in inert solvents in the presence of a base.

Solvents which are suitable for this purpose are, depending on the nature of the alkylating agent, all inert organic solvents. These preferably include ethers, such as diethyl ether, dioxane or tetrahydrofuran, or hydrocarbons, such as benzene, toluene or xylene, or dimethylformamide or hexamethylphosphoric triamide, or mixtures of the abovementioned solvents.

Bases which are suitable for the alkylation are the customary basic compounds. These preferably include alkali metal hydrides, such as sodium hydride, alkali metal amides, such as sodium amide or lithium diisopropylamide, alkali metal alkoxides, such as sodium methoxide, sodium ethoxide, potassium methoxide, potassium ethoxide or potassium tert-butoxide, or organic amines, such as trialkylamines, for example triethylamine, or organolithium compounds, such as butyllithium or phenyllithium. Preference is given to lithium diisopropylamide.

The alkylation is generally carried out in a temperature range of from −70° C. to +80° C., preferably of from −70° C. to 0° C.

The alkylation is generally carried out at atmospheric pressure. However, it is also possible to carry out the process at reduced pressure or elevated pressure (for example in the range of from 0.5 to 5 bar).

The compounds of the general formulae (III), (XXV), (XXVI), (XXVII), (XXVIII) and (XXX) are known per se or can be prepared by customary methods.

The compounds of the general formula (XXIX) are novel and can be prepared as described above.

The compounds of the general formula (IV) are novel and can be prepared as described above.

The compounds of the general formula (VIII) are novel and can be prepared as described above.

The compounds of the general formula (VI) are novel and can be prepared by reacting compounds of the general formula (Va)

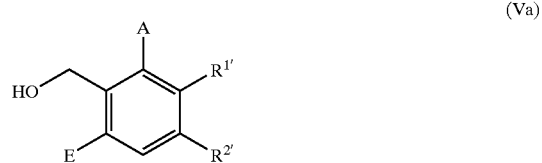

(Va)

in which

A, E, R$^{1'}$ and R$^{2'}$ are each as defined above, under an atmosphere of protective gas in inert solvents with one of the abovementioned oxidizing agents in the presence of a base, preferably using the SO$_3$/pyridine complex.

Solvents which are suitable for the individual steps are ethers, such as diethyl ether, dioxane, tetrahydrofuran, glycol dimethyl ether, diisopropyl ether or hydrocarbons, such as benzene, toluene, xylene, hexane, cyclohexane or petroleum fractions, or halogenated hydrocarbons, such as dichloromethane, trichloromethane, carbon tetrachloride, dichloroethylene, trichloroethylene or chlorobenzene. It is also possible to employ mixtures of the abovementioned solvents.

The oxidizing agent is employed in an amount of from 1 mol to 10 mol, preferably of from 2 mol to 5 mol, based on 1 mol of the compounds of the general formula (Va).

The bases which are suitable for the individual steps are the customary basic compounds. These preferably include pyridine or organolithium compounds, such as, for example, n-butyllithium, sec-butyllithium, tert-butyllithium or phenyllithium, or amides, such as, for example, lithium diisopropylamide, sodium amide or potassium amide, or lithium hexamethylsilylamide, or alkali metal hydrides, such as sodium hydride or potassium hydride. Particular preference is given to using pyridine.

The base is employed in an amount of from 1 mol to 10 mol, preferably from 2 mol to 5 mol, based on 1 mol of the compounds of the general formula (Va).

The oxidation generally proceeds at a temperature of from −50° C. to +100° C., preferably of from 0° C. to room temperature.

The compounds of the general formulae (V), (VIII) and (IX) are novel and can be prepared by converting compounds of the general formula (XXXI)

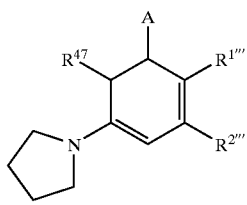
(XXXI)

in which
A, $R^{1'''}$ and $R^{2'''}$ are each as defined above,
and
$R^{47}$ either represents the radical of the formula

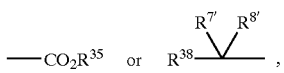

in which $R^{35}$, $R^{38}$, $R^{7'}$ and $R^{8'}$ are each as defined above,
initially by acid hydrolysis with aqueous citric acid solution into the compounds of the general formula (XXXII)

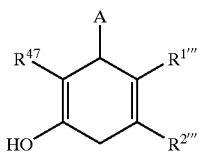
(XXXII)

in which
A, $R^{1'''}, R^{2'''}$ and $R^{47}$ are each as defined above,
subsequently carrying out an oxidation in inert solvents to give the compounds of the general formula (XXXIII)

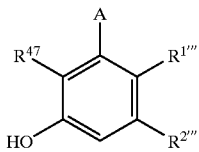
(XXXIII)

in which
A, $R^{1'''}, R^{2'''}$ and $R^{47}$ are each as defined above,
preparing, in a further step, the compounds of the general formula (XXXIV)

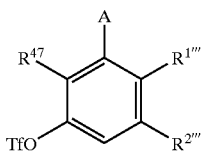
(XXXIV)

in which
A, $R^{1'''}$, $R^{2'''}$ and $R^{47}$ are each as defined above,
by reaction with trifluoromethanesulphonic anhydride in pyridine, followed by reaction with compounds of the general formula (XXXV)

$E^{IV}$ (XXXV)

in which
$E^{IV}$ represents cycloalkenyl having 3 to 8 carbon atoms, or represents straight-chain or branched alkenyl having up to 8 carbon atoms, or represents a radical of the formula $-R^{48}-Sn(R^{49}R^{50}R^{51})$,
in which
$R^{48}$ represents straight-chain or branched alkenyl having up to 8 carbon atoms,
$R^{49}$, $R^{50}$ and $R^{51}$ are identical or different and each represents straight-chain or branched alkyl having up to 8 carbon atoms,
in the system $Pd(dba)_2$/1,2-bis(diphenylphosphino)ethane, $Pd(PPh_3)_4$, $PdCl_2(PPh_3)_2$ and LiCl in the presence of an inert solvent and a base under elevated pressure and an atmosphere of protected gas to give the compounds of the general formula (XXXVI)

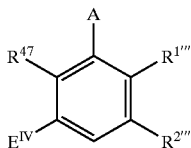
(XXXVI)

in which
A, $E^{IV}$, $R^{1'''}, R^{2'''}$ and $R^{47}$ are each as defined above,
carrying out a hydrogenation in the presence of a catalyst to give the compounds of the general formula (XXXVII)

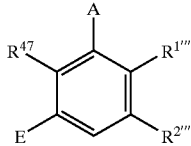
(XXXVII)

in which
A, E, $R^{1'''}, R^{2'''}$ and $R^{47}$ are each as defined above,
carrying out, in a further step, the selective reduction of the carbonyl group ($R^{1''}/R^{2''}$) in ethers to give the compounds of the general formula (XXXVIII)

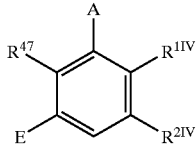
(XXXVIII)

in which
A, E and $R^{47}$ are each as defined above
and
$R^{1IV}$ and $R^{2IV}$ each have the meaning of $R^{1'}$ and $R^{2'}$ given above, the alkylene chain being substituted by hydroxyl,
and subsequently converting these by protection of the free hydroxyl function with tert-butyldimethylsilyl triflate (TBS) in inert solvents into the compounds of the general formula (XXXIX)

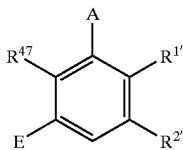
(XXXIX)

in which

A, E, $R^{1'}$, $R^{2'}$ and $R^{47}$ are each as defined above, and, in the case $R^{38}=CO_2R^{35}$, selectively reducing the alkoxycarbonyl function by customary methods to give the hydroxymethyl function.

The reaction of the compounds of the general formula (XVI) is carried out using aqueous solutions of customary acids at a temperature of from 0° C. to 150° C., preferably using carboxylic acids, such as citric acid and oxalic acid, at 60° C. and at atmospheric pressure.

The oxidation to give the compounds of the general formula (XXXIII) is, in the context of the present invention, carried out under the following conditions: Solvents which are suitable for the oxidation are ethers, such as diethyl ether, dioxane, tetrahydrofuran, glycol dimethyl ether, or hydrocarbons, such as benzene, toluene, xylene, hexane, cyclohexane or petroleum fractions, or halogenated hydrocarbons, such as dichloromethane, trichloromethane, carbon tetrachloride, dichloroethylene, trichloroethylene or chlorobenzene, or ethyl acetate, or triethylamine, pyridine, dimethylsulphoxide, dimethylformamide, hexamethylphosphoric triamide, acetonitrile, acetone or nitromethane. It is also possible to employ mixtures of the abovementioned solvents. Preference is given to toluene.

Suitable oxidizing agents are, for example, cerium(IV) ammoniumnitrate, 2,3-dichloro-5,6-dicyano-benzoquinone, pyridinium chlorochromate (PCC), pyridinium chlorochromate on basic alumina, osmium tetroxide, sodium acetate/iodine and manganese dioxide. Preference is given to 2,3-dichloro-5,6-dicyano-benzoquinone.

The oxidizing agent is employed in an amount of from 1 mol to 10 mol, preferably of from 2 mol to 5 mol, based on 1 mol of the compounds of the general formula (XXXIII).

The oxidation generally proceeds in a temperature range of from 0° C. to +100° C., preferably of from room temperature to 80° C.

The oxidation generally proceeds at atmospheric pressure. However, it is also possible to carry out the oxidation at elevated or reduced pressure.

The hydroxyl protective group trifluoromethanesulphonyl is generally introduced into the compounds of the general formula (XXXIII) in pyridine using trifluoromethanesulphonic anhydride in a temperature range of from −30° C. to +40° C., preferably of from −20° C. to 0° C., and at atmospheric pressure.

The reaction with the compounds of the general formula (XXXV) is carried out in the case of the olefins in a Heck reaction in an autoclave using a phosphino and palladium complex, in the presence of an inert solvent and a base under an atmosphere of nitrogen, in a temperature range of from +80° C. to +120° C., preferably at 100° C., or, in the case of the alkenylstannyl compounds, at from room temperature to 100° C.

Suitable solvents are the abovementioned cyclic hydrocarbons and ethers, and preference is given to toluene and dioxane.

Suitable bases are the abovementioned dialkylamines, preferably ethyldiisopropylamine.

The base is generally employed in an amount of from 0.5 mol to 5 mol, preferably of from 1 mol to 3 mol, based on 1 mol of the compounds of the general formula (XXXV).

Suitable palladium compounds in the context of the present invention are generally $PdCl_2((C_6H_5)_3)_2$, palladium-bis-dibenzylideneacetone $(Pd(dba)_2)$, [1,1'-bis-(diphenylphosphino)ferrocene]-palladium(II)chloride $(Pd(dppf)Cl_2)$, $Pd(P(C_6H_5)_3)_4$, $Pd(PPh_3)_3$, $Pd(Oac)_2$, if appropriate with addition of phosphineligands (for example dppe, diphos, dba, chiraphor, etc.)

The reduction of the double bond in the radical E''' is generally carried out by hydrogenation.

The hydrogenation is carried out by customary methods using hydrogen in the presence of noble metal catalysts, such as, for example Pd/C, Pt/C or Raney nickel, in one of the abovementioned solvents, preferably in alcohols, such as, for example, methanol, ethanol or propanol, in a temperature range of from −20° C. to +100° C., preferably of from 0° C. to +50° C., at atmospheric pressure or superatmospheric pressure.

The reduction to give the compounds of the general formula (XXXVIII) is generally carried out in one of the abovementioned ethers, preferably in tetrahydrofuran, in a temperature range of from 0° C. to +40° C., preferably of from 0° C. to room temperature, and at atmospheric pressure.

Suitable reducing agents are generally aluminium hydrides, such as $LiAlH_4$, DIBAH, Red-Al; boron hydrides, such as $NaBH_4$, $NaCNBH_3$, $LiBH_4$; borane complexes, such as $BH_3 \times THF$, $BH_3 \times DMS$, $BH_3 \times (Et_2)NC_6H_5$ or borane-dimethyl sulphide solution in tetrahydrofuran. Preference is given to borane-dimethyl sulphide solution in tetrahydrofuran. For stereoselective reductions, the borane complexes can be combined with chiral auxiliaries, such as chiral amino alcohols; preference is given here to chiral aminoindanol, for example 1R,2S-aminoindanol.

The TBS group for blocking the hydroxyl function is generally introduced in toluene using tert-butyl-dimethylsilyl triflate and a base, preferably 2,6-lutidine, in a temperature range of from −30° C. to +10° C., preferably of from −20° C. to 0° C. and at atmospheric pressure.

The reduction of the compounds of the general formula (XXXIX) is generally carried out in ether, THF or in one of the abovementioned cyclic hydrocarbons, preferably in toluene, in a temperature range of from −78° C. to −20° C., preferably of from −78° C. to −40° C., and at atmospheric pressure.

The reductions are generally carried out using reducing agents, preferably those which are suitable for the reduction of ketones to hydroxyl compounds. Particularly suitable here is the reduction using metal hydrides or complex metal hydrides in inert solvents, if appropriate in the presence of a trialkylborane. The reduction is preferably carried out using complex metal hydrides, such as, for example, lithium borohydride; sodium borohydride, potassium borohydride, zinc borohydride, lithium trialkylborohydride, diisobutylaluminium hydride or lithium aluminium hydride. Very particularly preferably, the reduction is carried out using diisobutylaluminium hydride and sodium borohydride.

The reducing agent is generally employed in an amount of from 1 mol to 6 mol, preferably of from 1 mol to 4 mol, based on 1 mol of the compounds to be reduced.

The reduction is generally carried out in a temperature range of from −78° C. to +50° C., preferably of from −78° C. to 0° C. in the case of DIBAH, of from 0° C. to room temperature in the case of $NaBH_4$, particularly preferably at −78° C., in each case depending on the choice of the reducing agent and the solvent.

The reduction generally proceeds at atmospheric pressure, but it is also possible to carry out the reaction under elevated or reduced pressure.

The compounds of the general formulae (XXXI), (XXXII), (XXXIII), (XXXIV), (XXXVI), (XXXVII), (XXXVIII) and (XXXIX) are novel and can be prepared as described above.

The compounds of the general formula (XXXV) are known.

The compounds of the general formula (XXXI) are novel and can be prepared by reacting dimedone with compounds of the general formula (XL)

A—CHO   (XL)

in which
A is as defined above
and compounds of the general formula (XLI)

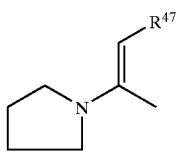   (XLI)

in which
R$^{47}$ is as defined above,
in saturated cyclic hydrocarbons, preferably cyclohexane, under reflux and at atmospheric pressure.

The compounds of the general formulae (XL) and (XLI) are known or can be prepared by customary methods.

The compounds of the general formula (X) can be prepared similarly to the process which is described below by way of example for the compound spiro[2,5]non-7-en-3-one.

Starting from cyclobutyl-dimedone(spiro[3,5]nonane-6,8-dione) of the formula (XLII)

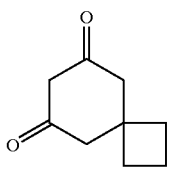   (XLII)

reaction with p-toluenesulphonic acid (PTA) in toluene and isobutanol and subsequent reduction with Red-Al in toluene gives the compound spiro[2,5]non-7-en-3-one of the formula (XLIII)

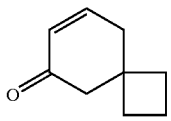   (XLIII)

The reaction with PTA/isobutanol is carried out with azeotropic distillation.

The reaction is carried out in a temperature range of from 0° C. to 60° C., preferably of from 20° C. to 50° C. Both reaction steps are carried out at atmospheric pressure.

The reaction can pass through the following intermediate stages:

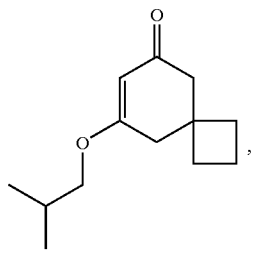   (XLIII)

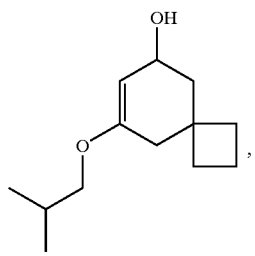   (XLIV)

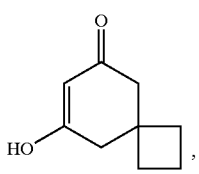   (XLV)

The preparation of the compound of the formula (XLII) is carried out by initially preparing, by reaction of cyclobutanone with triphenylphosphoranylidene-2-propanone and benzoic acid, the compound cyclobutylidene-2-propanone of the formula (XLVI)

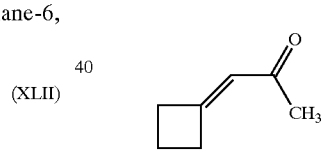   (XLVI)

and finally reacting with dimethyl malonate or diethyl malonate, if appropriate via the sequence of non-isolated intermediates of the formulae

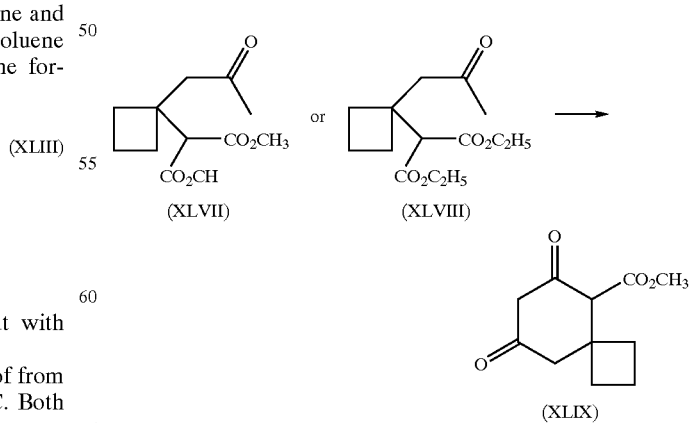

(XLVII)   (XLVIII)

(XLIX)

or

-continued (L)

(LI)

and subsequently carrying out a decarboxylation.

The preparation of the compound of the formula (XLVI) is carried out in a temperature range of from 80° C. to 120° C. and at atmospheric pressure.

The reaction with the appropriate malonic acid diesters is carried out in methanol or ethanol and at atmospheric pressure and at reflux temperature.

The preparation of the compounds of the general formula (XIII) is carried out by reacting the compounds of the formula (LII)

$$R^6 \overset{O}{\underset{\|}{-}} CH_3 \quad (LII)$$

in which

R$^6$ is as defined above and compounds of the general formula (LIII)

$$A-\overset{O}{\underset{\|}{C}}-H \quad (LIII)$$

in which

A is as defined above, in methylcyclohexane and in the presence of conc. sulphuric acid at reflux temperature and at atmospheric pressure.

The compounds of the general formulae (LII) and (LIII) are known and can be prepared by customary methods.

The compounds of the general formula (I) according to the invention have a pharmacological activity spectrum which could not have been foreseen.

The compounds of the general formula (I) according to the invention have useful pharmacological properties which are superior when compared to the prior art, in particular, they are highly effective inhibitors of the cholesterol ester transfer protein (CETP) and they stimulate the reverse cholesterol transport. The active compounds according to the invention effect a reduction of the LDL cholesterol level in the blood and simultaneously increase the HDL cholesterol level. They can therefore be used for the treatment and prevention of hypoalphalipoproteinaemia, dyslipidaemias, hypertriglyceridaemias, hyperlipidaemias or arteriosclerosis.

The pharmacological activity of the substances according to the invention was assessed using the following test:

CETP Inhibition Test

Preparation of CETP

CETP is obtained in partially purified form from human plasma by differential centrifugation and column chromatography and used for the test. For this purpose, human plasma is adjusted to a density of 1.21 g per ml using NaBr and centrifuged at 50,000 rpm at 4° C. for 18 h. The bottom fraction (d>1.21 g/ml) is applied to a Sephadex®Phenyl-Sepharose 4B (Pharmacia) column, washed with 0.15 mM NaCl/0.001 M TrisHCl pH 7.4 and subsequently eluted using dist. water. The CETP-active fractions are pooled, dialysed against 50 mM Na-acetate pH 4.5 and applied to a CM-Sepharose® (Pharmacia) column. Elution is subsequently carried out using a linear gradient (0–1 M NaCl). The pooled CETP fractions are dialysed against 10 mM TrisHCl pH 7.4 and subsequently purified further by chromatography over a Mono Q® column (Pharmacia).

Preparation of Radioactively Labelled HDL 50 ml of fresh human EDTA plasma is adjusted to a density of 1.12 using NaBr and centrifuged at 4° C. in a Ty 65 rotor at 50,000 rpm for 18 h. The upper phase is used to obtain cold LDL. The lower phase is dialysed against 3*4 l of PDB buffer (10 mM Tris/HCl pH 7.4, 0.15 mM NaCl, 1 mM EDTA, 0.02% NaN$_3$). Per 10 ml volume of retained material, 20 µl of $^3$H-cholesterol (Dupont NET-725; 1 µCi/ml, dissolved in ethanol!) are subsequently added, and the mixture is incubated at 37° C. under N$_2$ for 72 h.

The mixture is then adjusted to a density of 1.21 using NaBr and centrifuged in a Ty 65 rotor at 20° C. and 50,000 rpm for 18 h. The upper phase is collected and the lipoprotein fractions are purified by gradient centrifugation. To this end, the isolated labelled lipoprotein fraction is adjusted to a density of 1.26 using NaBr. In each case 4 ml of this solution are covered in centrifuge tubes (SW 40 rotor) with 4 ml of a solution of a density of 1.21 and 4.5 ml of a solution of 1.063 (density solutions of PDB buffer and NaBr), and the tubes are subsequently centrifuged in an SW 40 rotor at 38,000 rpm and 20° C. for 24 h. The intermediate layer which is found between a density of 1.063 and a density of 1.21 and which contains the labelled HDL is dialysed against 3*100 volume of PDB buffer at 4° C.

The retained material contains radioactively labelled $^3$H-CE-HDL, which is used for the test adjusted to approximately 5×10$^6$ cmp.

CETP Test

To assess the CETP activity, the transfer of $^3$H-cholesterol ester from human HD-lipoproteins to biotinylated LD-lipoproteins is measured.

The reaction is terminated by addition of Streptavidin-SPA® beads (Amersham) and the transferred radioactivity is directly measured in a liquid scintillation counter.

In the assay mixture, 10 µl of HDL-$^3$H-cholesterol ester (~50,000 cpm) with 10 µl of Biotin-LDL (Amersham) in 50 mM Hepes/0.15 m NaCl/0.1% bovine serum albumin/0.05% NaN$_3$ pH 7.4 are incubated with 10 µl of CETP (1 mg/ml) and 3 µl of a solution of the substance to be tested (dissolved in 10% DMSO/1% BSA) at 37° C. for 18 h. 200 µl of the SPA streptavidin bead solution (TRKQ 7005) are subsequently added, the mixture is incubated with shaking for another 1 h and subsequently measured in a scintillation counter. The controls used are corresponding incubations with 10 µl of buffer, 10 µl of CETP at 4° C. and 10 µl of CETP at 37° C.

The activity which is transferred in the control experiments with CETP at 37° C. is taken to be 100% transfer. The substance concentration at which this transfer is reduced by half is stated as the IC$_{50}$ value.

In Table A below, the IC$_{50}$ values (mol/l) for CETP inhibitors are given:

TABLE A

| Example No. | IC$_{50}$ value (nmol/l) |
|---|---|
| 25 | 3 |
| 31 | 2.7 |

Ex vivo Activity of the Compounds According to the Invention

Syrian gold hamsters, which have been bred in our own laboratory, are anaesthetized after 24 hours of fasting (0.8 mg/kg of atropine, 0.8 mg/kg of Ketavet® s.c., 30' later 50 mg/kg of nembutal i.p.). The jugular vein is subsequently exposed and cannulated. The test substance is dissolved in a suitable solvent (usually adalate placebo solution: 60 g of glycerol, 100 ml of H$_2$O, ad 1000 ml PEG-400) and administered to the animals via a PE catheter, which is introduced into the jugular vein. The same volume of solvent without test substance is administered to the control animals. The vein is subsequently tied off and the wound is closed.

The test substances can also be administered p.o. by dissolving the substances in DMSO and suspending them in 0.5% tylose and administering them using a pharyngeal tube. Identical volumes of solvent without test substance are administered to the control animals.

At different intervals—up to 24 hours after the administration—blood samples are taken from the animals by puncture of the retro-orbital venous plexus (approximately 250 µl). Coagulation is completed by incubation at 4° C. overnight, and the samples are subsequently centrifuged at 6000×g for 10 minutes. The CETP activity is determined in the resulting serum using the modified CETP test. The transfer of $^3$H-cholesterol ester from HD-lipoproteins to biotinylated LD-lipoproteins is measured as described above for the CETP test.

The reaction is terminated by addition of Streptavidin-SPA® beads (Amersham), and the transferred radioactivity is directly determined in a liquid scintillation counter.

The test protocol is carried out as described under "CETP test". However, to test the sera, 10 µl of CETP are replaced by 10 µl of the appropriate serum samples. Corresponding incubations of sera of untreated animals serve as controls.

The activity that is transferred in the control experiments using control sera is classified as 100% transfer. The substance concentration at which this transfer is reduced by half is stated as the ED$_{50}$ value.

TABLE B

| | ED$_{50}$ values for ex vivo activity | |
|---|---|---|
| Ex.-No. | ED$_{50}$ | % inhibition at 3 mg/kg |
| 25 | <0.3 mg/kg | 83.1% |
| 31 | <0.3 mg/kg | 72.3% |

In vivo Activity of the Compounds According to the Invention

In experiments for assessing the oral activity on lipoproteins and triglycerides, test substance, dissolved in DMSO and suspended in 0.5% tylose, is administered perorally by means of a pharyngeal tube to Syrian gold hamsters which have been bred in our own laboratory. To determine the CETP activity, blood samples (approximately 250 µl) are taken by retro-orbital puncture prior to the start of the experiment. The test substances are subsequently administered perorally using a pharyngeal tube. Identical volumes of solvent without test substance are administered to the control animals. Subsequently, the animals have to fast and at different intervals—up to 24 hours after the administration of the substances—blood samples are taken by puncture of the retro-orbital venous plexus.

Coagulation is completed by incubation at 4° C. overnight, and the samples are subsequently centrifuged at 6000×g for 10 minutes. The content of cholesterol and triglycerides in the resulting serum is assessed using modified commercially available enzyme tests (cholesterol enzymatic 14366 Merck, triglycerides 14364 Merck). Serum is diluted in a suitable manner with normal saline solution.

100 µl of serum dilution and 100 µl of test substance are transferred into 96-well-plates and incubated at room temperature for 10 minutes. The optical density is subsequently determined at a wavelength of 492 nm using an automatic plate reader.

The triglyceride and cholesterol concentrations of the samples are determined with the aid of a standard curve measured in parallel.

The determination of the HDL-cholesterol content is carried out after precipitation of the ApoB-containing lipoproteins using a reagent mixture (Sigma 352-4 HDL cholesterol reagent) in accordance with the instructions of the manufacturer.

TABLE C

| HDL increase in in vivo experiments | | |
|---|---|---|
| Ex. No. | Dose [mg/kg] | % HDL increase |
| 25 | 2 × 1 | +15 |
| 31 | 2 × 0.3 | +19 |

In vivo Activity in Transgenic hCETP Mice

The substances to be tested were administered to transgenic mice, which were bred in our own laboratory (Dinchuck, Hart, Gonzalez, Karmann, Schmidt, Wirak; BBA (1995), 1295, 301), via the feed. Prior to the beginning of the experiment, blood samples were taken retro-orbitally from the mice to determine cholesterol and triglycerides in the serum. The serum was obtained as described above for hamsters by incubation at 4° C. overnight and subsequent centrifugation at 6000×g. After one week, blood samples were again taken from the mice to determine lipoproteins and triglycerides. The change of the measured parameters are expressed as a change in percent based on the initial value.

TABLE D

| Ex. No. | HDL | LDL | Triglycerides |
|---|---|---|---|
| 15 (30 ppm) | +60% | −18% | −15% |

The invention furthermore relates to the combination of substituted tetrahydro-naphthalenes of the general formula (I) with a glucosidase and/or amylase inhibitor for the treatment of familial hyperlipidaemias, of obesity (adipositas) and of diabetes mellitus. Glucosidase and/or amylase inhibitors in the context of the present invention are, for example, acarbose, adiposine, voglibose, miglitol, emiglitate, MDL-25637, camiglibose (MDL-73945), tendamistate, AI-3688, trestatin, pradimicin-Q and salbostatin.

Preference is given to the combination of acarbose, miglitol, emiglitate or voglibose with one of the abovementioned compounds of the general formula (I) according to the invention.

41

Furthermore, the compounds according to the invention can be combined with cholesterol-lowering vastatines or ApoB-lowering principles, in order to treat dyslipidaemias, combined hyperlipidaemias, hypercholesterolaemias or hypertriglyceridaemias.

The abovementioned combinations can also be used for primary or secondary prevention of coronary heart diseases (for example myocardial infarction).

Vastatines in the context of the present invention are, for example, lovastatin, simvastatin, pravastatin, fluvastatin, atorvastatin and cerivastatin. ApoB-lowering agents are, for example, MTP inhibitors.

Preference is given to the combination of cerivastatin or ApoB inhibitors with one of the abovementioned compounds of the general formulae (I) and (Ia) according to the invention.

The novel active compounds can be converted in a known manner into the customary formulations, such as tablets, coated tablets, pills, granules, aerosols, syrups, emulsions, suspensions and solutions, using inert, non-toxic, pharmaceutically suitable carriers or solvents. In this case the therapeutically active compound should in each case be present in a concentration from approximately 0.5 to 90% by weight of the total mixture, i.e. in amounts which are sufficient in order to achieve the dosage range indicated.

The formulations are prepared, for example, by extending the active compound using solvents and/or carriers, if appropriate using emulsifiers and/or dispersants, it optionally being possible, for example, to use organic solvents as auxiliary solvents if the diluent used is water.

Administration is carried out in a customary manner, intravenously, orally, parenterally or perlingually, in particular orally.

In the case of parenteral administration, solutions of the active compound can be used by employing suitable liquid carrier materials.

In general, it has proved advantageous, in the case of intravenous administration, to administer amounts from approximately 0.01 to 1 mg/kg, preferably approximately 0.01 to 0.5 mg/kg, of body weight to achieve effective results, and in the case of oral administration the dosage is approximately 0.01 to 20 mg/kg, preferably 0.1 to 10 mg/kg, of body weight.

In spite of this, if appropriate it may be necessary to depart from the amounts mentioned, namely depending on the body weight or on the type of administration route, on individual reaction towards the medicament, the manner of its formulation and the time at or interval during which administration takes place. Thus, in some cases it may be adequate to manage with less than the abovementioned minimum amounts, while in other cases the upper limit mentioned has to be exceeded. In the case of the administration of relatively large amounts, it may be advisable to divide these into several individual doses over the course of the day.

42

Starting Materials

EXAMPLE I

Methyl 8-hydroxy-7-(methoxycarbonyl)-3,3-dimethyl-1-oxo-1,2,3,4-tetrahydro-6-naphthylacetate

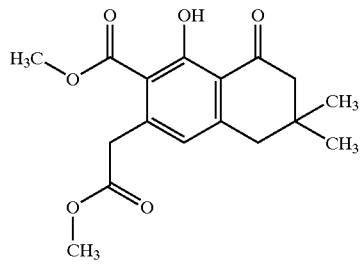

Under argon, 48.48 g of sodium hydride are initially charged in 1200 ml of THF and, with ice-cooling at 8–10° C., 139.92 g of methyl acetate dissolved in 375 ml of THF are added dropwise over a period of 35–40 min, and the mixture is then stirred in the ice-bath for 1 h. Again at 8–10° C. and over a period of 35–40 min, 761.2 ml of n-BuLi in hexane are then added dropwise, and the mixture is again stirred in the ice-bath for 1 h. 27 g of dimethyl 2-dimethylglutarate dissolved in 210 ml of THF are then added dropwise at 5–7° C. over a period of 15 min and the mixture is then stirred for 2 h, and the internal temperature is allowed to rise to room temperature (RT). For work-up, the reaction solution is transferred into a stirred mixture of 7.2 l of 10% strength ammonium chloride solution and 3.6 l of toluene and then stirred for another 10 min. The organic phase is separated off and the aqueous phase is reextracted once more with 1.8 l of toluene. The combined organic phases are washed neutral using 2 times 1.8 l of water, dried over sodium sulphate and concentrated under reduced pressure. The residue (approximately 60 g) is admixed with 30 ml of toluene, and 60 ml of petroleum ether are slowly added with stirring. The mixture is seeded with product and the product crystallizes out and is, after cooling to 10–15° C. for 1 h, filtered off with suction and dried at 50° C. under reduced pressure (fract. 1). The mother liquor was concentrated and applied to a column of 600 g of silica gel (9.5×15 cm) and eluted initially with pure toluene and later with an increasing proportion of ethyl acetate (95:5, 90:10, 80:20). The main fraction was concentrated and the residue (15 g) was mixed with 7.5 ml of toluene, and 30 ml of petroleum ether were added with stirring, causing the product to crystallize out. The new mother liquor was combined with an impure fraction from the chromatography, concentrated (10 g) and then crystallized as above using 5 ml of toluene and 45 ml of petroleum ether (fract. 3).

Yield: 24.9 g (54% of theory)

$R_f$=0.15 (Cy: EA 8:2)

EXAMPLE II

Methyl-7-(methoxycarbonyl)-3,3-dimethyl-1-oxo-1,
2,3,4-tetrahydro-8-trifluoro-methylsulphonyl-6-
naphthylacetate

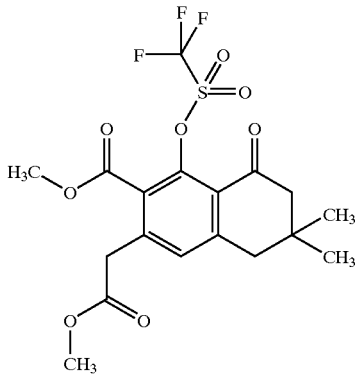

21 g of the compound of Ex. I are dissolved in 328 ml of pyridine, and 21.52 ml of trifluoromethanesulphonic anhydride are added dropwise with ice-cooling at at most 5° C. over a period of 30 min. The mixture is then stirred for 18 h, and the temperature is allowed to rise to room temperature. For work-up, the reaction solution was transferred into a stirred mixture of 1.6 l of water and 0.8 ml of toluene (pH=6) and adjusted to pH=2 by dropwise addition of 325 ml of conc. hydrochloric acid. The aqueous phase was reextracted once more using 0.4 l of toluene, and the combined organic phases were washed neutral using 0.4 l each of water, 2.5% strength sodium bicarbonate solution and 2 times water, dried over sodium sulphate and filtered through a layer of silica gel. The filtrate was concentrated under reduced pressure to approximately 100 ml and 100 ml of petroleum ether were added dropwise with stirring, causing the product to crystallize out. The mixture was cooled at 10–15° C. for 2 hours, and the product was then filtered off with suction and dried under reduced pressure at 50° C.

Yield: 16.6 g (56% of theory)

$R_f$=0.32 (Cy: EA 6:4)

EXAMPLE III

Methyl-8-(4-fluorophenyl)-7-(methoxycarbonyl)-3,
3-dimethyl-1-oxo-1,2,3,4-tetrahydro-6-
naphthylacetate

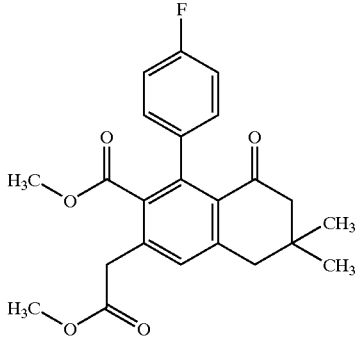

Reaction under extreme exclusion of moisture and atmospheric oxygen!

In a reaction vessel which had been heated under vacuum to remove all moisture, 16.5 g of the compound of Ex. II, 6.63 g of 4-fluorobenzeneboronic acid, 13.16 g of tripotassium phosphate and 4.76 g of tetrakis(triphenylphosphine) palladium (0) are initially charged in solid form, and the apparatus is flushed by repeated evacuation and venting with argon. The air-degassed dioxane is subsequently added, and the mixture is boiled under reflux for 12 h. After cooling, the reaction solution was filtered through a layer of silica gel (40 g), and the filtrate was concentrated under reduced pressure. The residue was dissolved in 600 ml of toluene (pH 3) and washed neutral with 200 ml each of water, 5% strength sodium bicarbonate solution and 2 times water, dried over sodium sulphate and once again filtered through a layer of silica gel. The product crystallized out after concentration to approximately 50 ml and dropwise addition of approximately 100 ml of petroleum ether with stirring, and, after cooling to 10–15° C. (1 h) was filtered off with suction and dried at 50° C. under reduced pressure (fract. 1). The last layer of silica gel was eluted once more using 200 ml each of toluene/ethyl acetate 90:10 and 80:20, and the residue which was obtained after concentration of the solution and the residue of the mother liquor from fract. 1 (2.3 g) were purified by column chromatography over 250 g of silica gel 60/0.04–0.063 mm (column 5×25 cm) using cyclohexane/ethyl acetate 80:20.

Yield: 12.8 g (87% of theory)

$R_f$=0.35 (Cy: EA 6:4)

EXAMPLE VI

Methyl-8-(4-fluorophenyl)-7-(methoxycarbonyl)-3,3
dimethyl-1 hydroxy-1,2,3,4 tetrahydro-6-
naphthylacetate

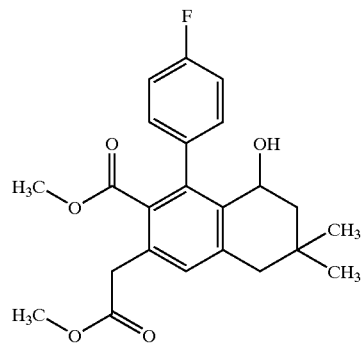

14.1 g of the compound of Ex. III are dissolved with gentle heating in methanol, and sodium hydroxide solution is added at 25° C. 5.36 g of sodium borohydride are then introduced, and the mixture is stirred at at most 30° C. with gentle water-cooling for 1.5 h until the reaction has gone to completion. The pH is subsequently adjusted to 3 by dropwise addition of 150 ml of 1N hydrochloric acid, the reaction solution is stirred for 15 minutes and then stirred into a mixture of 2.4 l of water and 1.2 l of toluene, and the aqueous phase is reextracted once more using 0.6 l of toluene. The combined organic phases were washed neutral with 0.6 l each of 5% strength sodium bicarbonate solution and 2 times with water, dried over sodium sulphate and concentrated under reduced pressure to approximately 50 ml. The product crystallizes out after dropwise addition of 100 ml of petroleum ether with stirring, and is, after cooling to 10–15° C., filtered off with suction and dried. Crystals and mother liquor were recombined and chromatographed over 870 g of silica gel 60/0.04–0.063 mm (column 6.5×52 cm) using toluene/ethyl acetate 90:10. The main fractions were concentrated under reduced pressure and finally recrystallized from toluene. The solids were dried under reduced pressure at 50° C.

Yield: 11.5 g (73% of theory)

$R_f$=0.20 (toluene: EA 9:1)

EXAMPLE V

Methyl-8-(4-fluorophenyl)-7-(methoxycarbonyl)-3,3-dimethyl-1-(tert-butyldimethylsilyloxy)-1,2,3,4-tetrahydro-6-naphthylacetate

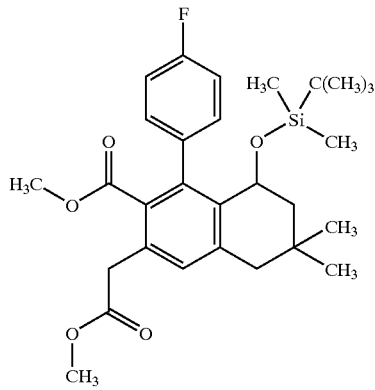

Under argon, 9.9 g of the compound of Ex. IV are dissolved in dry dichloromethane and cooled to −20° C. 7.20 ml of 2,6-lutidine are then added dropwise, followed by 7.38 ml of t-butyldimethylsilyl trifluoromethanesulphonate. The mixture is then stirred at −20 to −15° C. for 1 h until the reaction has gone to completion.

For work-up, 100 ml of sat. ammonium chloride solution were added dropwise, the mixture was stirred at room temperature for 10 min, and the phases were separated. The aqueous phase was reextracted once more using 100 ml of dichloromethane, and the combined organic phases were washed neutral using 2 times 100 ml each of water, dried over sodium sulphate and concentrated. The crude product was chromatographed over 480 g of silica gel 60/0.04–0.063 mm (column 5=50 cm) using cyclohexane/ethyl acetate 90:10.

Yield: 10.5 g (83% of theory)

$R_f$=0.48 (toluene: EA 9:1)

EXAMPLE IV

Methyl 8-(tert-butyl-dimethylsilyloxy)-1-(4-fluorophenyl)-3-(1-methoxycarbonyl-ethyl)-6,6-dimethyl-5,6,7,8-tetrahydronaphthalene-2-carboxylate

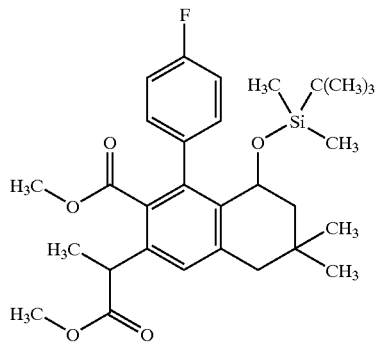

Under argon, 10.3 g of the compound of Ex. V are dissolved in 200 ml of dry THF and cooled to −70° C. 13.98 ml of 2 M LDA solution are subsequently added dropwise at at most −60° C. over a period of 30 min, the mixture is stirred for 1 h and the internal temperature is allowed to rise to −20° C. The mixture is then once more cooled to −70° C., and at at most −60° C., initially 2.12 ml of methyl iodide dissolved in 20 ml of THF are added dropwise over a period of 30 min. After a further 30 min, the reaction is checked by tlc. For work-up, the reaction solution was stirred into a mixture of 1 l of 10% strength ammonium chloride solution and 0.5 l of toluene, and the phases were separated. The aqueous phase was reextracted once more using 0.25 l of toluene, and the combined organic phases were washed neutral using 2 times 0.25 l of water each time, dried over sodium sulphate and concentrated under reduced pressure at 50° C. The crude product was chromatographed over 870 g of silica gel 60/0.04–0.063 mm (column 8×52 cm) using cyclohexane/ethyl acetate 90:10. The main fraction was concentrated under reduced pressure at 50° C. and finally crystallized from the cyclohexane after seeding. The solid was dried under reduced pressure at 50° C.

Yield: 9.4 g (85% of theory)

$R_f$=0.27 (Cy: EA 9:1)

EXAMPLE VII

Methyl 8-(tert.-butyl-dimethylsilyloxy)-1-(4-fluorophenyl)-3-(2-hydroxy-1-methyl-ethyl)-6,6-dimethyl-5,6,7,8-tetrahydronaphthalene-2-carboxylate

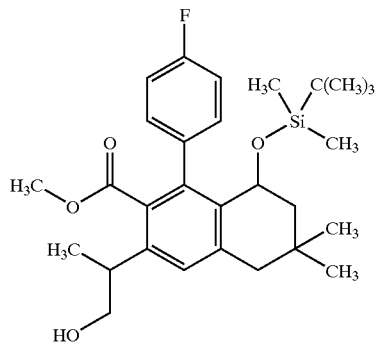

Under argon, 5.24 g of the compound of Ex. VI are initially charged dissolved in dry THF, and the mixture is cooled to −70° C. 79.26 ml of a 1-molar diisobutylaluminium hydride solution were then added dropwise at at most −65° C. over a period of 45 min, and the mixture was stirred for 90 min. 393 ml of a 20% strength potassium sodium tartrate solution were subsequently added dropwise, and the internal temperature was allowed to rise to room temperature. The mixture was stirred for 60 min and then diluted with 1050 ml of water and 525 ml of toluene, and the phases were separated. The aqueous phase was reextracted once more using 250 ml of toluene, and the combined organic phases were washed neutral using 2 times 250 ml of water each time, dried over sodium sulphate and concentrated under reduced pressure at 50° C.

Yield: 4.25 g (85% of theory)

$R_f$=0.17 (Cy: EA 8:2)

EXAMPLE VIII

Methyl 8-(tert-butyl-dimethylsilyloxy)-1-(4-fluorophenyl)-6,6-dimethyl-3-(2-methyl-sulphonyloxy-1-methyl-ethyl)-5,6,7,8-tetrahydronaphthalene-2-carboxylate

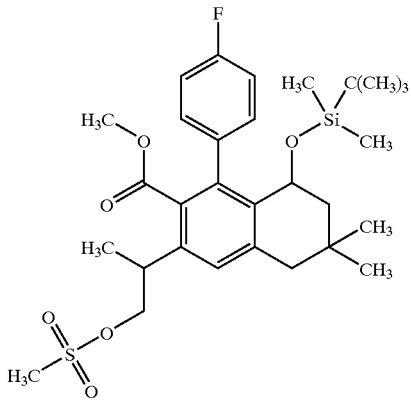

Under argon, 4.25 g of the compound of Ex. VII are dissolved in diethyl ether, 3.29 ml of triethylamine are added and the mixture is cooled to −20° C. 1.71 ml of mesyl chloride are then added dropwise at −25 to −20° C. over a period of 30 min, and the mixture is then stirred at the same temperature for 3 h. 31 ml of sat. ammonium chloride solution are then added dropwise, and the reaction mixture is allowed to warm to room temperature (pH 4). The phases are then separated and the aqueous phase is reextracted once more using 31 ml of ether. The combined organic phases were washed with 31 ml each of water, 1% strength sodium bicarbonate solution (pH 8) and 2 times with water, dried over sodium sulphate and concentrated under reduced pressure at 50° C.

Yield: 4.77 g (85% of theory)

$R_f$=0.28 (Cy: EA 8:2)

EXAMPLE IX

Methyl 8-(tert-butyldimethylsilyloxy)-1-(4-fluorophenyl)-3-isopropyl-6,6-dimethyl-5,6,7,8-tetrahydronaphthalene-2-carboxylate

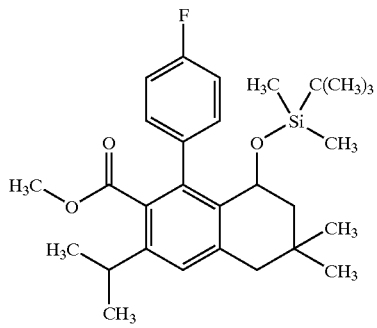

Under argon, 4.7 g of the compound of Ex. VIII are dissolved in 69 ml of DMSO, and 0.78 g of sodium borohydride are subsequently added. The mixture is then stirred at 85° C. for 5 h until most of the starting material has reacted.

For work-up, the reaction solution was stirred into a mixture of 350 ml of 10% strength sodium chloride solution and 175 ml of toluene, the pH was adjusted to 5 by slow dropwise addition of approximately 14 ml of 1 M hydrochloric acid, and the phases were separated. The aqueous phase was then reextracted once more using 90 ml of toluene, and the combined organic phases were washed neutral with 90 ml each of 5% strength sodium bicarbonate solution and 2 times with water, dried over sodium sulphate and concentrated. The crude product was dissolved in a little toluene and applied to a short layer of silica gel (60 g) and eluted with toluene. The main fraction was concentrated and crystallized from a little toluene by seeding with product, and was then dried under reduced pressure until its weight remained constant.

Yield: 2.61 g (78% of theory)

$R_f$=0.30 (Cy: EA 95:5)

EXAMPLE X 8-(tert-Butyldimethylsilyloxy)-1-(4-fluorophenyl)-2-hydroxymethyl-3-isopropyl-6,6-dimethyl-5,6,7,8-tetrahydronaphthalene

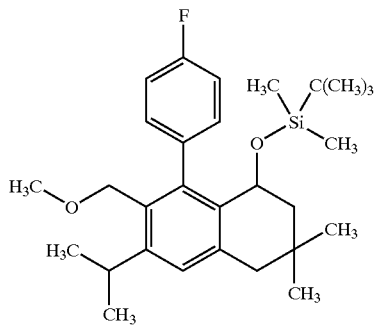

Under argon, 2.57 g of the compound of Ex. IX are dissolved in dry toluene and cooled to −70° C. 15.9 ml of a 1-molar diisobutylaluminium hydride solution are subsequently added dropwise at at most −65° C. over a period of 20 min, and the mixture is then stirred at the same temperature for 1 h. For work-up, 2.0 ml of methanol were initially carefully added dropwise and then, after the evolution of hydrogen had ceased, 158 ml of a 20% strength solution of potassium sodium tartrate, and the reaction mixture was allowed to warm to room temperature. Stirring was continued for 30 min, the phases were separated and the aqueous phase was reextracted once more with 30 ml of toluene. The combined organic phases were washed neutral using 2 times 30 ml of water, dried over sodium sulphate and concentrated at 50° C. under reduced pressure, causing the product to crystallize. The solid was dried at 50° C. under reduced pressure until its weight remained constant.

Yield: 2.30 g (82% of theory)

$R_f$=0.25 (Cy: EA 9:1)

EXAMPLE XI 8-(tert-Butyldimethylsilyloxy)-1-(4-fluorophenyl)-3-isopropyl-6,6-dimethyl-5,6,7,8-tetrahydronaphthalene-2-carbaldehyde

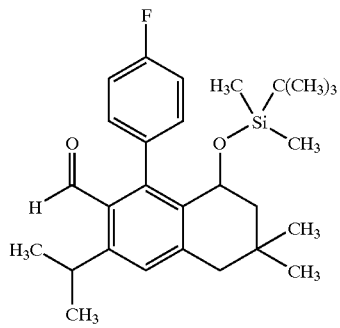

Under argon, 2.32 g of the compound of Ex. X are dissolved in dichloromethane, 6.13 ml of DMSO and 3.52 ml of triethylamine are added, and the mixture is cooled to 5° C. 3.23 g of sulphur trioxide/pyridine complex are then added at 5–10° C. in small portions over a period of 10 min, and the mixture is stirred for 1 h. For work-up, 12 ml of water are stirred into the mixture and the phases are separated. The organic phase is subsequently washed 2 times with 12 ml of water each time, dried over sodium sulphate and concentrated under reduced pressure at 50° C. to approximately 3 ml. The product crystallizes out by scratching and cooling, and the crystal pulp is now completely concentrated and dried under reduced pressure (0.2 mb) at room temperature until the weight remains constant.

Yield: 2.28 g (79% of theory)

$R_f$=0.57 (Cy: EA 9:1)

EXAMPLE XII

Methyl 1-(4-fluoro-phenyl)-6,6-dimethyl-8-oxo-3-pyrrolidine-1-yl-1,2,5,6,7,8-hexa-hydronaphthalene-2-carboxylate

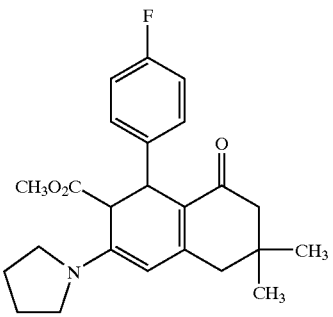

A solution of 1.69 g (10 mmol) of methyl 3-pyrrolidine-1-yl-but-2-enoate, 1.40 g (10 mmol) of dimedone and 1.24 g (10 mmol) of 4-fluorobenzaldehyde in 30 ml of cyclohexane is refluxed on a water separator overnight. The mixture is cooled, the solvent is removed under reduced pressure and the residue is purified over silica gel 60 (elution with EtOAc/toluene 1:4).

Yield: 0.90 g (23%)

Rf=0.38 (EtOAc/toluene 1:4).

EXAMPLE XIII

Methyl 1-(4-fluoro-phenyl)-3-hydroxy-6,6-dimethyl-8-oxo-1,4,5,6,7,8-hexahydro-naphthalene-2-carboxylate

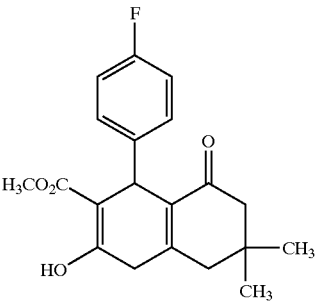

A suspension of 13.0 g (32.7 mmol) of the compound of Example XII in 1100 ml of a sat. solution of citric acid is stirred at 60° C. for 16 h. The mixture is allowed to cool and extracted with ethyl acetate (3×600 ml). The combined organic phases are washed with sat. NaCl solution and dried over $Na_2SO_4$, giving a yellow residue which is purified by flash filtration over 450 g silica gel 60 using EtOAc/cyclohexane 1:20 to 20:1.

Yield: 8.97 g (80%)

$R_f$=0.32 (EtOAc/petroleum ether 1:5).

EXAMPLE XIV

Methyl 1-(4-fluoro-phenyl)-3-hydroxy-6,6-dimethyl-8-oxo-5,6,7,8-tetrahydro-naphthalene-2-carboxylate

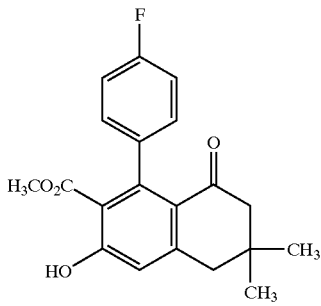

A solution of 4.0 g (11.6 mmol) of the compound of Example XIII and 13.2 g (58.1 mmol) of DDQ in 400 ml of toluene is stirred at 80° C. for 24 h. The mixture is filtered through diatomaceous earth and the diatomaceous earth is rinsed with toluene. The filtrate is concentrated under reduced pressure and the residue is chromatographed over 300 g of silica gel 60 ($CH_2Cl_2$).

Yield: 2.62 g (64%)

$R_f$=0.35 ($CH_2Cl_2$)

EXAMPLE XV

Methyl 1-(4-fluoro-phenyl)-6,6-dimethyl-8-oxo-3-trifluoromethanesulphonyloxy-5,6,7,8-tetrahydro-naphthalene-2-carboxylate

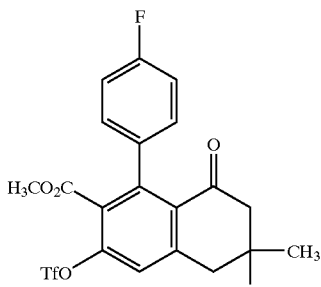

Tf = trifluoromethanesulphonyloxy

At 0° C., 4.66 g (16.5 mmol) of trifluoromethanesulphonic anhydride are added dropwise over a period of 5 minutes to a solution of 3.14 g (9.17 mmol) of the compound of Example XIV in 20 ml of pyridine. The mixture is allowed to warm to room temperature and stirred at this temperature for 16 h. The reaction mixture is poured into ice-water and extracted with EtOAc (3×). The combined organic phases are dried over $Na_2SO_4$, concentrated under reduced pressure and purified over 500 g of silica gel 60 ($CH_2Cl_2$).

Yield: 3.43 g (79%)

$R_f$=0.50 ($CH_2Cl_2$).

EXAMPLE XVI

Methyl 3-cyclopent-2-enyl-1-(4-fluoro-phenyl)-6,6-dimethyl-8-oxo-5,6,7,8-tetrahydro-naphthalene-2-carboxylate

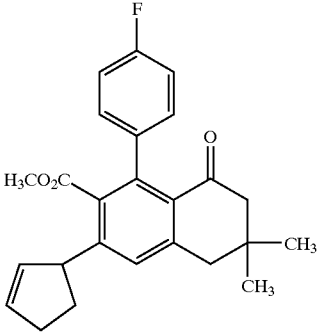

In a sealed autoclave, a mixture of 3.43 g (7.22 mmol) of the compound of Example XV, 1.24 g (2.16 mmol) of Pd(dba)$_2$, 1.29 g (3.24 mmol) of 1,2-bis-(diphenylphosphino)-ethane, 2.5 ml of ethyldiisopropylamine, 6.4 ml of cyclopentene and 65 ml of dry toluene is heated under an atmosphere of nitrogen at 100° C. for 16 h. The mixture is filtered through a glass frit using a mixture of 5 g of silica gel 60 and 5 g of diatomaceous earth, and the filtrate is concentrated. The crude product is chromatographed over 500 g of silica gel (elution with $CH_2Cl_2$).

Yield: 1.48 g (52%)

$R_f$=0.36 ($CH_2Cl_2$).

EXAMPLE XVII

Methyl 3-cyclopentyl-1-(4-fluoro-phenyl)-6,6-dimethyl-8-oxo-5,6,7,8-tetrahydro-naphthalene-2-carboxylate

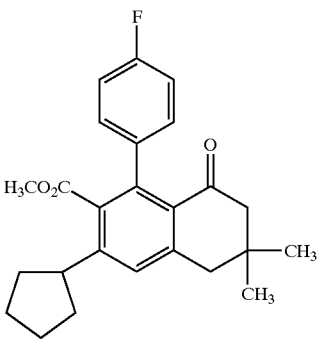

A mixture of 1.17 g (2.98 mmol) of the compound of Example XVI and 150 mg of Pd/C (10%) in 80 ml of EtOAc is hydrogenated under an atmosphere of hydrogen (1 atm) for 5 h. The mixture is filtered through diatomaceous earth, concentrated and purified over silica gel 60 (EtOAc/petroleum ether 1:10).

Yield: 1.01 g (86%)

$R_f$=0.23 (EtOAc/petroleum ether 1:10).

EXAMPLE XVIII

Methyl (8S)-3-cyclopentyl-1-(4-fluoro-phenyl)-8-hydroxy-6,6-dimethyl-5,6,7,8-tetrahydro-naphthalene-2-carboxylate

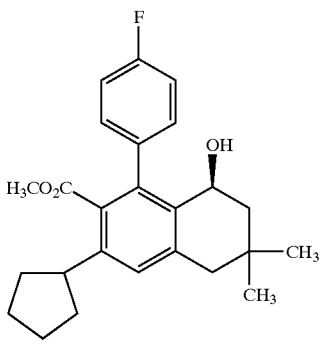

1.75 ml (3.5 mmol) of a 2.0 M solution of borane/dimethyl sulphide in THF is added dropwise to a solution of 59 mg (0.40 mmol) of (1R,2S)-aminoindanol in 8 ml of dry THF, and the mixture is stirred for 1 h at room temperature. A solution of 783 mg (1.98 mmol) of the compound of Example XVII in 16 ml of dry THF is slowly added dropwise at 0–5° C. After 5 minutes, the mixture is allowed to warm to room temperature and stirred for another 1 h. At 0° C., the reaction is quenched by addition of 1.5 ml of methanol, the reaction mixture is admixed with water and extracted with toluene. The combined organic phases are washed with sat. NaCl solution, dried with $Na_2SO_4$ and concentrated. The crude product is chromatographed over 75 g of silica gel 60 (elution: EtOAc/petroleum ether/triethylamine 1:10:0.1).

Yield: 769 mg (97%), ee=89.7% (Chiralcel AD, heptane/ethanol 90:10)

$R_f$=0.33 (ether/petroleum ether 1:5).

EXAMPLE XIX

Methyl (8S)-8-(tert-butyl-dimethyl-silyloxy)-3-cyclopentyl-1-(4-fluoro-phenyl)-6,6-dimethyl-5,6,7,8-tetrahydro-naphthalene-2-carboxylate

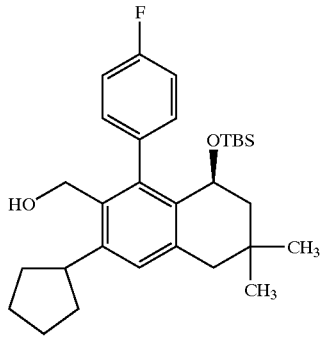

At −16° C., a solution of 1.70 g (6.43 mmol) of tert-butyl-dimethylsilyltriflate is added dropwise to a solution of 850 mg (2.14 mmol) of the compound of Example XVIII and 1.84 g (17.1 mmol) of 2,6-lutidine in 10 ml of dry toluene. The mixture is stirred at this temperature for 30 minutes and at 0° C. for a further 30 minutes. The reaction is quenched using 5 ml of water and the mixture is extracted with EtOAc. The combined organic phases are washed with sat. $NaHCO_3$ solution and sat. NaCl solution, dried over $Na_2SO_4$ and concentrated under reduced pressure. The crude product is purified over silica gel 60 (elution: EtOAc/cyclohexane/triethylamine 1:10:0.1).

Yield: 1.05 g (96%)

$R_f$=0.63 (EtOAc/petroleum ether 1:10).

EXAMPLE XX (8S)-[8-(tert-Butyl-dimethyl-silyloxy)-3-cyclopentyl-1-(4-fluoro-phenyl)-6,6-dimethyl-5,6,7,8-tetrahydro-naphthalene-2-yl]-methanol

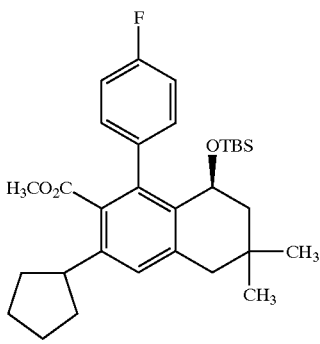

At −78° C., 6.2 ml (9.28 mmol) of a 1.5 M solution of diisobutylaluminium-hydride (DIBAH) in toluene are slowly added to a solution of 1.13 g (2.21 mmol) of the compound of Example XIX in 25 ml of dry toluene, and the mixture is stirred at this temperature for 1 h. After a further 30 minutes at −40° C., the reaction mixture is allowed to warm to 0° C. and hydrolysed using 20 ml of a 20% strength $K^+/Na^+$ tartrate solution. The mixture is filtered through diatamaceous earth and the diatamaceous earth is rinsed with EtOAc and water. The aqueous phase is separated off and reextracted with EtOAc, and the combined organic phases are washed with sat. NaCl solution. The organic phases are dried over $Na_2SO_4$ and concentrated. The crude product is directly employed for further reactions.

Yield: 1.01 g (94%)

$R_f$=0.42 (EtOAc/petroleum ether 1:10).

EXAMPLE XXI (8S)-(tert-Butyl-dimethyl-silyloxy)-3-cyclopentyl-1-(4-fluoro-phenyl)-6,6-dimethyl-5,6,7,8-tetrahydro-naphthalene-2-carbaldehyde

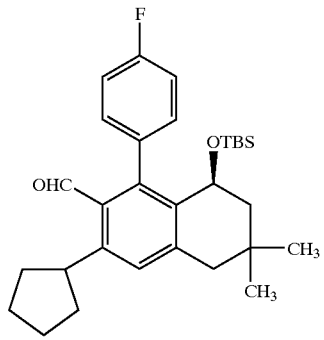

At 0° C., in an argon counterflow, 1.28 g (8.05 mmol) of sulphur trioxide/pyridine complex are added in portions over 5 minutes to a solution of 972 mg (2.01 mmol) of the compound of Example XX, 1.40 ml (10.1 mmol) of triethylamine and 2.5 ml of dimethyl sulphoxide in 10 ml of dry dichloromethane. The mixture is stirred at 0–5° C. for 1 h, 20 ml of 5% NaHCO₃ solution are added and the mixture is extracted with EtOAc. The combined organic phases are washed with 5% NaHCO₃ solution and sat. NaCl solution, dried over Na₂SO₄ and concentrated. The residue is purified by flash chromatography over 100 g of silica gel 60 (elution: EtOAc/cyclohexane/triethylamine 1:10:0.1).

Yield: 840 mg (87%)

R_f=0.60 (EtOAc/petroleum ether 1:10).

EXAMPLE XXII 8-(4-Fluorophenyl)-6-hydroxy-6-isopropyl-7-(4-trifluoromethylbenzoyl)-3-spirocyclo-butyl-decalone-1

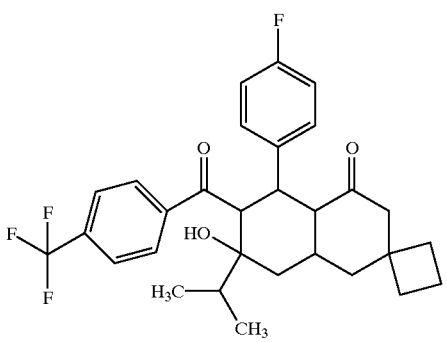

Unter argon and with ice/acetone cooling, 34.67 g (20.04 ml; 182.77 mmol) of titanium tetrachloride and 17.32 g (17.98 ml; 60.92 mmol) of titanium tetra-i-propoxide are added dropwise, if possible simultaneously, to a solution of 11.36 g (71.78 mmol) of vinyl isopropyl silyl enol ether and 8.15 g (59.81 mmol) of 5-spiro[3,5]non-7-en-6-one (Example XXVIII) in 40 ml of dichloromethane, and during the addition, the temperature is kept between −7° C. and −1° C. (approximately 30 min.). The solution becomes dark brown. Stirring is continued for 5 minutes and the mixture is admixed with 17.60 g (59.81 mmol) of 1-(4-fluorophenyl)-3-(4-trifluoromethylphenyl)-propen-3-one (Example XXIX) (solid). The temperature rises from −7° C. to +3° C. The mixture is stirred for 5 minutes with cooling and then overnight at RT. With ice-cooling, the mixture is admixed dropwise with 10 ml of 1 N HCl. The phases are separated and the organic phase is washed once with 1 N HCl and twice with water, dried and concentrated. Crystallization is carried out using petroleum ether.

Yield: 13.100 g (42.4% of theory)

m.p.: 236–238° C.

EXAMPLE XXIII

Mixture of the different 8-(4-fluorophenyl)-6-isopropyl-7-(4-trifluoromethyl-benzoyl)-3-spirocyclobutyl-octahydronaphthalen-1-ones

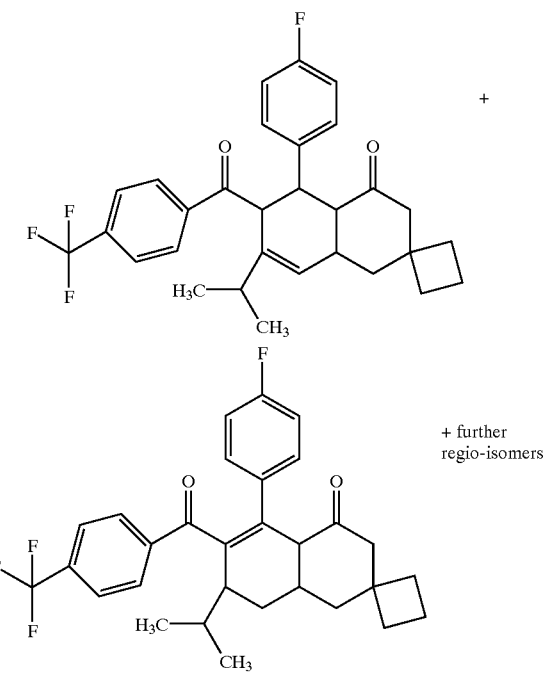

20 g (38.7 mmol) of the compound of Example XXII are initially charged in 316 ml of pyridine and cooled to 0° C. Over a period of 15 minutes, 33.7 ml of thionyl chloride are added dropwise to this mixture at 0° C. Tlc after 10 minutes (petroleum ether/ethyl acetate=4:1) shows complete conversion. At 5–10° C., the reaction mixture is admixed with 480 ml of ethyl acetate, and 190 ml of 4 N HCl are added dropwise. The organic phase is separated off and the aqueous phase is extracted twice with ethyl acetate. The ethyl acetate phases are combined washed once with 2 N HCl (the aqueous phase has to be acidic) and twice with water, dried and concentrated. The residue is digested with 80 ml of petroleum ether for 10 minutes, filtered off wich suction and dried.

Yield: 16.0 g (82.9% of theory)

EXAMPLE XXIV

Mixture of chlorinated 8-(4-fluorophenyl)-6-isopropyl-7-(4-trifluoromethyl-benzoyl)-3-spirocyclo-butyl-octahydronaphthalene-1-ones

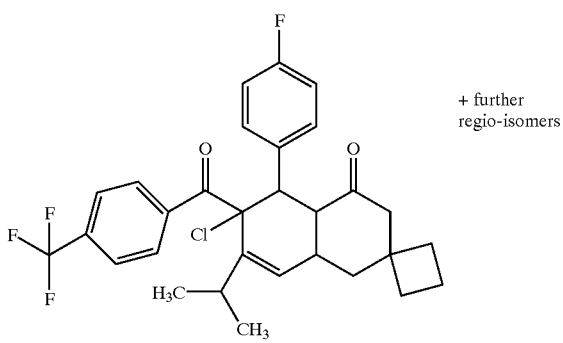

8.0 ml of dichloromethane are added to 0.81 g (1.621 mmol) of the compound of Example XXIII, 0.97 g (7.296 mmol) of N-chloro-succinimide, 0.03 g of bisbenzoyl peroxide, and the mixture is stirred at RT for 3 days. The mixture is admixed with 38.15 ml of dichloromethane and washed with 38.15 ml of water, and the organic phase is dried with Na$_2$SO$_4$ and filtered, the filter cake is rinsed with dichloromethane and the filtrate is concentrated under reduced pressure at 50° C. The product is purified by flash chromatography over 25 g of silica gel (petroleum ether/ethyl acetate=10:1).

Yield: 0.822 g (84.6% of theory)

MS (DCI/NH$_3$):=550 (M+18)

EXAMPLE XXV

5-Spirocyclobutyl-cyclohexanedione mono-isobutyl ether

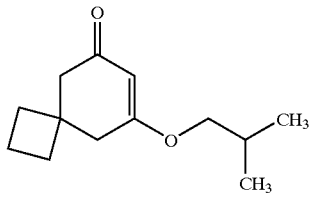

62.10 g (0.838 mol) of isobutanol and 3.4 g (0.02 mol) of p toluenesulphonic acid are added to 85 g (0.558 mol) of 5-spirocyclobutyl-cyclohexanedione in 1.8 l of toluene, and the mixture is heated with stirring on a water separator for 24 h. The mixture is cooled, washed with saturated sodium bicarbonate solution and water, dried and concentrated. This gives 121.1 g of an oil of a purity of 98.55% according to HPLC.

EXAMPLE XXVI

Cyclobutylidene-2-propanone

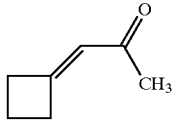

1.15 kg of triphenylphosphoranylidene-2-propanone are added into 1.8 l of silicon oil of a temperature of 100° C., and 42 g of benzoic acid and 242 g of cyclobutanone are added. The mixture is stirred at approximately 110° C. for 12 hours, and the product is subsequently distilled off using water pump vacuum.

b.p$_{10}$=62 to 65° C.

Yield: 330 g, corresponding to 86.5% of theory (NMR, CDCl$_3$: 2.1 ppm t '(2H); 2.2 ppm s (3H); 2.9 and 3.2 tr (2 H each); 5.95 ppm m (1H)

EXAMPLE XXVII

Cyclobutyl-dimedone (spiro[3,5]nonane-6,8-dione)

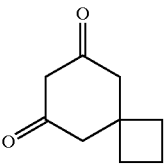

500 ml of 30% strength NaOMe in methanol are initially charged and diluted with 640 ml of methanol. At approximately 60° C., 359 g of dimethyl malonate are added to this mixture, which is then heated at reflux for 10 minutes. 300 g of cyclobutylidene-2-propanone are subsequently added, and the mixture is heated at reflux for 4 hours. For hydrolysis, 336 g of KOH dissolved in 1600 ml of water are added, and the mixture is heated at reflux for 1 hour. The mixture is subsequently acidified using 20% strength hydrochloric acid, and stirred at pH 3 to 5 until the evolution of CO$_2$ has ceased. The methanol is distilled off, and the remainder is stirred until the temperature has dropped to room temperature, and the precipitated solid is isolated, washed neutral and dried under reduced pressure at 55° C.

Yield: 412 g, corresponding to 99.4% of theory (NMR, DMSO, 1.7–1.95 ppm m (6H); 2.4 ppm s (4H), 5.2 ppm s (1H); 11.1 ppm br.s (—OH)

EXAMPLE XXVIII

Spiro[3,5]non-7-en-6-one (without intermediate isolation of the enol ether)

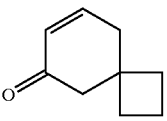

492.2 g of cyclobutyl-dimedone are added to 1.7 l of toluene, and the mixture is admixed with 264 g of isobutanol and 3.7 g of PTSA. After approximately 5 hours of azeotrope distillation, the reaction to give the enol is complete. The reaction mixture is cooled to 20° C. and admixed with 1006 g of 65% strength Red-Al in toluene. On addition, the reaction mixture warms to 40 to 50° C. The mixture is stirred at this temperature for about 2 hours until the reaction has gone to completion. 310 g of KOH in 1250 g of water are subsequently added, the lower, aqueous phase is separated off and the toluene phase is admixed with 364 g of concentrated hydrochloric acid in 980 g of water. The mixture is stirred for 30 minutes, the phases are separated and the toluene is distilled off under reduced pressure. The residue is fractionated using water pump vacuum.

Yield: 340 g b.p.$_{10}$=92 to 94° C. (77% of theory)/NMR, DMSO; 1.7 to 1.9 ppm m (6H); 2.5 ppm s+d (4H); 5.9+6.9 (1H each)

The preparation of the corresponding enol ether is described under Example XXV.

EXAMPLE XXIX 1-(4-Fluorophenyl)-3-(4-trifluoromethylphenyl)-propen-3-one

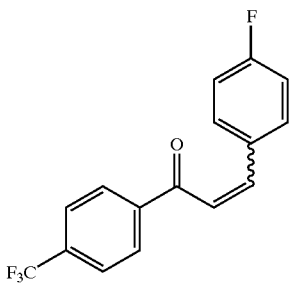

8 l of methylcyclohexane are initially charged and 3000 g of 4-fluorobenzaldehyde, 5000 g of 4-trifluoromethylacetophenone and 150 ml of conc. hydrochloric acid are added. The mixture is distilled azeotropically for approximately 8 hours until no more water separates off. After cooling to 10 to 15° C., the precipitated solid is filtered off with suction and washed with cold methylcyclohexane.

After drying under reduced pressure, 6756 g of product are isolated (95% of theory) (NMR, CDCl$_3$, 7.1 to 8.2 ppm m (4+2+4H)

PREPARATION EXAMPLES

EXAMPLE 1 AND EXAMPLE 2

5-(tert-Butyldimethylsilyloxy)-7,7-dimethyl-4-(4-fluorophenyl)-3-[hydroxy-(4-trifluoromethyl-phenyl)-methyl]-2-isopropyl-5,6,7,8-tetrahydronaphthalene

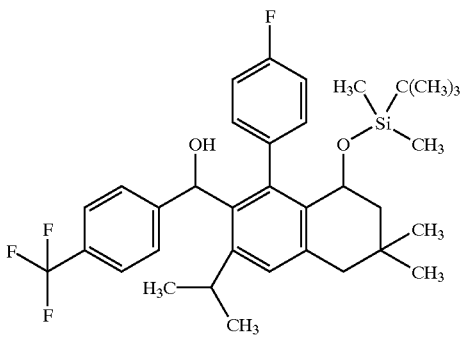

Under argon, 2.28 g of the compound of Ex. XI are dissolved in THF and cooled to 5° C. 59.85 ml of a THF solution containing 3 eq of 4-trifluoromethyl-phenylmagnesium bromide are then added dropwise at 5–10° C. over a period of 30 min, and the mixture is stirred for 1 h. For work-up, initially 30 ml of a sat. ammonium chloride solution are added dropwise, the mixture is stirred for 10 minutes and then stirred into a mixture of 500 ml of water and 250 ml of toluene, and the phases are separated. The aqueous phase was reextracted once more using 125 ml of toluene, and the combined organic phases were washed twice with 125 ml of water each time until neutral, dried over sodium sulphate and concentrated at at most 50° C. under reduced pressure. The crude product was chromatographed over 250 g of silica gel 60/0.04–0.063 mm (column 5×25 cm) using cyclohexane/ethyl acetate 95:5 and the main fractions were concentratred almost completely. The two diastereomers (diastereomers A and B) crystallize from the cyclohexane residues after scratching and cooling and are then dried under reduced pressure until the weight remains constant.

Yield: 1.29 g of diastereomer A (52% of theory) (Example 1);

Yield: 1.01 g of diastereomer B (42% of theory) (Example 2)

$R_f$=0.40 diastereomer A (Cy: EA 9:1) (Example 1);

$R_f$=0.33 diastereomer B (Cy: EA 9:1) (Example 2)

EXAMPLE 3

5-(tert-Butyldimethylsilyloxy)-7,7-dimethyl-4-(4-fluorophenyl)-3-[fluoro-(4-trifluoromethyl-phenyl)-methyl]-2-isopropyl-5,6,7,8-tetrahydronaphthalene

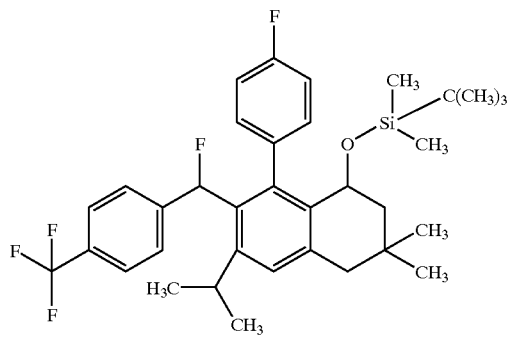

Under argon, 0.8 g of the compound of Ex. 2 (diastereomer B) is dissolved in toluene and cooled to −70° C. 0.26 ml of diethylaminosulphur trifluoride is subsequently added dropwise over a period of 5 min and the mixture is stirred for 60 min, during which the internal temperature is allowed to rise to −60° C. For work-up, 5 ml of sat. sodium bicarbonate solution are added dropwise, the mixture is stirred for 10 min and the phases are separated. The organic phase is washed 2 times with 5 ml of water each time until neutral, dried over sodium sulphate and concentrated under reduced pressure at 50° C. The crude product crystallizes, and it was dried under reduced pressure until its weight remained constant and used without purification for the next step.

Yield: 0.78 g (83% of theory)

$R_f$=0.65 (Cy: EA 9:1)

EXAMPLE 4 AND EXAMPLE 5

[1S,7(1RS)]-1-(tert-Butyl-dimethyl-silyloxy)-6-cyclopentyl-8-(4-fluoro-phenyl)-7-[hydroxy-(4-trifluoromethyl-phenyl)-methyl]-3,3-dimethyl-1,2,3,4-tetrahydronaphthalene

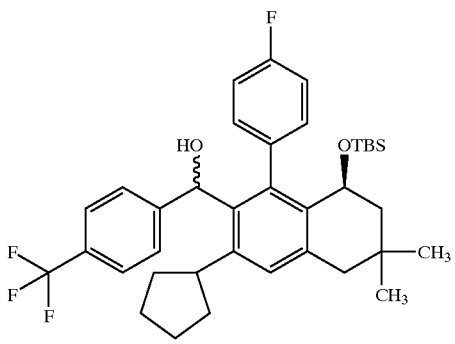

Under argon and at −25° C., 33.5 ml of a 0.224 M solution of 4-trifluoromethyl-phenyl-magnesium bromide (prepared by refluxing 3.02 g of bromo-4-trifluoromethyl-benzene with 324 mg of magnesium turnings in 60 ml of dry THF) are added over a period of 15 minutes to a solution of 830 mg (1.73 mmol) of the compound of Example XXI in 10 ml of dry THF. The mixture is stirred at −20° C. for 40 minutes and hydrolysed at 0° C. by addition of 20 ml of 5% NaHCO$_3$ solution. The mixture is extracted with EtOAc and the combined organic phases are washed with 5% NaHCO$_3$ solution and NaCl solution, dried over Na$_2$SO$_4$ and concentrated. The residue is purified over 170 g of silica gel (elution EtOAc/petroleum ether/triethylamine 1:10:0.1).

Yield: 972 mg (90%) of a 1:1 mixture of two diastereomers

R$_f$=0.32 (diastereomer 1) (EtOAc/petroleum ether 1:10) (Example 4) and

R$_f$=0.24 (diastereomer 2) (EtOAc/petroleum ether 1:10) (Example 5).

EXAMPLE 6

[1S, 7(1RS)]-1-(tert-Butyl-dimethyl-silyloxy)-6-cyclopentyl-8-(4-fluoro-phenyl)-7-[fluoro-(4-trifluoromethyl-phenyl)-methyl]-3,3-dimethyl-1,2,3,4-tetrahydro-naphthalene

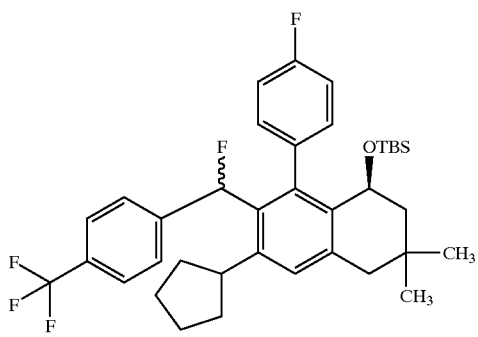

At −78° C., 407 mg (2.53 mmol) of DAST are added to a solution of 960 mg (1.53 mmol) of the compound of Example 4 and 5. After 5 minutes, the mixture is allowed to warm to room temperature and then stirred for another 30 minutes. At 0° C., the reaction mixture is hydrolysed with 15 ml of a 5% solution of NaHCO$_3$. The mixture is extracted with EtOAc, and the combined organic phases are washed with sat. NaCl solution, dried over Na$_2$SO$_4$ and concentrated. The product is subsequently purified over silica gel 60 (elution: EtOAc/petroleum ether/triethylamine 1:20:0.1).

Yield: 874 mg (91%) of a 1:1 mixture of two diastereomers

R$_f$=0.68 (EtOAc/petroleum ether 1:20).

EXAMPLE 7

7,7-Dimethyl-4-(4-fluorophenyl)-3-[fluoro-(4-trifluoromethyl-phenyl)-methyl]-2-isopropyl-5,6,7,8-tetrahydronaphthalen-5-ol

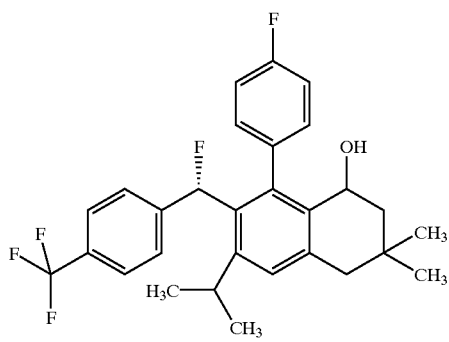

At room temperature, 778 mg of the compound of Ex. 3 are dissolved in 12.9 ml of THF, 12.9 ml of a 1 molar solution of tetrabutylammonium fluoride is added dropwise over a period of 5 min and the mixture is stirred for 3 h. For work-up, the reaction solution was stirred into a mixture of 130 ml of water and 65 ml of toluene, and the aqueous phase was reextracted once using 30 ml of toluene. The combined organic phases were washed twice with 30 ml of water, dried over sodium sulphate and concentrated under reduced pressure at at most 50° C. The crude product was chromatographed over 90 g of silica gel 60/0.04–0.063 mm (column 3×25 cm) using cyclohexane/diethyl ether 90:10, the main fraction was concentrated and the product was crystallized from cyclohexane.

Yield: 0.45 g (66% of theory)

R$_f$=0.27 (Cy: EA 9:1)

EXAMPLE 8 AND EXAMPLE 9

[1S,7(1S)]-6-Cyclopentyl-8-(4-fluoro-phenyl)-7-[fluoro-(4-trifluoromethyl-phenyl)-methyl]-3,3-dimethyl-1,2,3,4-tetrahydro-naphthalen-1-ol

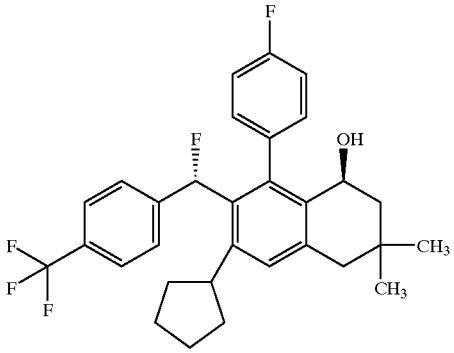

A solution of 865 mg (1.38 mmol) of the compound of Example 6 in 30 ml of THF is admixed with 12.5 ml of a 1.1 M solution of tetrabutylammonium fluoride in THF, and the mixture is stirred at room temperature for 16 h. Water is added, and the mixture is extracted with EtOAc. The combined organic phases are washed with sat. NaCl solution, dried over $Na_2SO_4$ and concentrated. The diastereomers are separated over 140 g of silica gel 60 (elution: toluene/cyclohexane 8:2)

EXAMPLE 8

Yield: 236 mg (33%) of diastereomer 2 (title compound, $R_f$=0.38, toluene/cyclohexane 8:2)

EXAMPLE 9

Yield: 77 mg (11%) of diastereomer 1 ($R_f$=0.29, toluene/cyclohexane 8:2).

EXAMPLE 10

1-(4-Fluorophenyl)-3-isopropyl-8-oxo-6-spirocyclobutyl-2-(4-trifluoromethyl-benzoyl)-5,6,7,8-tetrahydronaphthalene

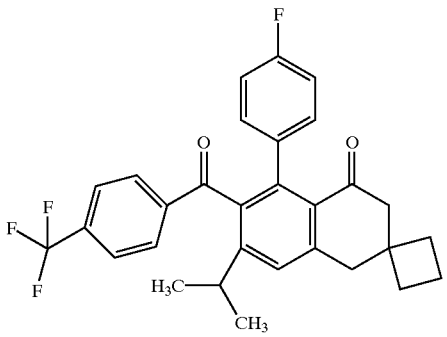

The reaction is carried out under an atmosphere of argon protective gas. 0.5 g (0.801 mmol) of the compound of Example XXIV is initially charged in 13 ml of dioxane, 0.5 g (3.283 mmol) of 1,5-diazabicyclo-[5.4.0]-undec-7-ene (DBU) and 0.29 g (0.985 mmol) of 1-(4-trifluoromethylphenyl)-3-(4-fluorophenyl)-propen-3-one are added, and the mixture is stirred at 96° C. for 20 hours. The reaction mixture is cooled, admixed with 150 ml of ethyl acetate, washed once with 150 ml of 1 N HCl and three times with 30 ml of water each time, dried over $Na_2SO_4$, which is then rinsed with ethyl acetate, and the mixture is concentrated at 60° C. under reduced pressure. The crude product is chromatographed over 100 g of silica gel (petroleum ether/ethyl acetate=10:1).

Yield: 0.311 g (64.1% of theory)

m.p.: 156 to 157° C.

EXAMPLE 11

(8S)-1-(4-Fluorophenyl)-8-hydroxy-3-isopropyl-6-spirocyclobutyl-2-(4-trifluoromethyl-benzoyl)-5,6,7,8-tetrahydronaphthalene

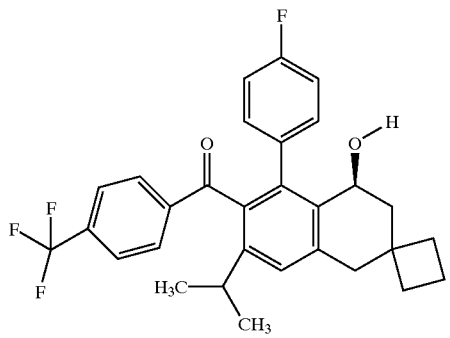

Enantio- and regioselective (site-selective) reduction of the diketone compound:

Under exclusion of moisture and under argon, 20.4 mg (0.14 mmol; 0.31 eq.) of (1R,2S)-1-aminoindan-2-ol were dissolved in 0.5 ml of THF (anhydrous). 225 mg (1.38 mmol; 3.12 eq.) of a borane-N,N-diethylaniline complex were then added, and the mixture was stirred at RT (28° C.) for 40 minutes and then with ice-cooling for 20 minutes. At this temperature, 219 mg of the compound of Example 10 dissolved in 1.5 ml of THF (anhydrous) were added over a period of 2 min, followed by rinsing with 0.5 ml of THF. The reaction mixture was stirred overnight (17 h) and slowly allowed to warm to RT. The reaction was quenched by addition of 2 ml of methanol (evolution of gas!). After dilution with ethyl acetate, the mixture was extracted with 10 ml of 1 N hydrochloric acid, the aqueous phase was extracted three times with ethyl acetate, the combined organic phases were extracted with saturated aqueous sodium bicarbonate solution, the aqueous phase was extracted two more times with ethyl acetate and the combined organic phases were dried over sodium sulphate. The solvent was removed under reduced pressure, giving 250 mg of a solid crude product. Chromatographic purification over silica gel using ethyl acetate/petroleum ether=1:9 gave 182 mg (82%) of product as a white solid.

m.p. (uncorrected): 199–201° C. (ethyl acetate/petroleum ether)

EXAMPLE 12

(8S)-1-(4-Fluorophenyl)-8-tert-butyldimethylsilyloxy-3-isopropyl-6-spirocyclobutyl-2-(4-trifluoromethylbenzoyl)-5,6,7,8-tetrahydronaphthalene

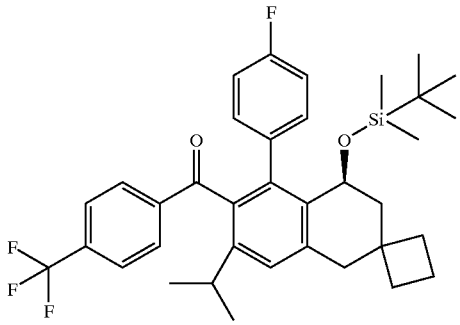

Under exclusion of moisture and in an atmosphere of argon, 169 mg (0.34 mmol) of the compound of Example 11 were dissolved in 2 ml of toluene and cooled in an ice/acetone bath (bath temperature: −11° C.). After the addition of 74 mg (0.69 mmol) of lutidine, 136 mg (0.52 mmol) of tert-butyldimethylsilyltriflate in 1 ml of toluene were added dropwise, rinsing with 0.2 ml of toluene. After 70 minutes of stirring with warming to −9° C. (bath temperature), cooling was changed to ice-water cooling. When, after a reaction time of 130 min, no further conversion was noticed, a further 109 mg (1.02 mmol) of lutidine and 135 mg (0.51 mmol) of tert-butyldimethyl-silyltriflate were added after 150 min. The mixture was stirred with ice-cooling for 45 min and warmed to RT for 10 min, the reaction mixture was diluted with ethyl acetate and the reaction was quenched by addition of 10 ml of 1 N hydrochloric acid. After extraction, the aqueous phase was extracted 3 times with ethyl acetate, the combined organic phases were neutralized using saturated aqueous bicarbonate solution, the aqueous phase was extracted twice using methyl acetate and the combined organic phases were dried over sodium sulphate. The solvent was removed under reduced pressure. After chromatography of the residue over silica gel using ethyl acetate/petroleum ether 1:20, 160 mg (77%) of a white solid were isolated which contained the elimination product as an impurity. The by-product could be removed by digestion with methanol.

m.p. (uncorrected): 137 to 138° C. (methanol)

EXAMPLE 13

(S)-8-(t-Butyl-dimethyl)-silyloxy-1-(4-fluorophenyl)-2-[(R)-hydroxy-(4-trifluoromethylphenyl)-methyl]-3-isopropyl-6-spiro-cyclobutyl-5,6,7,8-tetrahydronaphthalene

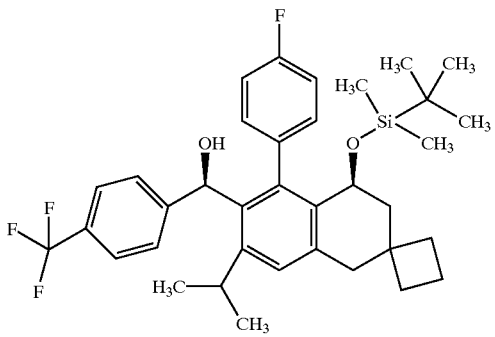

700 mg (1.22 mmol) of the ketone precursor of Example 12 are dissolved in 40 ml of THF, cooled to 0° C. and admixed dropwise with a 1 molar solution of lithium aluminium hydride in THF. The mixture is stirred at 0° C. for 15 min and at RT for 1.5 h. The mixture is cooled to 0° C., admixed dropwise with 20 ml of water and extracted three times with ethyl acetate. The combined ethyl acetate phases are washed with water and saturated sodium chloride solution, dried and concentrated. Recrystallization from cyclohexane gives 200 mg (26.8%) of colourless crystals. Chromatography of the mother liquor give another 210 mg (28.1% of theory) of the desired diastereomer.

EXAMPLE 14

(S)-8-(t-Butyl-dimethyl)-silyloxy-1-(4-fluorophenyl)-2-[(S)-fluoro-(4-trifluoromethyl-phenyl)-methyl]-3-isopropyl-6-spiro-cyclobutyl-5,6,7,8-tetrahydronaphthalene

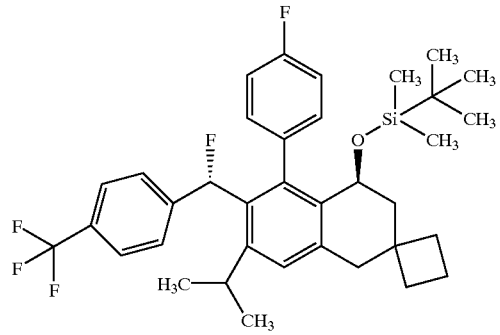

Under inert gas, 8.9 g (14.52 mmol) of the alcohol of Example 13 are dissolved in 125 ml of toluene and cooled to −70° C. At this temperature, 2.88 ml of DAST are added dropwise and the mixture is stirred at approximately −60° C. for half an hour. Work-up is carried out by addition of 75 ml of saturated sodium bicarbonate solution, extraction of the aqueous phase with toluene, washing of the combined organic phases with water and saturated sodium chloride solution, drying over sodium sulphate and concentrating. Chromatography over silica gel using petroleum ether/methylene chloride (95/5) gave 6.5 g of fluorine compound as a colourless solid (71% of theory).

EXAMPLE 15

(S)-8-Hydroxy-1-(4-fluorophenyl)-2-[(S)-fluoro-(4-trifluoromethyl-phenyl)-methyl]-3-isopropyl-6-spiro-cyclobutyl-5,6,7,8-tetrahydronaphthalene

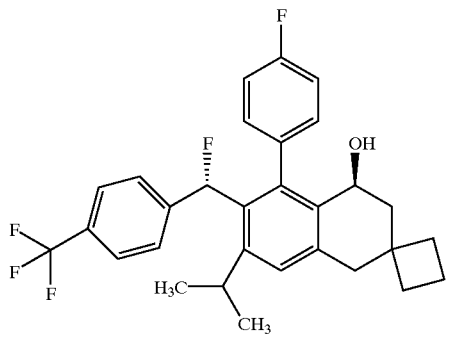

Under inert gas, 6.5 g (10.57 mmol) of the fluorine compound of Example 14 are dissolved in 130 ml of tetrahydrofuran and, at room temperature, stirred with 95 ml of a 1 molar solution of tetrabutylammonium fluoride for 2 hours. Work-up is carried out by addition of water at 10° C., extraction of the aqueous phase with toluene, washing of the combined organic phases with water and saturated sodium chloride solution, drying over sodium sulphate and concentration. Chromatography over silica gel using toluene/cyclohexane (9/1) gave 4.6 g of the alcohol as a colourless solid (85% of theory).

The compounds listed in Table 1 are prepared using the methods of the preparation procedures shown:

TABLE 1

| Ex. No. | Structure | Isomer | $R_f$ value*/preparation: |
|---|---|---|---|
| 16 | 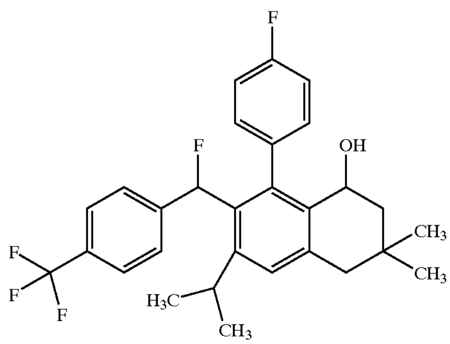 | diastereomer A | 0.30 (A) 90:10/of Ex. 1 (2 steps) |
| 17 | 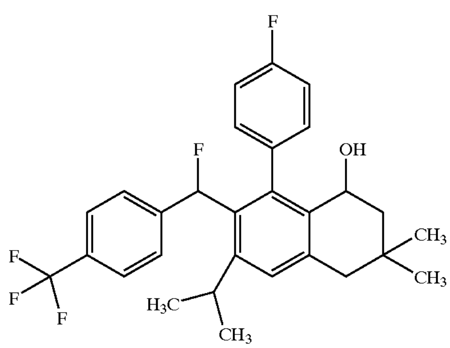 | diastereomer B | 0.27 (A) 90:10/of Ex. 3 |
| 18 | 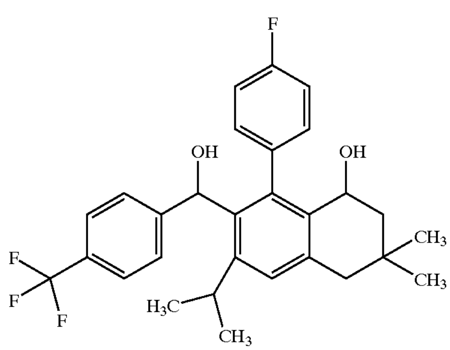 | diastereomer A | 0.15 (A) 80:20/of Ex. 1 |

TABLE 1-continued

| Ex. No. | Structure | Isomer | $R_f$ value*/preparation: |
|---|---|---|---|
| 19 | 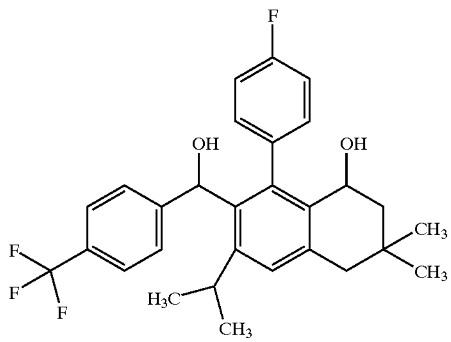 | diastereomer B | 0.30 (A) 80/20/of Ex. 2 |
| 20 | 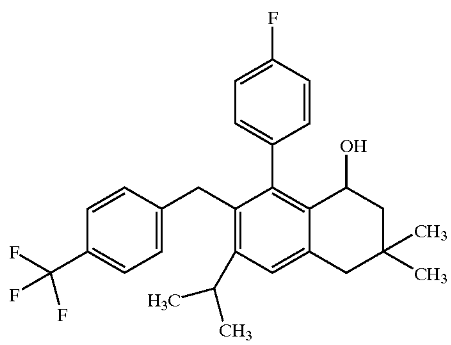 | racemate | 0.27 (A) 90:10/of Ex. 16 using diisobutyl-aluminum hydride) |
| 21 | 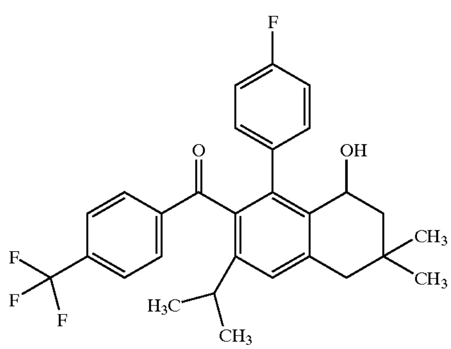 | racemate | 0.23 (A) 90:10/of Ex. 2 (2 steps) |
| 22 | 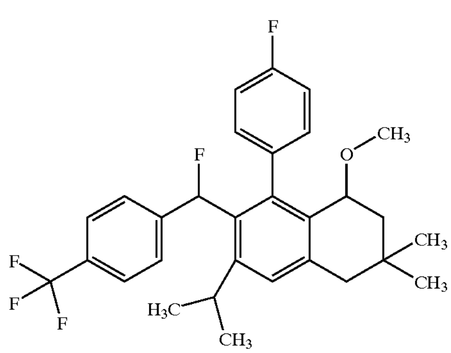 | diastereomer A | 0.33 (B) 90:10/of Ex. 16 (MeI) |

TABLE 1-continued

| Ex. No. | Structure | Isomer | $R_f$ value*/preparation: |
|---|---|---|---|
| 23 | 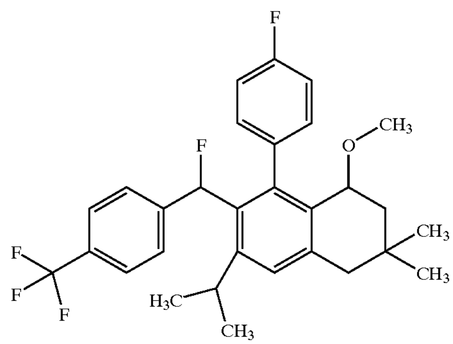 | diastereomer B | 0.43 (B) 95:5/of Ex. 17 (MeI) |
| 24 | 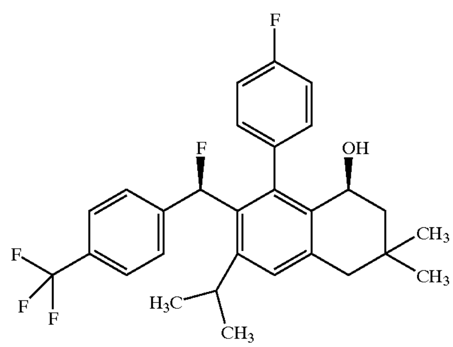 | enantiomer A1 | 0.30 (C)/of Ex. 3 |
| 25 | 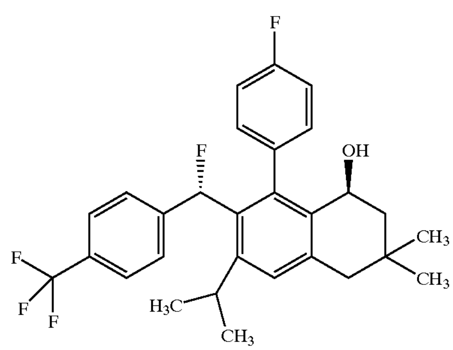 | enantiomer B1 | 0.26 (C)/of Ex. 3 |
| 26 | 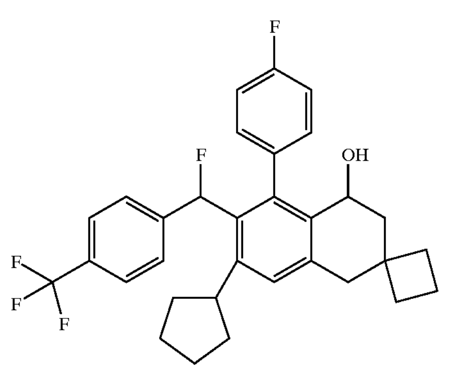 | diastereomer A | 0.80 (D) 20/1/analogous to Ex. 16 |

TABLE 1-continued

| Ex. No. | Structure | Isomer | $R_f$ value*/preparation: |
|---|---|---|---|
| 27 | 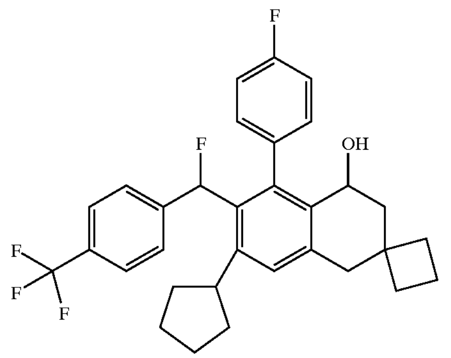 | diastereomer B | 0.26 (D) 20/1/analogous to Ex. 17 |
| 28 | 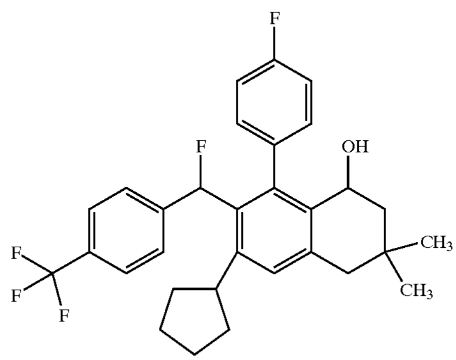 | diastereomer A racemate | 0.25 (E) 8/2/analogous to Ex. 16 |
| 29 | 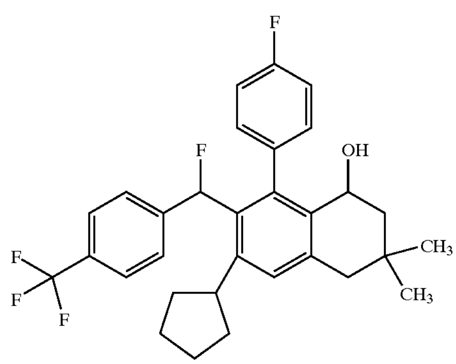 | diastereomer B racemate | 0.33 (E) 8/2/analogous to Ex. 17 |
| 30 | 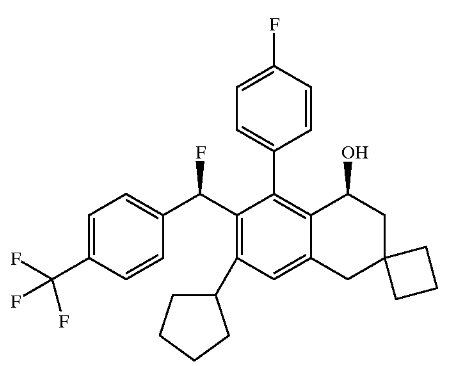 | enantiomer A1 | 0.22 (E) 80/20/analogous to Ex. 24 |

TABLE 1-continued

| Ex. No. | Structure | Isomer | $R_f$ value*/preparation: |
|---|---|---|---|
| 31 | 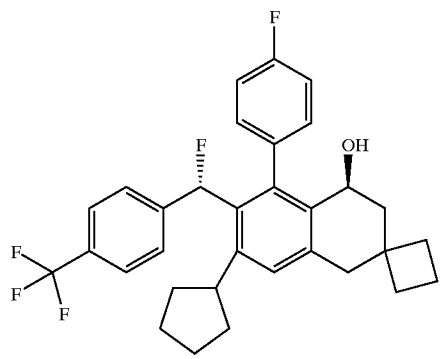 | enantiomer B1 | 0.28 (F) 20/80/analogous to Ex. 25 |
| 32 | 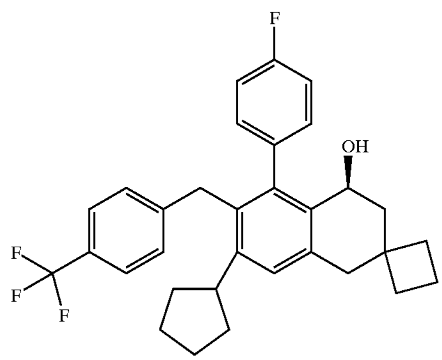 | enantiomer 1 | 0.38 (B) 2x/analogous to Ex. 20 |
| 33 | 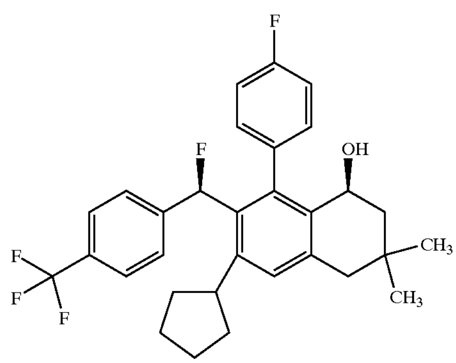 | enantiomer A1 | 0.25 (E) 8/2/analogous to Ex. 24 |
| 34 | 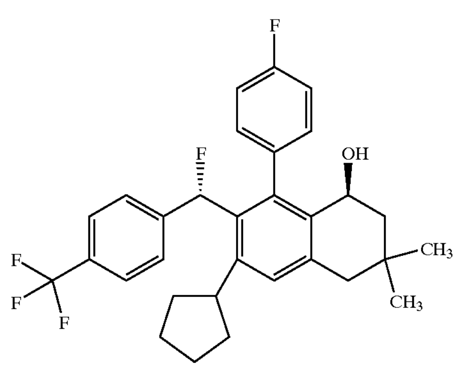 | enantiomer B1 | 0.33 (E) 8/2/analogous to Ex. 25 |

TABLE 1-continued

| Ex. No. | Structure | Isomer | R_f value*/preparation: |
|---|---|---|---|
| 35 | 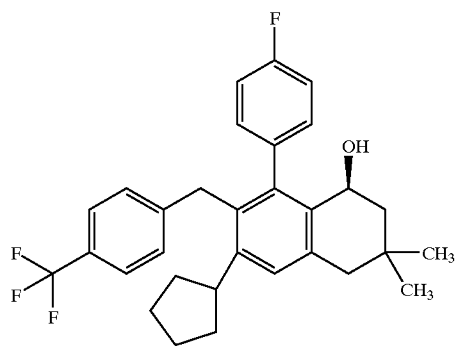 | enantiomer 1 | 0.35 (E) 8/2/analogous to Ex. 20 |
| 36 | 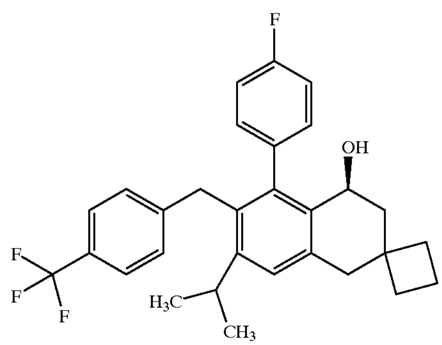 | enantiomer 1 | 0.31 (A) 9/1/analogous to Ex. 20 |
| 37 | 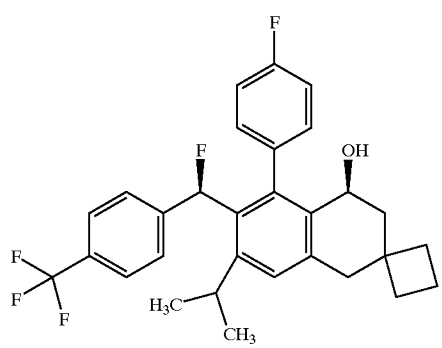 | enantiomer A1 | 0.32 (A) 9/1/analogous to Ex. 24 |
| 38 | 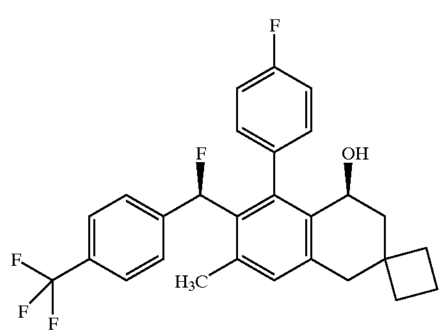 | enantiomer A1 | 0.25 (E) 80/20/analogous to Ex. 24 |

TABLE 1-continued

| Ex. No. | Structure | Isomer | R_f value*/preparation: |
|---|---|---|---|
| 39 | 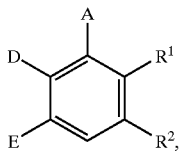 | enantiomer B1 | 0.30 (E) 80/20/analogous to Ex. 25 |
| 40 | 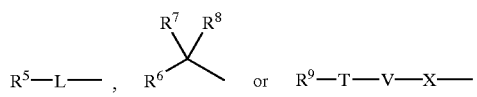 | enantiomer 1 | 0.25 (B) 2x/analogous to Ex. 20 |

*Mobile phases used
A = cyclohexane/ethyl acetate
B = cyclohexane/diethyl ether
C = toluene
D = petroleum ether/ethyl acetate
E = toluene/cyclohexane

What is claimed is:

1. Compounds of the general formula (I), (I)

in which
A represents cycloalkyl having 3 to 8 carbon atoms, or represents aryl having 6 to 10 carbon atoms, or represents a 5- to 7-membered saturated, partially unsaturated or unsaturated, optionally benzo-fused heterocycle having up to 4 heteroatoms selected from the group consisting of S, N and/or O,
where aryl and the abovementioned heterocyclic ring systems may optionally be substituted up to 5 times by identical or different substituents selected from the group consisting of cyano, halogen, nitro, carboxyl, hydroxyl, trifluoromethyl, trifluoromethoxy, or by straight-chain or branched alkyl, acyl, hydroxyalkyl, alkylthio, alkoxycarbonyl, oxyalkoxycarbonyl or alkoxy having in each case up to 7 carbon atoms, or by a group of the formula —NR$^3$R$^4$
in which
R$^3$ and R$^4$ are identical or different and each represents hydrogen, phenyl or straight-chain or branched alkyl having up to 6 carbon atoms, D represents a radical of the formula R$^5$—L—  ,  R$^6$$\underset{}{\overset{R^7\ R^8}{\diagup\!\!\!\diagdown}}$  or  R$^9$—T—V—X— in which
R$^5$, R$^6$ and R$^9$ independently of one another each represent cycloalkyl having 3 to 6 carbon atoms, or aryl having 6 to 10 carbon atoms or a 5- to 7-membered, optionally benzo-fused, saturated or unsaturated, mono-, bi- or tricyclic heterocycle having up to 4 heteroatoms selected from the group consisting of S, N and/or O,
where the cycles are optionally, in the case of the nitrogen-containing rings also via the N-function, substituted up to 5 times by identical or different constituents selected from the group consisting of halogen, trifluoromethyl, nitro, hydroxyl, cyano, carboxyl, trifluoromethoxy, straight-chain or branched acyl, alkyl, alkylthio, alkylalkoxy, alkoxy or alkoxycarbonyl having in each case up to 6 carbon atoms, by aryl or trifluoromethyl-substituted aryl having in each case 6 to 10 carbon atoms or by an optionally benzo-fused aromatic 5- to 7-membered heterocycle having up to 3 heteroatoms selected from the group consisting of S, N and/or O,
and/or by a group of the formula —OR$^{10}$, —SR$^{12}$, —SO$_2$R$^{12}$ or —NR$^{13}$R$^{14}$, in which
$R^{10}$, $R^{11}$ and $R^{12}$ independently of one another each represent aryl having 6 to 10 carbon atoms which for its part is substituted up to 2 times by identical or different substituents selected from the group consisting of phenyl, halogen or by straight-chain or branched alkyl having up to 6 carbon atoms,
$R^{13}$ and $R^{14}$ are identical or different and are as defined above for $R^3$ and $R^4$,
or
$R^5$ and/or $R^6$ represents/represent a radical of the formula

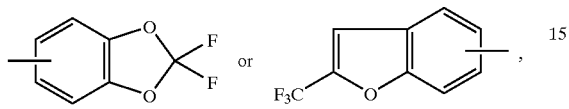

$R^7$ represents hydrogen, halogen or methyl, and
$R^8$ represents hydrogen, halogen, azido, trifluoromethyl, hydroxyl, trifluoromethoxy, straight-chain or branched alkoxy or alkyl having in each case up to 6 carbon atoms or a radical of the formula —$NR^{15}R^{16}$,
in which
$R^{15}$ and $R^{16}$ are identical or different and are as defined above for $R^3$ and $R^4$,
or
$R^7$ and $R^8$ together form a radical of the formula =O or =$NR^{17}$,
in which
$R^{17}$ represents hydrogen or straight-chain or branched alkyl, alkoxy or acyl having in each case up to 6 carbon atoms,
L represents a straight-chain or branched alkylene or alkenylene chain, having in each case up to 8 carbon atoms, which is optionally substituted up to 2 times by hydroxyl,
T and X are identical or different and each represents a straight-chain or branched alkylene chain having up to 8 carbon atoms,
or
T or X represents a bond,
V represents an oxygen or sulphur atom or represents a —$NR^{18}$ group,
in which
$R^{18}$ represents hydrogen or straight-chain or branched alkyl having up to 6 carbon atoms or phenyl,
E represents cycloalkyl having 3 to 8 carbon atoms, or represents straight-chain or branched alkyl having up to 8 carbon atoms which is optionally substituted by cycloalkyl having 3 to 8 carbon atoms or hydroxyl, or represents phenyl, which is optionally substituted by halogen or trifluoromethyl,
$R^1$ and $R^2$ together form a straight-chain or branched alkylene chain, having up to 7 carbon atoms, which has to be substituted by a carbonyl group and/or by a radical of the formula

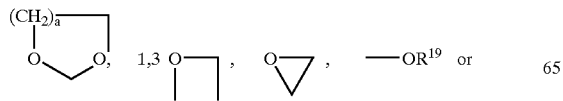

-continued

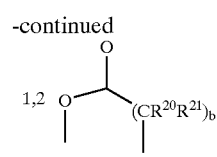

in which
a and b are identical or different and each represents a number 1, 2 or 3,
$R^{19}$ represents hydrogen, cycloalkyl having 3 to 7 carbon atoms, straight-chain or branched silylalkyl having up to 8 carbon atoms or straight-chain or branched alkyl having up to 8 carbon atoms which is optionally substituted by hydroxyl, straight-chain or branched alkoxy having up to 6 carbon atoms or by phenyl which for its part may be substituted by halogen, nitro, trifluoromethyl, trifluoromethoxy or by phenyl or tetrazole-substituted phenyl,
and alkyl is optionally substituted by a group of the formula —$OR^{22}$,
in which
$R^{22}$ represents straight-chain or branched acyl having up to 4 carbon atoms or benzyl,
or
$R^{19}$ represents straight-chain or branched acyl having up to 20 carbon atoms or benzoyl which is optionally substituted by halogen, trifluoromethyl, nitro or trifluoromethoxy, or straight-chain or branched fluoracyl having up to 8 carbon atoms and 9 fluorine atoms,
$R^{20}$ and $R^{21}$ are identical or different and each represents hydrogen, phenyl or straight-chain or branched alkyl having up to 6 carbon atoms,
or
$R^{20}$ and $R^{21}$ together form a 3- to 6-membered carbocycle,
and the alkylene chain which is formed by $R^1$ and $R^2$ is optionally substituted up to 6 times, optionally also geminally, by identical or different substituents selected from the group consisting of trifluoromethyl, hydroxyl, nitrile, halogen, carboxyl, nitro, azido, cyano, cycloalkyl or cycloalkyloxy having in each case 3 to 7 carbon atoms, by straight-chain or branched alkoxycarbonyl, alkoxy or alkylthio having in each case up to 6 carbon atoms or by straight-chain or branched alkyl having up to 6 carbon atoms which for its part is substituted up to 2 times by identical or different substituents selected from the group consisting of hydroxyl, benzyloxy, trifluoromethyl, benzoyl, straight-chain or branched alkoxy, oxyacyl and carboxyl having in each case up to 4 carbon atoms and/or phenyl which for its part may be substituted by halogen, trifluoromethyl or trifluoromethoxy,
and/or the alkylene chain which is formed by $R^1$ and $R^2$ is optionally substituted, also geminally, up to 5 times by identical or different substituents selected from the group consisting of phenyl, benzoyl, thiophenyl and sulphonylbenzyl, which for their part are optionally substituted by halogen, trifluoromethyl, trifluoromethoxy or nitro,
and/or the alkylene chain formed by $R^1$ and $R^2$ is optionally substituted by a radical of the formula

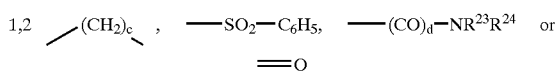

in which
c represents a number 1, 2, 3 or 4,
d represents a number 0 or 1,
$R^{23}$ and $R^{24}$ are identical or different and each represents hydrogen, cycloalkyl having 3 to 6 carbon atoms, straight-chain or branched alkyl having up to 6 carbon atoms, benzyl or phenyl, which is optionally substituted up to 2 times by identical or different substituents selected from the group consisting of halogen, trifluoromethyl, cyano, phenyl and nitro,
and/or the alkylene chain formed by $R^1$ and $R^2$ is optionally substituted by a spiro-linked radical of the formula

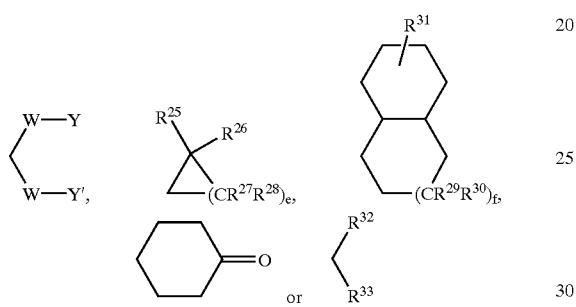

in which
w represents either an oxygen or a sulphur atom,
Y and Y' together form a 2- to 6-membered straight-chain or branched alkylene chain,
e represents a number 1, 2, 3, 4, 5, 6 or 7,
f represents a number 1 or 2,
$R^{25}$, $R^{26}$, $R^{27}$, $R^{28}$, $R^{29}$, $R^{30}$ and $R^{31}$ are identical or different and each represents hydrogen, trifluoromethyl, phenyl, halogen or straight-chain or branched alkyl or alkoxy having in each case up to 6 carbon atoms,
or
$R^{25}$ and $R^{26}$ or $R^{27}$ and $R^{28}$, in each case together, form a straight-chain or branched alkyl chain having up to 6 carbon atoms,
or
$R^{25}$ and $R^{26}$ or $R^{27}$ and $R^{28}$, in each case together, form a radical of the formula

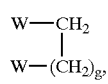

in which
W is as defined above,
g represents a number 1, 2, 3, 4, 5, 6 or 7,
$R^{32}$ and $R^{33}$ together form a 3- to 7-membered heterocycle which contains an oxygen or sulphur atom or a group of the formula SO, $SO_2$ or $-NR^{34}$,
in which
$R^{34}$ represents hydrogen, phenyl, benzyl or straight-chain or branched alkyl having up to 4 carbon atoms,
and stereoisomers, stereoisomer mixtures and salts thereof.

2. Compounds of the formula (I) according to claim 1, in which
A represents cyclopentyl or represents cyclohexyl, or represents naphthyl, phenyl, pyridyl, thienyl, imidazolyl, pyrryl or morpholinyl, each of which is optionally substituted up to 2 times by identical or different substituents selected from the group consisting of fluorine, chlorine, bromine, amino, hydroxyl, trifluoromethyl, trifluoromethoxy or by straight-chain or branched alkyl, or alkoxy having in each case up to 6 carbon atoms,
D represents a radical of the formula

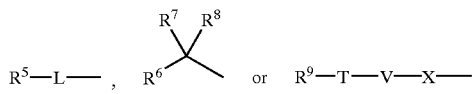

in which
$R^5$, $R^6$ and $R^9$ independently of one another each represent cyclopropyl, cyclopentyl or cyclohexyl, or phenyl, naphthyl, pyridyl, tetrazolyl, pyrimidyl, pyrazinyl, pyrrolidinyl, indolyl, morpholinyl, imidazolyl, benzothiazolyl, phenoxathiin-2-yl, benzoxazolyl, furyl, quinolyl or purin-8-yl,
where the cycles are optionally substituted up to 3 times, in the case of the nitrogen-containing rings also via the N-function, by identical or different substituents selected from the group consisting of fluorine, chlorine, bromine, trifluoromethyl, hydroxyl, cyano, carboxyl, trifluoromethoxy, straight-chain or branched acyl, alkyl, alkylthio, alkylalkoxy, alkoxy or alkoxycarbonyl having in each case up to 4 carbon atoms, triazolyl, tetrazolyl, benzoxathiazolyl, trifluoromethyl-substituted phenyl and phenyl,
and/or are substituted by a group of the formula $-OR^{10}$, $-SR^{11}$ or $-SO_2R^{12}$,
in which
$R^{10}$, $R^{11}$ and $R^{12}$ are identical or different and are each phenyl which for its part is substituted up to 2 times by identical or different substituents selected from the group consisting of phenyl, fluorine, chlorine or by straight-chain or branched alkyl having up to 4 carbon atoms,
or
$R^5$ and/or $R^6$ represents/represent a radical of the formula

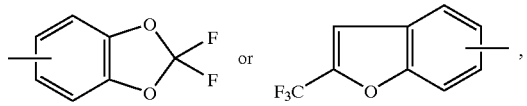

$R^7$ represents hydrogen, fluorine, chlorine or bromine, and
$R^8$ represents hydrogen, fluorine, chlorine, bromine, azido, trifluoromethyl, hydroxyl, trifluoromethoxy, straight-chain or branched alkoxy or alkyl having in each case up to 5 carbon atoms or a radical of the formula $-NR^{15}R^{16}$,
in which
$R^{15}$ and $R^{16}$ are identical or different and each represents hydrogen, phenyl or straight-chain or branched alkyl having up to 4 carbon atoms,
or $R^7$ and $R^8$ together form a radical of the formula =O or =$NR^{17}$,
in which
$R^{17}$ represents hydrogen or straight-chain or branched alkyl, alkoxy or acyl having in each case up to 4 carbon atoms,
L represents a straight-chain or branched alkylene or alkenylene chain, having in each case up to 6 carbon atoms, which is optionally substituted up to 2 times by hydroxyl,
T and X are identical or different and each represents a straight-chain or branched alkylene chain having up to 6 carbon atoms,
or
T or X represents a bond,
V represents an oxygen or sulphur atom or represents a group of the formula $-NR^{18}-$,
in which
$R^{18}$ represents hydrogen or straight-chain or branched alkyl having up to 4 carbon atoms or phenyl,
E represents cyclopropyl, -butyl, -pentyl, -hexyl or -heptyl, or straight-chain or branched alkyl, having up to 6 carbon atoms, which is optionally substituted by cyclopropyl, -butyl, -hexyl, -pentyl, -heptyl or by hydroxyl, or represents phenyl which is optionally substituted by fluorine, chlorine or trifluoromethyl,
$R^1$ and $R^2$ together form a straight-chain or branched alkylene chain, having up to 6 carbon atoms, which has to be substituted by a carboxyl group and/or by a radical of the formula

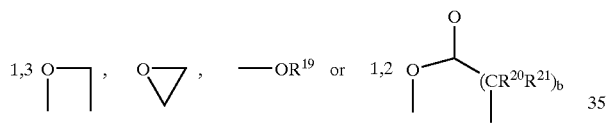

in which
b represents a number 1, 2 or 3,
$R^{19}$ represents hydrogen, cyclopropyl, cyclopentyl, cyclohexyl, straight-chain or branched silylalkyl having up to 7 carbon atoms or straight-chain or branched alkyl having up to 6 carbon atoms which is optionally substituted by hydroxyl, straight-chain or branched alkoxy having up to 4 carbon atoms or by phenyl, which for its part may be substituted by fluorine, chlorine, bromine, nitro, trifluoromethyl, trifluoromethoxy or by phenyl or tetrazole-substituted phenyl,
and alkyl which is optionally substituted by a group of the formula $-OR^{22}$,
in which
$R^{22}$ represents straight-chain or branched acyl having up to 3 carbon atoms or benzyl,
or
$R^{19}$ represents straight-chain or branched acyl having up to 18 carbon atoms or benzoyl which is optionally substituted by fluorine, chlorine, bromine, trifluoromethyl, nitro or trifluoromethoxy, or straight-chain or branched fluoracyl having up to 6 carbon atoms,
$R^{20}$ and $R^{21}$ are identical or different and are each hydrogen, phenyl or straight-chain or branched alkyl having up to 4 carbon atoms,
or
$R^{20}$ and $R^{21}$ together form a cyclopropyl, cyclobutyl, cyclopentyl, cyclohexyl or cycloheptyl ring, and the alkylene chain which is formed by $R^1$ and $R^2$ is optionally substituted up to 5 times, optionally also geminally, by identical or different substituents selected from the group consisting of trifluoromethyl, hydroxyl, carboxyl, azido, fluorine, chlorine, bromine, nitro, cyano, cyclopropyl, cyclobutyl, cyclopentyl, cyclohexyl, cyclopropyloxy, cyclopentyloxy, cyclohexyloxy, by straight-chain or branched alkoxycarbonyl, alkoxy or alkylthio having in each case up to about 5 carbon atoms or straight-chain or branched alkyl having up to 5 carbon atoms which for its part is substituted up to 2 times by identical or different substituents selected from the group consisting of hydroxyl, benzyloxy, benzoyl, straight-chain or branched alkoxy or oxyacyl having in each case up to 3 carbon atoms, trifluoromethyl and phenyl which may for its part be substituted by fluorine, chlorine, bromine, trifluoromethyl or trifluoromethoxy,
and/or the alkylene chain formed by $R^1$ and $R^2$ is optionally, also geminally, substituted up to 4 times by identical or different substituents selected from the group consisting of phenyl, benzoyl, thiophenyl and sulphonylbenzyl, which for their part are optionally substituted by fluorine, chlorine, bromine, trifluoromethyl, trifluoromethoxy or nitro,
and/or is optionally substituted by a radical of the formula

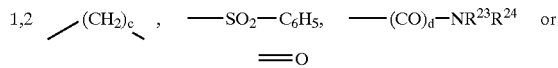

in which
c represents a number 1, 2, 3 or 4,
d represents a number 0 or 1,
$R^{23}$ and $R^{24}$ are identical or different and each represents hydrogen, cyclopropyl, cyclobutyl, cyclopentyl, cyclohexyl, straight-chain or branched alkyl, having up to 5 carbon atoms, phenyl or benzyl, which is optionally substituted by fluorine, chlorine, bromine, phenyl or trifluoromethyl,
and/or the alkylene chain formed by $R^1$ and $R^2$ is optionally substituted by a spiro-linked radical of the formula

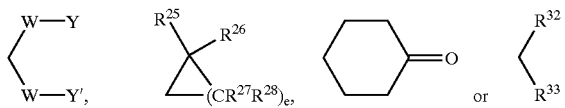

in which
W is either an oxygen or a sulphur atom,
Y and Y' together form a 2- to 5-membered straight-chain or branched alkyl chain,
e represents a number 1, 2, 3, 4, 5 or 6,
$R^{25}$, $R^{26}$, $R^{27}$ and $R^{28}$ are identical or different and each represents hydrogen, trifluoromethyl, phenyl, fluorine, chlorine, bromine or straight-chain or branched alkyl or alkoxy having in each case up to 5 carbon atoms,
or
$R^{25}$ and $R^{26}$ or $R^{27}$ and $R^{28}$, in each case together, form a straight-chain or branched alkyl chain having up to 5 carbon atoms or
$R^{25}$ and $R^{26}$ or $R^{27}$ and $R^{28}$, in each case together, form a radical of the formula $$W-CH_2 \atop W-(CH_2)_g,$$

in which
W is as defined above,
g represents a number 1, 2, 3, 4, 5 or 6,
$R^{32}$ and $R^{33}$ together form a 5- to 6-membered heterocycle which contains an oxygen or sulphur atom or a group of the formula NH or $NCH_3$, and stereoisomers, stereoisomer mixtures and salts thereof.

3. Compounds of the formula (I) according to claim 1, in which

A represents phenyl, pyridyl or thienyl, which are optionally substituted up to 2 times by identical or different substituents selected from the group consisting of fluorine, chlorine, bromine, hydroxyl, trifluoromethyl, trifluoromethoxy or by straight-chain or branched alkyl or alkoxy having in each case up to 5 carbon atoms, D represents a radical of the formula $$R^6 \underset{}{\overset{R^7 \ R^8}{\diagdown \diagup}} \quad \text{or} \quad R^9-T-V-X-$$

in which
$R^6$ and $R^9$ independently of one another each represent cyclopropyl, cyclopentyl or cyclohexyl, or
phenyl, naphthyl, pyridyl, tetrazolyl, pyrimidyl, pyrazinyl, phenoxathiin-2-yl, indolyl, imidazolyl, pyrrolidinyl, morpholinyl, benzothiazolyl, benzoxazolyl, furyl, quinolyl or purin-8-yl,
where the cycles are optionally substituted up to 3 times, in the case of the nitrogen-containing rings also via the N-function, by identical or different substituents selected from the group consisting of fluorine, chlorine, trifluoromethyl, hydroxyl, cyano, carboxyl, trifluoromethoxy, straight-chain or branched alkyl, alkylthio, alkylalkoxy, alkoxy or alkoxycarbonyl having in each case up to 4 carbon atoms, triazolyl, tetrazolyl, benzothiazolyl, trifluoromethyl-substituted phenyl and phenyl
and/or substituted by a group of the formula $-OR^{10}$, $-SR^{11}$ or $-SO_2R^{12}$,
in which
$R^{10}$, $R^{11}$ and $R^{12}$ are identical or different and each represents phenyl which for its part is substituted up to 2 times by identical or different substituents selected from the group consisting of phenyl, fluorine, chlorine or by straight-chain or branched alkyl having up to 3 carbon atoms,
or
$R^6$ represents a radical of the formula $R^7$ represents hydrogen or fluorine,
and
$R^8$ represents hydrogen, fluorine, chlorine, azido, trifluoromethyl, hydroxyl, trifluoromethoxy, or straight-chain or branched alkoxy or alkyl having in each case up to 4 carbon atoms or a radical of the formula $-NR^{15}R^{16}$,
in which
$R^{15}$ and $R^{16}$ are identical or different and each represents hydrogen or straight-chain or branched alkyl having up to 3 carbon atoms,
or
$R^7$ and $R^8$ together form a radical of the formula =O or $=NR^{17}$,
in which
$R^{17}$ represents hydrogen or straight-chain or branched alkyl, alkoxy or acyl having in each case up to 4 carbon atoms,
L represents a straight-chain or branched alkylene or alkenylene chain, having in each case up to 5 carbon atoms, which is optionally substituted up to 2 times by hydroxyl,
T and X are identical or different and each represents a straight-chain or branched alkylene chain having up to 3 carbon atoms,
or
T or X represents a bond,
V represents an oxygen or sulphur atom or represents a group of the formula $-NR^{18}$,
in which
$R^{18}$ represents hydrogen or straight-chain or branched alkyl having up to 3 carbon atoms,
E represents cyclopropyl, cyclobutyl, cyclopentyl or cyclohexyl or phenyl which is optionally substituted by fluorine or trifluoromethyl, or represents straight-chain or branched alkyl, having up to 4 carbon atoms, which is optionally substituted by hydroxyl,
$R^1$ and $R^2$ together form a straight-chain or branched alkylene chain, having up to 5 carbon atoms, which has to be substituted by a carbonyl group and/or a radical of the formula or $-OR^{19}$ in which
$R^{19}$ represents hydrogen, cyclopropyl, cyclopentyl, cyclohexyl, straight-chain or branched silylalkyl having up to 6 carbon atoms or straight-chain or branched alkyl, having up to 4 carbon atoms, which is optionally substituted by hydroxyl, straight-chain or branched alkoxy having up to 3 carbon atoms or by phenyl, which for its part may be substituted by fluorine, chlorine, bromine, nitro, trifluoromethyl, trifluoromethoxy or by phenyl or tetrazole-substituted phenyl,
and alkyl is optionally substituted by a group of the formula $-OR^{22}$,
in which
$R^{22}$ is straight-chain or branched acyl having up to 3 carbon atoms or benzyl,
or
$R^{19}$ is straight-chain or branched acyl having up to 15 carbon atoms or benzoyl which is optionally substituted by fluorine, chlorine, bromine, trifluoromethyl, nitro or trifluoromethoxy, or
straight-chain or branched fluoracyl having up to 4 carbon atoms,
and the alkylene chain formed by $R^1$ and $R^2$ is optionally substituted up to 4 times, optionally also geminally, by identical or different substituents selected from the group consisting of fluorine, hydroxyl, trifluoromethyl, carboxyl, azido, chlorine, bromine, nitro, cyano, cyclopropyl, cyclobutyl, cyclopentyl, cyclohexyl, cyclopropyloxy, cyclopentyloxy, cyclohexyloxy, by straight-chain or branched alkoxycarbonyl, alkoxy or alkylthio having in each case up to 4 carbon atoms or by straight-chain or branched alkyl, having up to 4 carbon atoms, which for its part is substituted up to 2 times by identical or different constituents selected from the group consisting of hydroxyl, benzyloxy, trifluoromethyl, benzoyl, methoxy, oxyacetyl and phenyl which for its part may be substituted by fluorine, chlorine, bromine, trifluoromethyl or trifluoromethoxy, and/or the alkylene chain which is formed by $R^1$ and $R^2$ is optionally substituted, also geminally, up to 4 times by identical or different substituents selected from the group consisting of phenyl, benzoyl, thiophenyl and sulphonylbenzyl which for their part are optionally substituted by fluorine, trifluoromethyl, trifluoromethoxy or nitro, and/or is optionally substituted by a radical of the formula

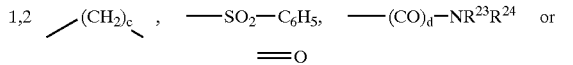

in which
c represents a number 1, 2, 3 or 4,
d represents a number 0 or 1,
$R^{23}$ and $R^{24}$ are identical or different and each represents hydrogen, cyclopropyl, cyclopentyl, benzyl, straight-chain or branched alkyl having up to 4 carbon atoms or phenyl which is optionally substituted by fluorine, chlorine or bromine, and/or the alkylene chain formed by $R^1$ and $R^2$ is optionally substituted by a spiro-linked radical of the formula

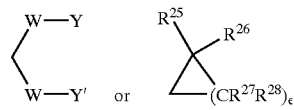

in which
W represents either an oxygen or a sulphur atom,
Y and Y' together form a 2- to 6-membered straight-chain or branched alkylene chain,
e represents a number 1, 2, 3, 4 or 5,
$R^{25}$, $R^{26}$, $R^{27}$ and $R^{28}$ are identical or different and each represents hydrogen, trifluoromethyl, phenyl, fluorine, chlorine, bromine or straight-chain or branched alkyl or alkoxy having in each case up to 4 carbon atoms,
or
$R^{25}$ and $R^{26}$ or $R^{27}$ and $R^{28}$, in each case together, form a straight-chain or branched alkyl chain having up to 4 carbon atoms,
or
$R^{25}$ and $R^{26}$ or $R^{27}$ and $R^{28}$, in each case together, form a radical of the formula

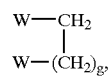

in which
W is as defined above,
g represents a number 1, 2, 3, 4, 5, 6 or 7,
and stereoisomers, stereoisomer mixtures and salts thereof.

4. Compounds of the formula (I) according to claim 1, in which
A represents optionally fluorine-substituted phenyl, in particular 4-fluorophenyl,
and
D represents a radical of the formula

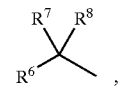

in which
$R^6$ represents phenyl or trifluoromethyl-substituted phenyl, preference being given to trifluoromethyl-substituted phenyl,
$R^7$ represents hydrogen,
$R^8$ represents hydrogen, fluorine, methoxy or hydroxyl, preference being given to fluorine,
or
$R^7$ and $R^8$ together form a carbonyl group,
E represents cyclopropyl, cyclopentyl or cyclohexyl, or represents straight-chain or branched alkyl, having up to 4 carbon atoms, which is optionally substituted by hydroxyl,
and
$R^1$ and $R^2$ together represent a radical of the formula

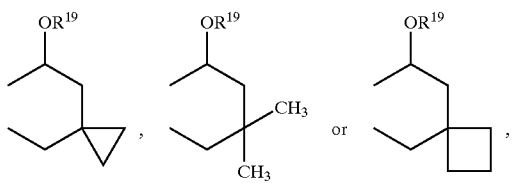

in which
$R^{19}$ represents hydrogen,
and stereoisomers, stereoisomer mixtures and salts thereof.

5. Process for preparing compounds according to claim 1, characterized in that
[A] compounds of the general formula (II)

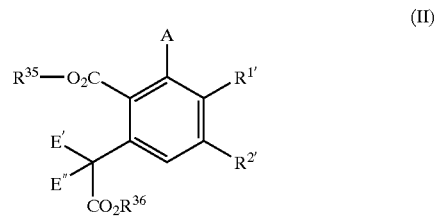

(II)

in which
A is as defined above,
$R^{35}$ and $R^{36}$ are identical or different and each represents straight-chain or branched alkyl having up to 4 carbon atoms,
$R^{1'}$ and $R^{2'}$ together represent the straight-chain or branched alkylene chain, having up to 7 carbon atoms, mentioned above under $R^1$ and $R^2$, which is substituted by tert-butyl-dimethyl-silanyloxy (OTBS), and E' and E" together with the carbon atom to which they are attached have the range of meanings of E given above, are initially converted by selective reduction of the aliphatic ester and subsequent reaction with compounds of general formula (III)

in which $R^{37}$ represents mesyl, tosyl or sulphonyl, and

Halogen represents chlorine, bromine or iodine, preferably chlorine, in inert solvents, in the presence of a base, into the compounds of the general formula (IV)

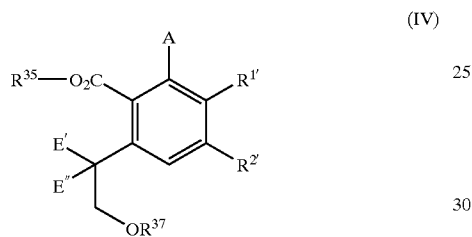

in which

A, E', E", $R^{1'}$, $R^{2'}$, $R^{35}$ and $R^{37}$ are each as defined above, these are converted in a further step, depending on the definitions of E'/E" given above, either by a two-fold reduction or by hydrolysis, Barton reaction and a reduction, into the compounds of the general formula (V)

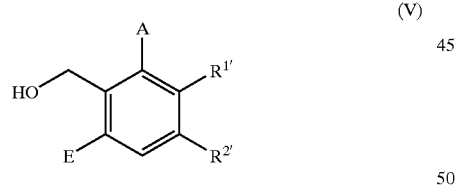

in which

A, E, $R^{1'}$ and $R^{2'}$ are each as defined above, the aldehydes of the general formula (VI)

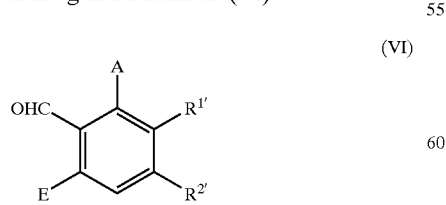

in which

A, E, $R^{1'}$ and $R^{2'}$ are each as defined above, are subsequently prepared by oxidation and finally, for example by a Grignard reaction, the formyl group is converted into the radical D and the TBS group is cleaved off by customary methods, or

[B] compounds of the general formula (VI)

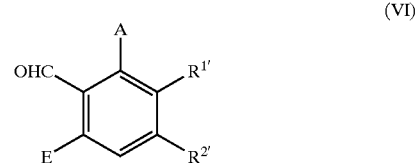

in which

A, E, $R^{1'}$ and $R^{2'}$ are each as defined above, are initially, as described in [A], converted in a Grignard reaction with compounds of the general formula (VII)

in which $R^{38}$ has the meaning of $R^5$ and $R^6$ given above, in inert solvents and under an atmosphere of protective gas, into the compounds of the general formula (VIII)

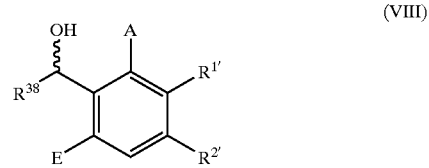

in which

A, D, E, $R^{38}$, $R^{1'}$ and $R^{2'}$ are each as defined above, if appropriate on this stage starting from the hydroxyl function the substituents $R^7/R^8$ given under D are introduced by customary methods, and the TBS group is subsequently cleaved off using tetrabutylammoniumfluoride in inert solvents, or

[C] compounds of the general formula (IX)

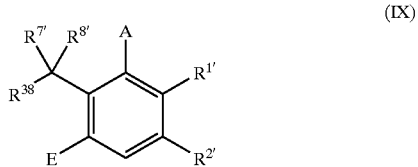

in which

A, E, $R^{1'}$, $R^{2'}$ and $R^{38}$ are each as defined above and $R^{7'}$ and $R^{8'}$ together represent the carbonyl group, are initially reduced to the compounds of the general formula (VIII) and subsequently reacted as described under [A], or

[D] compounds of the general formula (X)

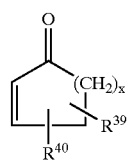
(X)

in which x represents a number 1, 2 or 3, and $R^{39}$ and $R^{40}$ are identical or different and each represents hydrogen or represents straight-chain or branched alkyl having up to 6 carbon atoms, it also being possible for $R^{39}$ and $R^{40}$ to be positioned geminally, or $R^{39}$ and $R^{40}$ together form a spiro-linked carbocycle having 3 to 7 carbon atoms, are converted with compounds of the general formula (XI)

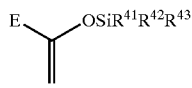
(XI)

where

E is as defined above, and $R^{41}$, $R^{42}$ and $R^{43}$ are identical or different and each represents straight-chain or branched alkyl having up to 10 carbon atoms, in the presence of a metal or semi-metal reagent, initially via the intermediate stage of the general formula (XII)

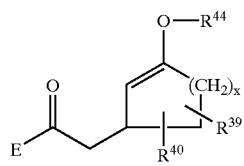
(XII)

in which x, E, $R^{39}$ and $R^{40}$ are each as defined above, and $R^{44}$ represents metal or semi-metal derivatives, preferably those of titanium, and by addition of the compounds of the general formula (XIII)

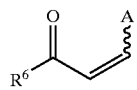
(XIII)

in which $R^6$ and A are each as defined above, via intermediates of the general formula (XIV)

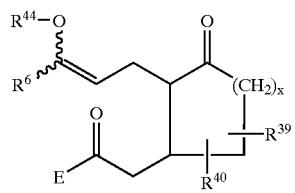
(XIV)

in which

A, E, $R^6$, $R^{39}$, $R^{40}$, $R^{44}$ and x are each as defined above, into the compounds of the general formula (XV)

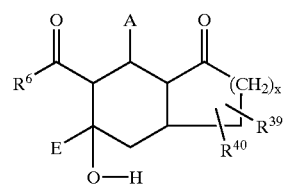
(XV)

in which

A, E, $R^6$, $R^{39}$, $R^{40}$ and x are each as defined above, the compounds of the general formula (XVI)

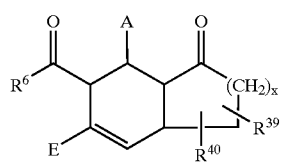
(XVI)

in which

A, E, $R^6$, $R^{39}$, $R^{40}$ and x are each as defined above, are subsequently prepared by an elimination, halogen compounds, for example the compounds of the general formula (XVII) and/or (XVIIa)

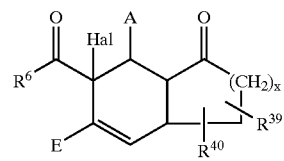
(XVII)

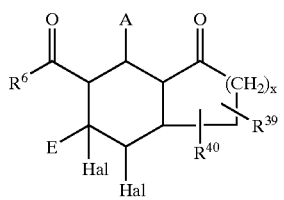
(XVIIa)

in which $R^6$, $R^{39}$, $R^{40}$, x, A and E are as defined above, and

Hal represents halogen, preferably chlorine or bromine, are prepared in a further step by a halogenation via the cyclohexadienes of the general formula (XVIII), which are formed in situ, or isomers thereof

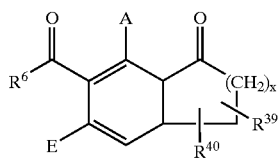

(XVIII)

in which

A, E, x, $R^6$, $R^{39}$ and $R^{40}$ are each as defined above, compounds of the general formula (XIX)

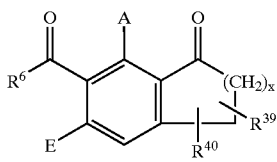

(XIX)

in which

A, E, x, $R^6$, $R^{39}$ and $R^{40}$ are each as defined above are prepared after oxidation, furthermore, the compounds of the general formula (XX)

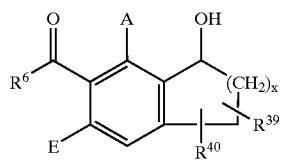

(XX)

in which

A, E, x, $R^6$, $R^{39}$ and $R^{40}$ are each as defined above, are prepared by the reduction of the ketofunction, it also being possible to carry out the reduction stereoselectively, the compounds of the general formula (XXI)

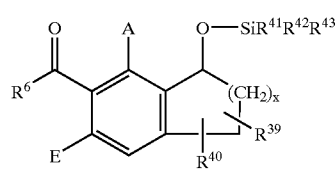

(XXI)

in which x, A, E, $R^6$, $R^{39}$, $R^{40}$, $R^{41}$, $R^{42}$ and $R^{43}$ are each as defined above, are subsequently prepared by silylation, for example by reaction with chlorinated or trifluoromethanesulfonyl-substituted silyl compounds (—$SiR^{41}R^{42}R^{43}$)

furthermore, the compounds of the general formula (XXII)

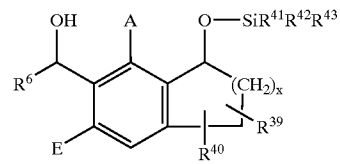

(XXII)

in which x, A, E, $R^6$, $R^{39}$, $R^{40}$, $R^{41}$, $R^{42}$ and $R^{43}$ are each as defined above, are obtained initially by reduction of the second ketone function, as a mixture of diastereomers from which subsequently, by separation, the isomer of the general formula (XXIII)

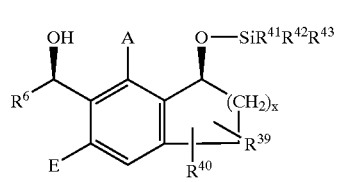

(XXIII)

in which x, A, E, $R^6$, $R^{39}$, $R^{40}$, $R^{41}$, $R^{42}$ and $R^{43}$ are each as defined above are obtained, and, if appropriate, the hydroxyl function is replaced enantioselectively by nucleophilic substitution by one of the substituents listed above under $R^8$, thus giving compounds of the general formula (XXIV)

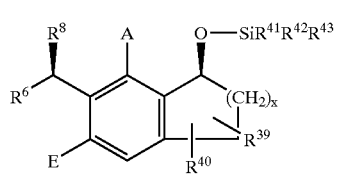

(XXIV)

in which x, A, E, $R^6$, $R^8$, $R^{39}$, $R^{40}$, $R^{41}$, $R^{42}$ and $R^{43}$ are each as defined above and, in a last step, the hydroxyl function is liberated according to customary methods by cleaving off the silyl protective group, and, in the case of enantiomers/racemates, is separated by customary methods, where the structures of the general formulae (XV), (XVI), (XVII), (XVIIa) and (XVIII) may occur in isomeric forms.

6. Compounds of the general formula (XV)

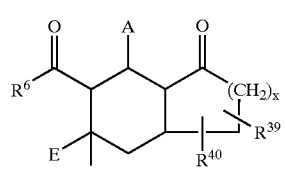

(XV)

in which

A, E, and $R^6$ are each as defined in claim 1 and $R^{39}$, $R^{40}$ and x are each as defined in claim 5, and their stereoisomers.

7. Compounds of the general formula (XIX)

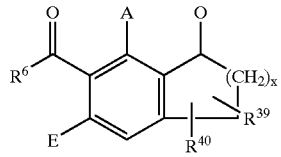

(XIX)

in which

A, E, and $R^6$ are each as defined in claim 1 and $R^{39}$, $R^{40}$ and x are each as defined in claim 6 and their stereoisomers.

8. Compounds of the general formula (XXII)

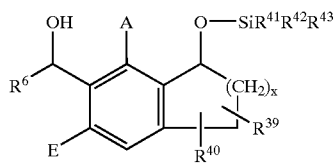

(XXII)

in which

A, E, and $R^6$ are each as defined in claim 1 and $R^{39}$, $R^{40}$ and x are each as defined in claim 6 and their stereoisomers.

9. Pharmaceutical comprising at least one compound according to claim 1 and pharmacologically acceptable formulation auxiliaries.

10. A method of treating hyperlipoproteinaemia, comprising administering to a patient in need thereof an effective amount of a compound according to claim 1.

11. A method of treating arteriosclerosis, comprising administering to a patient in need thereof an effective amount of a compound according to claim 1.

12. A method of treating dyslipidaemia, comprising administering to a patient in need thereof an effective amount of a compound according to claim 1.

* * * * *